(12) United States Patent
Burgess et al.

(10) Patent No.: US 8,153,652 B2
(45) Date of Patent: *Apr. 10, 2012

(54) FAB I INHIBITORS

(75) Inventors: Walter J. Burgess, Collegeville, PA (US); Dalia R. Jakas, Norristown, PA (US); William F. Huffman, King of Prussia, PA (US); William H. Miller, Collegeville, PA (US); Kenneth A. Newlander, West Chester, PA (US); Mark A. Seefeld, Collegeville, PA (US); Irene N. Uzinskas, Villanova, PA (US)

(73) Assignee: Affinium Pharmaceuticals, Inc., Toronto, Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 12/758,227

(22) Filed: Apr. 12, 2010

(65) Prior Publication Data

US 2011/0098277 A1 Apr. 28, 2011

Related U.S. Application Data

(60) Continuation of application No. 11/767,967, filed on Jun. 25, 2007, now Pat. No. 7,741,339, which is a division of application No. 11/284,660, filed on Nov. 22, 2005, now Pat. No. 7,250,424, which is a division of application No. 10/474,315, filed as application No. PCT/US02/10332 on Apr. 3, 2002, now Pat. No. 7,049,310.

(60) Provisional application No. 60/282,225, filed on Apr. 6, 2001.

(51) Int. Cl.
A61K 31/4375 (2006.01)
C07D 471/04 (2006.01)

(52) U.S. Cl. ..... 514/300; 546/122; 546/113; 546/268.1; 544/242; 514/256; 514/336

(58) Field of Classification Search ............... 514/300, 514/256, 336; 546/122, 113, 268.1; 544/242
See application file for complete search history.

(56) References Cited

U.S. PATENT DOCUMENTS

| | | | |
|---|---|---|---|
| 3,828,068 A | 8/1974 | Minieri | |
| 4,154,943 A | 5/1979 | Kuehne | |
| 4,977,159 A | 12/1990 | Sevrin et al. | |
| 5,416,193 A | 5/1995 | Desai | |
| 5,614,551 A | 3/1997 | Dick et al. | |
| 5,624,941 A | 4/1997 | Barth et al. | |
| 5,932,743 A | 8/1999 | Collini et al. | |
| 5,985,867 A | 11/1999 | Rodgers et al. | |
| 5,989,832 A | 11/1999 | Trias et al. | |
| 6,133,260 A | 10/2000 | Matzke et al. | |
| 6,174,878 B1 | 1/2001 | Gamache et al. | |
| 6,184,380 B1 | 2/2001 | Chiu et al. | |
| 6,187,341 B1 | 2/2001 | Johnson et al. | |
| 6,194,429 B1 | 2/2001 | Guinn et al. | |
| 6,194,441 B1 | 2/2001 | Roberts et al. | |
| 6,198,000 B1 | 3/2001 | Hawkins | |
| 6,221,859 B1 | 4/2001 | Dorso et al. | |
| 6,221,864 B1 | 4/2001 | Hirayama et al. | |
| 6,235,908 B1 | 5/2001 | Fey | |
| 6,239,113 B1 | 5/2001 | Dawson et al. | |
| 6,239,141 B1 | 5/2001 | Allen et al. | |
| 6,248,363 B1 | 6/2001 | Patel et al. | |
| 6,267,985 B1 | 7/2001 | Chen et al. | |
| 6,277,836 B1 | 8/2001 | Borody | |
| 6,288,239 B1 | 9/2001 | Hollingsworth et al. | |
| 6,291,462 B1 | 9/2001 | Bartholomaeus et al. | |
| 6,294,192 B1 | 9/2001 | Patel et al. | |
| 6,303,572 B1 | 10/2001 | Rowe | |
| 6,309,663 B1 | 10/2001 | Patel et al. | |
| 6,333,045 B1 | 12/2001 | Yasueda et al. | |
| 6,340,689 B1 | 1/2002 | Dubois et al. | |
| 6,346,391 B1 | 2/2002 | Oethinger et al. | |
| 6,367,985 B1 | 4/2002 | Lee et al. | |
| 6,372,752 B1 | 4/2002 | Staveski et al. | |
| 6,388,070 B1 | 5/2002 | Deshpande et al. | |
| 6,395,746 B1 | 5/2002 | Cagle et al. | |
| 6,399,629 B1 | 6/2002 | Chamberland et al. | |
| 6,406,880 B1 | 6/2002 | Thornton | |
| 6,423,341 B1 | 7/2002 | Yamaguchi | |
| 6,423,741 B1 | 7/2002 | Khanuja et al. | |
| 6,428,579 B1 | 8/2002 | Valentini | |
| 6,432,444 B1 | 8/2002 | Fischetti et al. | |
| 6,436,980 B1 | 8/2002 | Leger et al. | |
| 6,441,162 B2 | 8/2002 | Yasui et al. | |
| 6,448,054 B1 | 9/2002 | Poznansky et al. | |
| 6,448,238 B1 | 9/2002 | Shoichet et al. | |
| 6,448,449 B2 | 9/2002 | Larrow | |
| 6,451,339 B2 | 9/2002 | Patel et al. | |

(Continued)

FOREIGN PATENT DOCUMENTS

CA 2444597 A1 10/2002

(Continued)

OTHER PUBLICATIONS

Abou-Gharbia et al., "Psychotropic Agents: Synthesis and Antipysychotic Activity of Substituted B-Carbolines," *J. Med. Chem.*, 30(6), 1987, pp. 1100-1115.

Ahsan et al., "Reserpine Anlogues: Synthesis of B-Carboline Derivatives," *J. Chem. Soc.*, 1963, pp. 3928-3920.

Bergler et al., "Protein EnvM is the NADH-dependent Enoyl-ACP Reductase (FabI) of *Escherichia coli*," *J. Biol. Chem.*, 269(8), 1994, pp. 5493-5496.

Claus et al., "Formaldehydabspaltende Phenolearbonaaurederlvate," *Monatsh. Chem.*, 97, 1966, pp. 271-279.

Database CA on STN, AN 7:66733, Rosenmund et al., "Chemistry of indole II . . . ," Chem Ber. 103(2), 1970, pp. 496-509.

Database CAOLD on STN, AN CA51:10524d, Hellman et al., "N-Mannich bases (VI) condensation . . . ," Direct Submission, 1953, 1 page.

Database CAPLUS on STN, AN 1977:439214, Misztal et al., "Synthesis and pharmacologic properties of pyridoyl . . . ," *Arch. Immunol. Ther. Exp.*, 24(6), 1976, pp. 851-862.

Database CAPLUS on STN, AN 1986:68547, Stuetz et al., "Synthesis and Structure Activity . . . ," *J. Med Chem.* 29(1), 1986, pp. 112-125.

(Continued)

Primary Examiner — Charanjit Aulakh
(74) Attorney, Agent, or Firm — Goodwin Procter LLP

(57) ABSTRACT

Compounds are disclosed which are Fab I inhibitors and are useful in the treatment bacterial infections.

3 Claims, No Drawings

U.S. PATENT DOCUMENTS

| | | |
|---|---|---|
| 6,451,816 B1 | 9/2002 | Biedermann et al. |
| 6,461,607 B1 | 10/2002 | Farmer |
| 6,461,829 B1 | 10/2002 | Kahne |
| 6,465,429 B1 | 10/2002 | Hancock et al. |
| 6,468,964 B1 | 10/2002 | Rowe |
| 6,469,046 B1 | 10/2002 | Daines et al. |
| 6,486,148 B2 | 11/2002 | Savage et al. |
| 6,486,149 B2 | 11/2002 | Onodera et al. |
| 6,486,165 B2 | 11/2002 | Zhang et al. |
| 6,489,318 B1 | 12/2002 | Copar et al. |
| 6,492,351 B1 | 12/2002 | Zhang et al. |
| 6,495,158 B1 | 12/2002 | Buseman et al. |
| 6,495,161 B1 | 12/2002 | Soon-Shiong et al. |
| 6,495,551 B1 | 12/2002 | Betts et al. |
| 6,497,886 B1 | 12/2002 | Breitenbach et al. |
| 6,500,459 B1 | 12/2002 | Chhabra et al. |
| 6,500,463 B1 | 12/2002 | van Lengerich |
| 6,503,539 B2 | 1/2003 | Gestrelius et al. |
| 6,503,881 B2 | 1/2003 | Krieger et al. |
| 6,503,903 B1 | 1/2003 | Miller et al. |
| 6,503,906 B1 | 1/2003 | Lee |
| 6,503,908 B1 | 1/2003 | Maw |
| 6,503,953 B2 | 1/2003 | Vyden |
| 6,503,955 B1 | 1/2003 | Dobrozsi et al. |
| 6,509,327 B1 | 1/2003 | Cagle et al. |
| 6,514,535 B2 | 2/2003 | Marchant |
| 6,514,541 B2 | 2/2003 | Khanuja et al. |
| 6,514,953 B1 | 2/2003 | Armitage et al. |
| 6,514,962 B1 | 2/2003 | Shibatani et al. |
| 6,514,986 B2 | 2/2003 | de Souza et al. |
| 6,515,113 B2 | 2/2003 | Raymond et al. |
| 6,517,827 B1 | 2/2003 | Bacon Kurtz et al. |
| 6,518,239 B1 | 2/2003 | Kuo et al. |
| 6,518,263 B1 | 2/2003 | Nishitani et al. |
| 6,518,270 B1 | 2/2003 | Amin et al. |
| 6,518,487 B1 | 2/2003 | Lowe et al. |
| 6,521,408 B1 | 2/2003 | Kawasaki |
| 6,525,066 B2 | 2/2003 | Fukumoto et al. |
| 6,527,759 B1 | 3/2003 | Tachibana et al. |
| 6,528,089 B1 | 3/2003 | Kothrade et al. |
| 6,531,126 B2 | 3/2003 | Farmer |
| 6,531,291 B1 | 3/2003 | Kabbash et al. |
| 6,531,465 B1 | 3/2003 | Ascher et al. |
| 6,531,508 B1 | 3/2003 | Nomura et al. |
| 6,531,649 B1 | 3/2003 | Mannerloef et al. |
| 6,559,172 B1 | 5/2003 | Heerding et al. |
| 6,573,272 B1 | 6/2003 | Miller et al. |
| 6,673,941 B2 | 1/2004 | Heerding et al. |
| 6,730,684 B1 | 5/2004 | Miller et al. |
| 6,762,201 B1 | 7/2004 | Miller et al. |
| 6,765,005 B2 | 7/2004 | Miller et al. |
| 6,821,746 B2 | 11/2004 | DeWolf, Jr. et al. |
| 6,846,819 B1 | 1/2005 | Miller et al. |
| 6,951,729 B1 | 10/2005 | Dewolf, Jr. et al. |
| 6,964,970 B2 | 11/2005 | Miller et al. |
| 6,995,254 B1 | 2/2006 | Payne et al. |
| 7,048,926 B2 | 5/2006 | Brandt et al. |
| 7,049,310 B2 | 5/2006 | Burgess et al. |
| 7,250,424 B2 * | 7/2007 | Burgess et al. ............... 514/300 |
| 7,524,843 B2 | 4/2009 | Miller et al. |
| 7,557,125 B2 | 7/2009 | Miller et al. |
| 7,741,339 B2 * | 6/2010 | Burgess et al. ............... 514/300 |
| 7,790,716 B2 | 9/2010 | Miller et al. |
| 2003/0232850 A1 | 12/2003 | Miller et al. |
| 2004/0053814 A1 | 3/2004 | Brandt et al. |
| 2005/0250810 A1 | 11/2005 | Miller et al. |
| 2006/0142265 A1 | 6/2006 | Berman et al. |
| 2006/0183908 A1 | 8/2006 | Berman et al. |
| 2008/0125423 A1 | 5/2008 | Miller et al. |
| 2009/0042927 A1 | 2/2009 | Pauls et al. |
| 2009/0156578 A1 | 6/2009 | Pauls et al. |
| 2010/0093705 A1 | 4/2010 | Sargent et al. |
| 2010/0130470 A1 | 5/2010 | Pauls et al. |
| 2011/0124633 A1 | 5/2011 | Berman et al. |
| 2011/0190283 A1 | 8/2011 | Miller et al. |

FOREIGN PATENT DOCUMENTS

| | | |
|---|---|---|
| EP | 0407200 | 1/1991 |
| EP | 1000935 | 5/2000 |
| HU | 210679 B | 6/1995 |
| HU | 0203122 | 1/2003 |
| WO | WO-93/04035 A1 | 3/1993 |
| WO | WO-95/18619 | 7/1995 |
| WO | WO-96/00730 | 1/1996 |
| WO | WO-97/48696 | 12/1997 |
| WO | WO-98/57952 | 12/1998 |
| WO | WO-99/24406 | 5/1999 |
| WO | WO-00/27628 | 5/2000 |
| WO | WO-00/57933 | 10/2000 |
| WO | WO-01/14364 | 3/2001 |
| WO | WO-01/26652 | 4/2001 |
| WO | WO-01/26654 | 4/2001 |
| WO | WO-01/27103 | 4/2001 |
| WO | WO-01/41573 | 6/2001 |
| WO | WO-01/48248 | 7/2001 |
| WO | WO-01/70172 | 9/2001 |
| WO | WO-02/10332 | 2/2002 |
| WO | WO-02/42273 | 5/2002 |
| WO | WO-02/48097 | 6/2002 |
| WO | WO-02/064572 | 8/2002 |
| WO | WO-03/086396 | 10/2003 |
| WO | WO-2004/014869 | 2/2004 |
| WO | WO-2004/052890 | 6/2004 |
| WO | WO-2004/082586 | 9/2004 |
| WO | WO-2007/053131 | 5/2007 |
| WO | WO-2007/067416 | 6/2007 |
| WO | WO-2008/009122 | 1/2008 |

OTHER PUBLICATIONS

Database CAPLUS on STN, AN 1991:428908, Fuse et al., "Preparation of cinnamamide derivatives . . . ," EP407200A1, 1991, 3 pages.

Database CAPLUS on STN, AN 1999:325910, Aslanian et al., "Preparation of phenylalkylimidazoles . . . ," WO/99/24406, 1999, 2 pages.

Database Crossfire Beilstein, Database Accession No. 2819049, 2819050, XP002216033, 1966, 2 pages.

Grassberger et al., "Preparation and Antibacterial Activities of New 1,2,3-Diazaborine Derivatives and Analogues," *J. Med. Chem.*, 27, 1984, pp. 947-953.

Heath et al., "A Triclosan-Resistant Bacterial Enzyme," *Nature*, 406, 2000, pp. 145-146.

Heath et al., "Regulation of Fatty Acid Elongation and Initiation by Acyl-Acyl Carrier Protein in *Escherichia coli*," *J. Biol. Chem.*, 271(4), 1996, pp. 1833-1836.

Heck, *Organic Reactions*, 27, 1982, pp. 345-390.

Himmler et al., "Synthesis and Antibacterial in Vitro Activity of Novel Analogues of Nematophin," *Bioorg. Med. Chem. Lett.*, 8(15), 1998, pp. 2045-2050.

Hungarian Search Report for Hungarian Patent Application No. P0203122, dated Dec. 31, 2003, 1 page.

International Search Report dated Oct. 4, 2000 for PCT Application No. PCT/US2000/15154, 2 pages.

International Search Report dated Jan. 25, 2001 for PCT Application No. PCT/US2000/27844, 3 pages.

International Search Report dated Jan. 29, 2001 for PCT Application No. PCT/US2000/27591, 1 page.

International Search Report dated Feb. 22, 2001 for PCT Application No. PCT/US2000/27619, 3 pages.

International Search Report dated Apr. 21, 2004 for PCT Application No. PCT/US2003/38706, 5 pages.

International Search Report dated Oct. 13, 2004 for PCT Application No. PCT/IB2004/001261, 3 pages.

International Search Report dated Apr. 20, 2005 for PCT Application No. PCT/US2002/10332, 3 pages.

International Search Report dated Jun. 14, 2007 for PCT Application No. PCT/US2005/019805, 4 pages.

International Search Report dated Sep. 12, 2007 for PCT Application No. PCT/US2006/045903, 6 pages.

International Search Report dated Oct. 26, 2007 for PCT Application No. PCT/CA2007/001277, 3 pages.

International Search Report dated Apr. 7, 2008 for PCT Application No. PCT/CA2008/000300, 5 pages.

Li et al., "Synthesis and Antistaphylococcal Activity of Nematophin and Its Analogs," *Bioorg. Med. Chem. Lett.*, 7(10), 1977, pp. 1349-1352.

Jossang-Yanagida et al., "Tetrahydropyridoazepines and Tetrahydropyridoazepinones from the Corresponding Dihydroquinolones," *J. Heterocycl. Chem.*, 15, 1978, pp. 249-251.

Karlowsky et al., "In Vitro Activity of API-1252, a Novel FabI Inhibitor, against Clinical Isolates of *Staphylococcus aureus* and *Staphylococcus epidermidis*," *Antimicrob. Agents. Chemother.*, 51(4), 2007, pp. 1580-1581.

Levy et al., "Molecular Basis of Triclosan Activity," *Nature*, 398, 1999, pp. 383-384.

McMurray et al., "Triclosan Targets Lipid Synthesis," *Nature*, 394, 1998, pp. 531-532.

Miller et al., "Discovery of Aminopyridine-Based Inhibitors of Bacterial Enoyl-ACP Reductase (FABI)," *J. Med. Chem.*, 45, 2002, pp. 3246-3256.

Misztal et al., "Synthesis and Pharmacologic Properties of Pyridol Derivatives of 3-Methylaminoindole 2-Methyltryptamine and Isostryptamine," *Arch. Immunol. Ther. Exp.*, 24(6), 1976, pp. 851-852.

Pachter et al., "The Chemistry of Hortiamine and 6-Methoxyhetsinine," *J. Amer. Chem.*, 83, 1961, pp. 635-642.

Patent Abstract of Japan for Japanese Patent Publication No. JP 11-302173, published Nov. 2, 2009, 1 page.

Payne et al., "Bacterial Fatty-Acid Biosynthesis: A Genomics-Driven Target for Antibacterial Drug Discovery," *Drug Discov. Today*, 6(10), 2001, pp. 537-541.

Rehse et al., "Dopaminanaloge 1,2,3,4-Tetrahydro-B-Carboline," *Arch. Pharm.*, 311(1), 1978, pp. 11-18.

Seefeld et al., "Indole Naphthyridinones as Inhibitors of Bacterial Enoyl-ACP Reductases FabI and FabK," *J. Med. Chem.*, 46, 2003, pp. 1627-1635.

Shoji et al., "Two Novel Alkaloids from Evodia rutaecarpa," *J. Nat. Prod.*, 52(5), 1989, pp. 1160-1162.

Sladowska et al., "Synthesis and Properties of Amides of 1-Benzyl-3-methyl and 1-Butyl-3-phenyl-7-methyl-4-oxo-2-thioxo (2,4-dioxo)-1,2,3,4-tetrahydropyrido-[2,3-d]pyrimidine-6-carboxylic acids," *Farmaco Sci.*, 41, 1986, pp. 954-963.

Stuetz et al., "Synthesis and Structure-Activity Relationships of Naftifine-Related Allylamine Antimycotics," *J. Med. Chem.*, 29(1), 1986, pp. 112-125.

Turnowsky et al., "envM Genes of *Salmonella typhimurium* and *Escherichia coli*," *J. Bacteriol.*, 171(12), 1989, pp. 6555-6565.

Ward et al., "Kinetic and Structural Characteristics of the Inhibition of Enoyl (Acyl Carrier Protein) Reductase by Triclosan," *Biochemistry*, 38(38), 1999, pp. 12514-12525.

* cited by examiner

FAB I INHIBITORS

This application is a continuation of U.S. Ser. No. 11/767,967, filed Jun. 25, 2007, now U.S. Pat. No. 7,741,339, which is a divisional application of U.S. Ser. No. 11/284,660, filed Nov. 22, 2005, now U.S. Pat. No. 7,250,424, which is a divisional application of U.S. Ser. No. 10/474,315, filed Oct. 6, 2003, now U.S. Pat. No. 7,049,310, which is 371 national stage application of PCT/US02/10332, filed Apr. 3, 2002, which claims priority to U.S. Ser. No. 60/282,225 filed Apr. 6, 2001, all of which applications are incorporated herein by reference by their entireties.

FIELD OF THE INVENTION

This invention relates to pharmaceutically active compounds which inhibit Fab I and are useful for the treatment of bacterial infections.

BACKGROUND OF THE INVENTION

While the overall pathway of saturated fatty acid biosynthesis is similar in all organisms, the fatty acid synthase (FAS) systems vary considerably with respect to their structural organization. Vertebrates and yeast possess a FAS in which all the enzymatic activities are encoded on one or two polypeptide chains, respectively, and the acyl carrier protein (ACP) is an integral part of the complex. In contrast, in bacterial FAS, each of the reactions is catalyzed by a distinct, mono-functional enzyme and the ACP is a discrete protein. Therefore, there is considerable potential for the selective inhibition of the bacterial system by antibacterial agents.

Fab I (previously designated EnvM) functions as an enoyl-ACP reductase (Bergler, et al, (1994), *J. Biol. Chem.* 269, 5493-5496) in the final step of the four reactions involved in each cycle of bacterial fatty acid biosynthesis. In this pathway, the first step is catalyzed by β-ketoacyl-ACP synthase, which condenses malonyl-ACP with acetyl-CoA (FabH, synthase III). In subsequent rounds, malonyl-ACP is condensed with the growing-chain acyl-ACP (FabB and FabF, synthases I and II, respectively). The second step in the elongation cycle is ketoester reduction by NADPH-dependent β-ketoacyl-ACP reductase (FabG).

Subsequent dehydration by β-hydroxyacyl-ACP dehydrase (either FabA or FabZ) leads to trans-2-enoyl-ACP, which in turn is converted to acyl-ACP by NADH-dependent enoyl-ACP reductase (Fab I). Further rounds of this cycle, adding two carbon atoms per cycle, eventually lead to palmitoyl-ACP (16C), where upon the cycle is stopped largely due to feedback inhibition of Fab I by palmitoyl-ACP (Heath, et al, (1996), *J. Biol. Chem.* 271, 1833-1836). Thus, Fab I is a major biosynthetic enzyme and is a key regulatory point in the overall synthetic pathway of bacterial fatty acid biosynthesis. Therefore, Fab I is an ideal target for antibacterial intervention.

Studies have shown that diazaborine antibiotics inhibit fatty acid, phospholipid and lipopolysaccharide (LPS) biosynthesis and that the antibacterial target of these compounds is Fab I. For example, derivative 2b18 from Grassberger, et al, (1984) *J. Med Chem* 27, 947-953 has been reported to be a non-competitive inhibitor of Fab I (Bergler, et al, (1994) *J. Biol. Chem.* 269, 5493-5496). Also, plasmids containing the Fab I gene from diazaborine resistant *S. typhimurium* conferred diazaborine resistance in *E. coli* (Turnowsky, et al, (1989) *J. Bacteriol.*, 171, 6555-6565). Furthermore, inhibition of Fab I either by diazaborine or by raising the temperature in a Fab I temperature sensitive mutant is lethal. These results demonstrate that Fab I is essential to the survival of the organism (Bergler, et al, (1994) *J. Biol. Chem.* 269, 5493-5496).

Recent studies have shown that Fab I is also the target for the broad spectrum antibacterial agent triclosan (McMurry, et al, (1998) *Nature* 394, 531-532). A crystal structure of the *E. Coli* Fab I complexed with NAD and triclosan shows that triclosan acts as a site-directed, very potent inhibitor of Fab I by mimicking its natural substrate (Levy, et al, (1999) *Nature* 398, 383-384). Ward, et al ((1999) *Biochem.* 38, 12514-12525) have shown that there is no evidence for the formation of a covalent complex between Fab I and triclosan, which would be analogous to the diazaborines; triclosan differs from these compounds in that it is a reversible inhibitor of Fab I. The structural data for the complex of Fab I with NAD and triclosan provides important information about Fab I as a therapeutic target.

Importantly, it has now been discovered that certain compounds are Fab I inhibitors and have antibacterial activity, and, therefore, may be useful for the treatment of bacterial infections in mammals, particularly in man.

SUMMARY OF THE INVENTION

This invention comprises compounds, as described hereinafter, which inhibit Fab I and are useful in the treatment of bacterial infections.

This invention is also a pharmaceutical composition comprising compounds of the instant invention according and a pharmaceutically acceptable carrier.

This invention is a method of treating bacterial infections by inhibiting Fab I. In a particular aspect, the compounds of this invention are useful as antibacterial agents.

DETAILED DESCRIPTION

This invention comprises compounds of the formula (I):

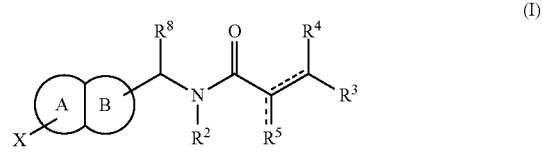

wherein:

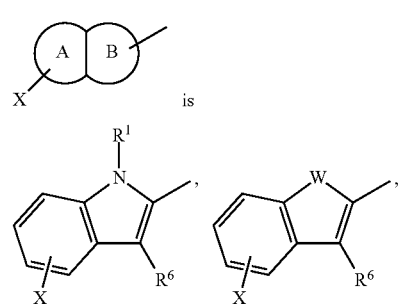

is

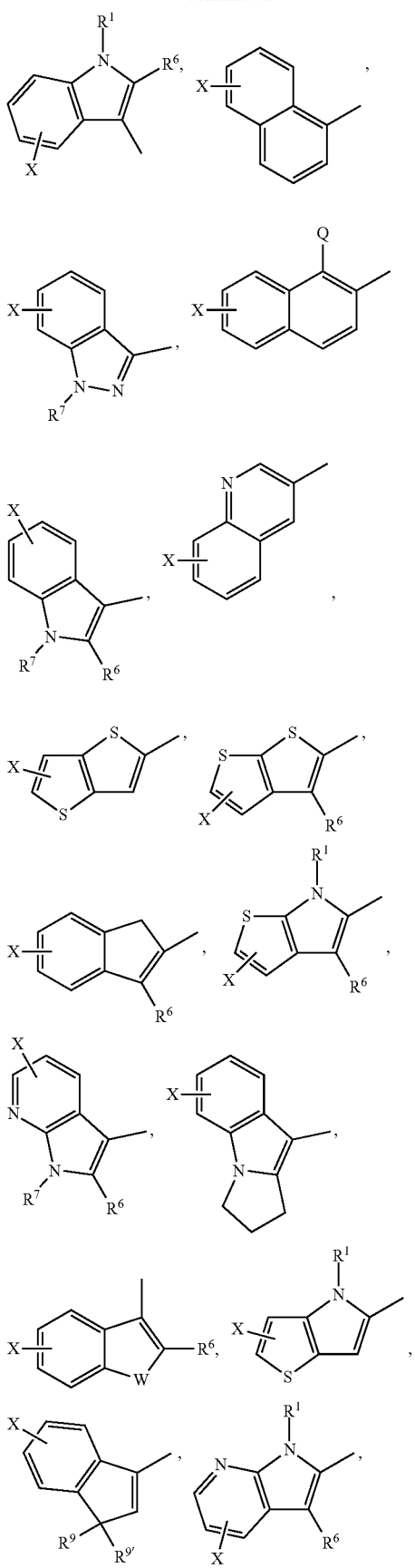

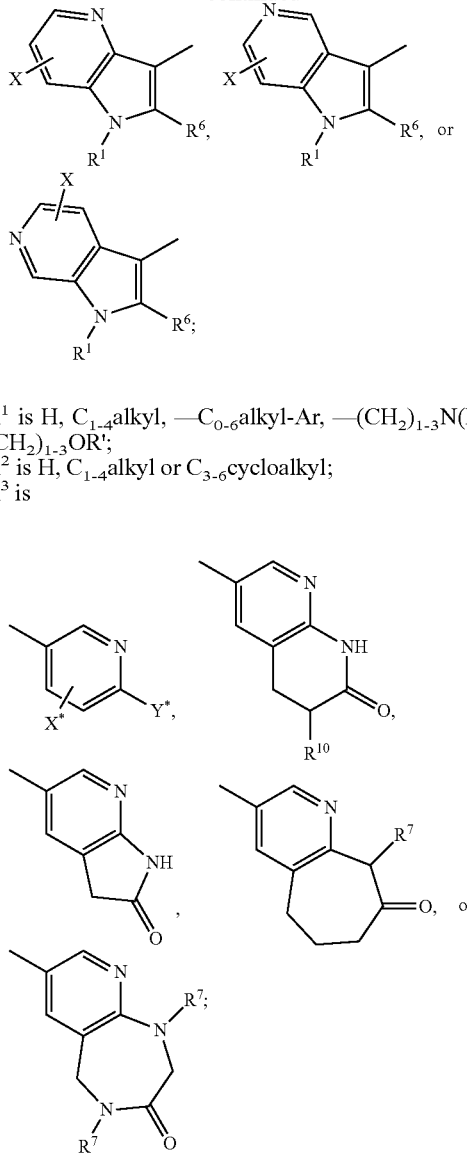

$R^1$ is H, $C_{1-4}$alkyl, —$C_{0-6}$alkyl-Ar, —$(CH_2)_{1-3}N(R')_2$, or —$(CH_2)_{1-3}OR'$;

$R^2$ is H, $C_{1-4}$alkyl or $C_{3-6}$cycloalkyl;

$R^3$ is $R^4$ is H or $C_{1-4}$alkyl;

indicates that one of the two designated bonds is a double bond and the other is a single bond;

$R^5$ is $CH_2$ when the bond to which it is attached is a double bond; or $R^5$ is H or $C_{1-4}$alkyl when the bond to which it is attached is a single bond;

$R^6$ is H or $C_{1-4}$alkyl;

each $R^7$ independently is H, $C_{1-6}$alkyl, —$C_{0-6}$alkyl-Ar, —$(CH_2)_{1-3}N(R')_2$, or —$(CH_2)_{1-3}OR'$;

$R^8$ is H or $C_{1-4}$alkyl;

$R^9$ and $R^{9'}$ independently are H or $C_{1-4}$alkyl;

$R^{10}$ is $C_{1-4}$alkyl, $N(R')_2$, NHC(O)R', $NHCH_2C(O)R'$ or NHC(O)CH=CHR;

$Y^*$ is $N(R')_2$, NHC(O)R', $NHCH_2C(O)R'$ or NHC(O)CH=CHR;

each X independently is H, $C_{1-4}$alkyl, $CH_2OH$, OR', SR', CN, $N(R')_2$, $CH_2N(R')_2$, $NO_2$, $CF_3$, $CO_2R'$, $CON(R)_2$, COR', NR'C(O)R', F, Cl, Br, I or $-S(O)_rCF_3$;

X* is $-(CH_2)_{1-3}C(O)N(R')-(CH_2)_{1-3}-Ar$ or $-(CH_2)_{1-3}C(O)N(R')-(CH_2)_{1-3}$-Het;

W is S or O;

Q is H or $C_{1-4}$alkyl;

each R' independently is H, $C_{1-6}$alkyl, $-C_{0-6}$alkyl-Ar or $-C_{0-6}$ alkyl-Het; and r is 0, 1 or 2;

or a pharmaceutically acceptable salt thereof.

Additionally, this invention comprises compounds of formula (II):

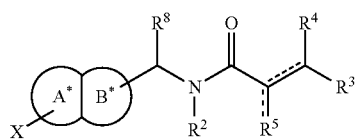

wherein:

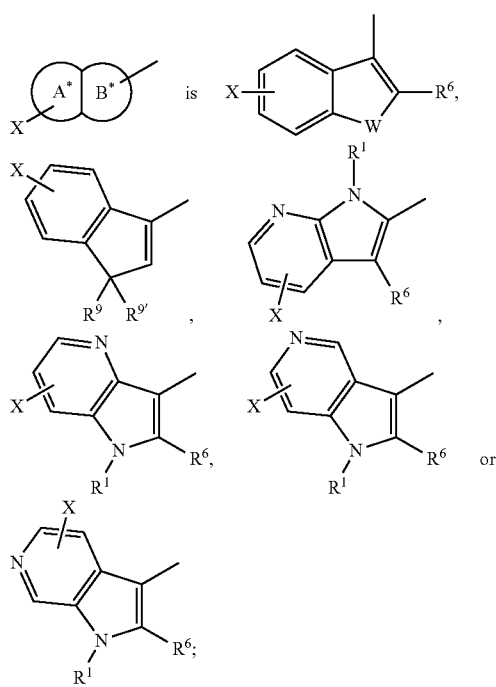

$R^1$ is H or $C_{1-4}$alkyl;
$R^2$ is H, $C_{1-4}$alkyl or $C_{3-6}$cycloalkyl;
$R^3$ is

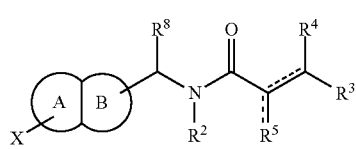

$R^4$ is H or $C_{1-4}$alkyl;

indicates that one of the two designated bonds is a double bond and the other is a single bond;

$R^5$ is $CH_2$ when the bond to which it is attached is a double bond; or $R^5$ is H or $C_{1-4}$alkyl when the bond to which it is attached is a single bond;

$R^6$ is H or $C_{1-4}$alkyl;
$R^7$ is H, $C_{1-4}$alkyl or $-C_{0-6}$alkyl-Ar;
Y is H, $C_{1-4}$alkyl, $N(R')_2$, NHC(O)R', $NHCH_2C(O)R'$ or NHC(O)CH=CHR';

each X independently is H, $C_{1-4}$alkyl, $CH_2OH$, OR', SR', CN, $N(R')_2$, $CH_2N(R')_2$, $NO_2$, $CF_3$, $CO_2R'$, $CON(R)_2$, COR', NR'C(O)R', F, Cl, Br, I or $-S(O)_rCF_3$;

W is S or O;
Q is H or $C_{1-4}$alkyl;
M is $CH_2$ or O;
L is $CH_2$ or C(O);
E is O or NR';

each R' independently is H, $C_{1-6}$alkyl or $-C_{0-6}$alkyl-Ar; and r is 0, 1 or 2;

or a pharmaceutically acceptable salt thereof.

Also, this invention comprises compounds of formula (III):

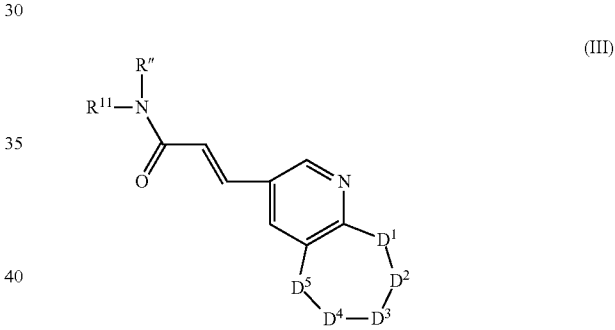

wherein:

$D^1$ to $D^5$ form an accessible substituted seven-membered ring, which may be saturated or unsaturated, optionally containing up to two heteroatoms chosen from the group of O, S and N wherein S and N may be optionally oxidized;

$R^{11}$ is $C_{1-6}$alkyl; and
R" is H or $C_{1-6}$alkyl;

or a pharmaceutically acceptable salt thereof.

This invention includes, but is not limited to, the following compounds:

(E)-3-(6-aminopyridin-3-yl)-N-(4,6-dichloro-1-methyl-1H-indol-2-ylmethyl)-N-methylacrylamide;
(E)-3-(2-aminopyrimidin-5-yl)-N-(2-methyl-1H-indol-3-yl-methyl)-N-methylacrylamide;
(E)-3-(6-aminopyridin-3-yl)-N-(1-ethyl-1H-indol-3-ylm-ethyl)-N-methylacrylamide;
(E)-3-(6-aminopyridin-3-yl)-N-(1-isopropyl-1H-indol-3-yl-methyl)-N-methylacrylamide;
(E)-N-methyl-N-(1-methyl-1H-indol-3-ylmethyl)-3-[6-(pyridin-2-ylamino)pyridin-3-yl]acrylamide;
(E)-3-(6-aminopyridin-3-yl)-N-(1,4-dimethyl-1H-indol-3-ylmethyl)-N-methylacrylamide;
(E)-3-(6-aminopyridin-3-yl)-N-(3,3-dimethyl-3H-indene-1-ylmethyl)-N-methylacrylamide;

(E)-3-(2-aminopyrimidin-5-yl)-N-methyl-N-(1-methyl-1H-pyrrolo[2,3-b]pyridin-3-ylmethyl)acrylamide;

(E)-N-methyl-N-(1-methyl-1H-pyrrolo[2,3-b]pyridin-3-ylmethyl)-3-(7-oxo-5,6,7,8-tetrahydro-1,8-naphthyridin-3-yl)acrylamide;

(E)-N-methyl-N-(2-methylbenzo[b]thiophen-3-ylmethyl)-3-(7-oxo-5,6,7,8-tetrahydro-1,8-naphthyridin-3-yl)acrylamide;

(E)-N-methyl-N-(2-methyl-1H-indol-3-ylmethyl)-3-(3-methyl-2-oxo-1,2,3,4-tetrahydropyrido[2,3-d]pyrimidin-6-yl)acrylamide;

(E)-3-(3H-imidazo[4,5-b]pyridin-6-yl)-N-methyl-N-(1-methyl-1H-indol-3-ylmethyl)acrylamide;

(E)-3-(3,4-dihydro-2H-pyrido[3,2-b]-1,4-oxazin-7-yl)-N-methyl-N-(1-methyl-1H-indol-3-ylmethyl)acrylamide;

(E)-N-(1H-indol-3-ylmethyl)-N-methyl-3-(7-oxo-5,6,7,8-tetrahydro-1,8-naphthyridin-3-yl)acrylamide;

(E)-3-(6-aminopyridin-3-yl)-N-(5-methoxy-1-methyl-1H-indol-3-ylmethyl)-N-methylacrylamide;

(E)-3-(6-aminopyridin-3-yl)-N-(4-methoxy-1-methyl-1H-indol-3-ylmethyl)-N-methylacrylamide;

(E)-3-(6-aminopyridin-3-yl)-N-(1H-indol-3-ylmethyl)-N-methylacrylamide (E)-3-(6-aminopyridin-3-yl)-N-(7-chloro-1-methyl-1H-indol-3-ylmethyl)-N-methylacrylamide;

(E)-N-methyl-N-(1-methyl-1H-indol-2-ylmethyl)-3-[6-[N-(methylaminocarbonylmethyl)amino]pyridin-3-yl]acrylamide;

(E)-3-(6-amino-5-(methoxycarbonyl)pyridin-3-yl)-N-(1-methyl-1H-indol-3-ylmethyl)-N-methylacrylamide;

(E)-N-(1-benzyl-1H-indol-3-ylmethyl)-N-methyl-3-(7-oxo-5,6,7,8-tetrahydro-1,8-naphthyridin-3-yl)acrylamide;

(E)-3-(6-aminopyridin-3-yl)-N-(7-methoxy-1-methyl-1H-indol-3-ylmethyl)-N-methylacrylamide;

(E)-N-methyl-N-(1-methyl-1H-indol-3-ylmethyl)-3-(3-methyl-2-oxo-1,2,3,4-tetrahydropyrido[2,3-d]pyrimidin-6-yl)acrylamide;

(E)-N-methyl-3-(7-oxo-5,6,7,8-tetrahydro-1,8-naphthyridin-3-yl)-N-(1,2,7-trimethyl-1H-indol-3-ylmethyl)acrylamide;

(E)-N-[1-(2-dimethylaminoethyl)-1H-indol-3-ylmethyl]-N-methyl-3-(7-oxo-5,6,7,8-tetrahydro-1,8-naphthyridin-3-yl)acrylamide;

(E)-N-(7-chloro-1-methyl-1H-indol-3-ylmethyl)-N-methyl-3-(7-oxo-5,6,7,8-tetrahydro-1,8-naphthyridin-3-yl)acrylamide;

(E)-3-[6-amino-5-[[N-methyl-N-(2-methyl-1H-indol-3-ylmethyl)amino]carbonylethyl]pyridin-3-yl]-N-methyl-N-(2-methyl-1H-indol-3-ylmethyl)acrylamide;

(E)-N-(2,3-dihydro-1H-3a-azacyclopenta[a]indene-8-ylmethyl)-N-methyl-3-(7-oxo-5,6,7,8-tetrahydro-1,8-naphthyridin-3-yl)acrylamide;

(E)-N-methyl-N-(2-methyl-1H-indol-3-ylmethyl)-3-(2-oxo-2,3-dihydro-1H-pyrrolo[2,3-b]pyridin-5-yl)acrylamide;

(E)-N-(1-ethyl-5-fluoro-1H-indol-3-ylmethyl)-N-methyl-3-(7-oxo-5,6,7,8-tetrahydro-1,8-naphthyridin-3-yl)acrylamide;

(E)-N-(7-chloro-1H-indol-3-ylmethyl)-N-methyl-3-(7-oxo-5,6,7,8-tetrahydro-1,8-naphthyridin-3-yl)acrylamide;

(E)-3-(6-aminopyridin-3-yl)-N-(6-chloro-1-methyl-1H-indol-3-ylmethyl)-N-methylacrylamide;

(E)-N-(5-fluoro-1-methyl-1H-indol-3-ylmethyl)-N-methyl-3-(7-oxo-5,6,7,8-tetrahydro-1,8-naphthyridin-3-yl)acrylamide;

(E)-N-(6-fluoro-1-methyl-1H-indol-3-ylmethyl)-N-methyl-3-(7-oxo-5,6,7,8-tetrahydro-1,8-naphthyridin-3-yl)acrylamide;

(E)-N-(7-fluoro-1-methyl-1H-indol-3-ylmethyl)-N-methyl-3-(7-oxo-5,6,7,8-tetrahydro-1,8-naphthyridin-3-yl)acrylamide;

(E)-3-(6-aminopyridin-3-yl)-N-(7-hydroxy-1-methyl-1H-indol-3-ylmethyl)-N-methylacrylamide;

(E)-3-(6-aminopyridin-3-yl)-N-(6-fluoro-1-methyl-1H-indol-3-ylmethyl)-N-methylacrylamide;

(E)-3-(6-aminopyridin-3-yl)-N-(5-chloro-1-methyl-1H-indol-3-ylmethyl)-N-methylacrylamide;

(E)-3-(6-aminopyridin-3-yl)-N-(4-chloro-1-methyl-1H-indol-3-ylmethyl)-N-methylacrylamide;

(E)-N-methyl-3-(8-oxo-6,7,8,9-tetrahydro-5H-pyrido[2,3-b]azepin-3-yl)acrylamide;

(E)-3-[6-[N-(methoxycarbonylmethyl)amino]pyridin-3-yl]-N-methyl-N-(2-methyl-1H-indol-3-ylmethyl)acrylamide;

(E)-3-[6-[N-(carboxymethyl)amino]pyridin-3-yl]-N-methyl-N-(2-methyl-1H-indol-3-ylmethyl)acrylamide;

(E)-N-methyl-N-(2-methyl-1H-indol-3-ylmethyl)-3-[6-[N-(methylaminocarbonylmethyl)amino]pyridin-3-yl]acrylamide;

(E)-N-(7-chloro-1-methyl-1H-indol-3-ylmethyl)-3-[6-[N-(methoxycarbonylmethyl)amino]pyridin-3-yl]-N-methylacrylamide;

(E)-2,N-dimethyl-N-(2-methyl-1H-indol-3-ylmethyl)-3-(7-oxo-5,6,7,8-tetrahydro-1,8-naphthyridin-3-yl)acrylamide;

(E)-3-[6-[N-(carboxymethyl)amino]pyridin-3-yl]-N-(7-chloro-1-methyl-1H-indol-3-ylmethyl)-N-methylacrylamide;

(E)-N-(7-chloro-1-methyl-1H-indol-3-ylmethyl)-N-methyl-3-[6-[N-(methylaminocarbonylmethyl)amino]pyridin-3-yl]acrylamide;

(E)-3,N-dimethyl-N-(2-methyl-1H-indol-3-ylmethyl)-3-(7-oxo-5,6,7,8-tetrahydro-1,8-naphthyridin-3-yl)acrylamide;

(E)-3-(6-aminopyridin-3-yl)-N-(4-fluoro-1-methyl-1H-indol-3-ylmethyl)-N-methylacrylamide;

(E)-3-(6-aminopyridin-3-yl)-N-(5-fluoro-1-methyl-1H-indol-3-ylmethyl)-N-methylacrylamide;

(E)-3-(6-aminopyridin-3-yl)-N-(7-fluoro-1-methyl-1H-indol-3-ylmethyl)-N-methylacrylamide;

(E)-3-(6-aminopyridin-3-yl)-N-(7-methoxycarbonyl-1-methyl-1H-indol-3-ylmethyl)-N-methylacrylamide;

(E)-3-(6-aminopyridin-3-yl)-N-(7-fluoro-1H-indol-3-ylmethyl)-N-methylacrylamide;

(E)-3-(6-aminopyridin-3-yl)-N-methyl-N-(1,2,7-trimethyl-1H-indol-3-ylmethyl)acrylamide;

(E)-N-methyl-N-(2-methyl-1H-indol-3-ylmethyl)-3-(8-oxo-6,7,8,9-tetrahydro-5H-pyrido[2,3-b]azepin-3-yl)acrylamide;

(E)-3-(6-aminopyridin-3-yl)-N-(7-chloro-1H-indol-3-ylmethyl)-N-methylacrylamide;

(E)-3-(6-aminopyridin-3-yl)-N-(2-chloro-1-methyl-1H-indol-3-ylmethyl)-N-methylacrylamide;

(E)-N-(2-chloro-1-methyl-1H-indol-3-ylmethyl)-N-methyl-3-(7-oxo-5,6,7,8-tetrahydro-1,8-naphthyridin-3-yl)acrylamide;

(E)-N-(5-chloro-1-methyl-1H-indol-3-ylmethyl)-N-methyl-3-(7-oxo-5,6,7,8-tetrahydro-1,8-naphthyridin-3-yl)acrylamide;

(E)-N-(4-fluoro-1-methyl-1H-indol-3-ylmethyl)-N-methyl-3-(7-oxo-5,6,7,8-tetrahydro-1,8-naphthyridin-3-yl)acrylamide;

(E)-N-(6-chloro-1-methyl-1H-indol-3-ylmethyl)-N-methyl-3-(7-oxo-5,6,7,8-tetrahydro-1,8-naphthyridin-3-yl)acrylamide;

(E)-3-(6-aminopyridin-3-yl)-N-(4-fluoro-1H-indol-3-ylmethyl)-N-methylacrylamide;
(E)-3-(6-aminopyridin-3-yl)-N-(7-carboxy-1-methyl-1H-indol-3-ylmethyl)-N-methylacrylamide;
(E)-N-(1,7-dimethyl-1H-indol-3-ylmethyl)-N-methyl-3-(7-oxo-5,6,7,8-tetrahydro-1,8-naphthyridin-3-yl)acrylamide;
(E)-N-(1,6-dimethyl-1H-indol-3-ylmethyl)-N-methyl-3-(7-oxo-5,6,7,8-tetrahydro-1,8-naphthyridin-3-yl)acrylamide;
(E)-N-(1,4-dimethyl-1H-indol-3-ylmethyl)-N-methyl-3-(7-oxo-5,6,7,8-tetrahydro-1,8-naphthyridin-3-yl)acrylamide;
(E)-N-(3,3-dimethyl-3H-indene-1-ylmethyl)-N-methyl-3-(7-oxo-5,6,7,8-tetrahydro-1,8-naphthyridin-3-yl)acrylamide;
(E)-N-(1,5-dimethyl-1H-indol-3-ylmethyl)-N-methyl-3-(7-oxo-5,6,7,8-tetrahydro-1,8-naphthyridin-3-yl)acrylamide;
(E)-N-(7-methoxy-1-methyl-1H-indol-3-ylmethyl)-N-methyl-3-(7-oxo-5,6,7,8-tetrahydro-1,8-naphthyridin-3-yl)acrylamide;
(E)-N-(7-hydroxy-1-methyl-1H-indol-3-ylmethyl)-N-methyl-3-(7-oxo-5,6,7,8-tetrahydro-1,8-naphthyridin-3-yl)acrylamide;
N-Methyl-N-(2-methyl-1H-indol-3-ylmethyl)-3-(4-methyl-3-oxo-2,3,4,5-tetrahydro-1H-pyrido[2,3-e]-1,4-diazepin-7-yl)acrylamide;
(E)-N-[1-(2-hydroxyethyl)-1H-indol-3-ylmethyl]-N-methyl-3-(7-oxo-5,6,7,8-tetrahydro-1,8-naphthyridin-3-yl)acrylamide;
(E)-N-(4-chloro-1-methyl-1H-indol-3-ylmethyl)-N-methyl-3-(7-oxo-5,6,7,8-tetrahydro-1,8-naphthyridin-3-yl)acrylamide;
(E)-N-methyl-N-(1-methyl-1H-indol-3-ylmethyl)-3-(8-oxo-6,7,8,9-tetrahydro-5H-pyrido[2,3-b]azepin-3-yl)acrylamide;
(E)-N-(4-methoxy-1-methyl-1H-indol-3-ylmethyl)-N-methyl-3-(7-oxo-5,6,7,8-tetrahydro-1,8-naphthyridin-3-yl)acrylamide;
(E)-N-(5-methoxy-1-methyl-1H-indol-3-ylmethyl)-N-methyl-3-(7-oxo-5,6,7,8-tetrahydro-1,8-naphthyridin-3-yl)acrylamide;
(E)-N-(6-methoxy-1-methyl-1H-indol-3-ylmethyl)-N-methyl-3-(7-oxo-5,6,7,8-tetrahydro-1,8-naphthyridin-3-yl)acrylamide;
(E)-N-(naphthalen-2-ylmethyl)-N-methyl-3-(7-oxo-5,6,7,8-tetrahydro-1,8-naphthyridin-3-yl)acrylamide;
(E)-N-(quinolin-3-ylmethyl)-N-methyl-3-(7-oxo-5,6,7,8-tetrahydro-1,8-naphthyridin-3-yl)acrylamide;
(E)-N-(1-methyl-1H-indol-3-ylmethyl)-N-methyl-3-(6-amino-7-oxo-5,6,7,8-tetrahydro-1,8-naphthyridin-3-yl)acrylamide;
(E)-N-(1-ethyl-1H-indol-3-ylmethyl)-N-methyl-3-(7-oxo-5,6,7,8-tetrahydro-1,8-naphthyridin-3-yl)acrylamide;
(E)-N-(naphthalen-1-ylmethyl)-N-methyl-3-(7-oxo-5,6,7,8-tetrahydro-1,8-naphthyridin-3-yl)acrylamide;
(E)-N-(benzofuran-2-ylmethyl)-N-methyl-3-(7-oxo-5,6,7,8-tetrahydro-1,8-naphthyridin-3-yl)acrylamide;
(E)-3-(6-aminopyridin-3-yl)-N-(6-methoxycarbonyl-1-methyl-1H-indol-3-ylmethyl)-N-methylacrylamide;
(E)-N-methyl-N-(2-methyl-1H-indol-3-ylmethyl)-3-[3-(2-methoxyethyl)-2-oxo-1,2,3,4-tetrahydropyrido[2,3-d]pyrimidin-6-yl]acrylamide;
(E)-N-(1-methyl-1H-indol-3-ylmethyl)-N-methyl-3-[6-(methoxycarbonyl)-7-oxo-5,6,7,8-tetrahydro-1,8-naphthyridin-3-yl]acrylamide;
(E)-3-(6-aminopyridin-3-yl)-N-(1,3-dimethyl-1H-pyrrolo[2,3-b]pyridin-3-ylmethyl)-N-methylacrylamide;
(E)-N-(1,3-dimethyl-1H-pyrrolo[2,3-b]pyridin-3-ylmethyl)-N-methyl-3-(7-oxo-5,6,7,8-tetrahydro-1,8-naphthyridin-3-yl)acrylamide;
(E)-3-(6-aminopyridin-3-yl)-N-methyl-N-(1-methyl-1H-pyrrolo[2,3-c]pyridin-3-ylmethyl)acrylamide;
(E)-3-(6-aminopyridin-3-yl)-N-methyl-N-(1-methyl-1H-pyrrolo[3,2-c]pyridin-3-ylmethyl)acrylamide;
(E)-3-(6-aminopyridin-3-yl)-N-methyl-N-(1-methyl-1H-pyrrolo[3,2-b]pyridin-3-ylmethyl)acrylamide;
(E)-N-methyl-N-(1-methyl-1H-pyrrolo[2,3-c]pyridin-3-ylmethyl)-3-(7-oxo-5,6,7,8-tetrahydro-1,8-naphthyridin-3-yl)acrylamide;
(E)-N-methyl-N-(1-methyl-1H-pyrrolo[3,2-c]pyridin-3-ylmethyl)-3-(7-oxo-5,6,7,8-tetrahydro-1,8-naphthyridin-3-yl)acrylamide;
(E)-N-methyl-N-(1-methyl-1H-pyrrolo[3,2-b]pyridin-3-ylmethyl)-3-(7-oxo-5,6,7,8-tetrahydro-1,8-naphthyridin-3-yl)acrylamide;
(E)-3-(6-aminopyridin-3-yl)-N-(benzofuran-3-ylmethyl)-N-methylacrylamide;
(E)-3-(6-aminopyridin-3-yl)-N-methyl-N-(3-methylbenzofuran-2-ylmethyl)acrylamide;
(E)-3-(6-aminopyridin-3-yl)-N-methyl-N-(2-methylbenzofuran-3-ylmethyl)acrylamide;
(E)-N-(benzofuran-3-ylmethyl)-N-methyl-3-(7-oxo-5,6,7,8-tetrahydro-1,8-naphthyridin-3-yl)acrylamide;
(E)-N-methyl-N-(3-methylbenzofuran-2-ylmethyl)-3-(7-oxo-5,6,7,8-tetrahydro-1,8-naphthyridin-3-yl)acrylamide;
(E)-N-methyl-N-(2-methylbenzofuran-3-ylmethyl)-3-(7-oxo-5,6,7,8-tetrahydro-1,8-naphthyridin-3-yl)acrylamide;
(E)-(6-aminopyridin-3-yl)-N-methyl-N-[1-(1-methyl-1H-indol-2-yl)ethyl]acrylamide;
(E)-(6-aminopyridin-3-yl)-N-methyl-N-[1-(1-methyl-1H-indol-3-yl)ethyl]acrylamide;
(E)-N-methyl-N-[1-(1-methyl-1H-indol-2-yl)ethyl]-3-(7-oxo-5,6,7,8-tetrahydro-1,8-naphthyridin-3-yl)acrylamide; and
(E)-N-methyl-N-[1-(1-methyl-1H-indol-3-yl)ethyl]-3-(7-oxo-5,6,7,8-tetrahydro-1,8-naphthyridin-3-yl)acrylamide;
or a pharmaceutically acceptable salt thereof.

Also included in this invention are pharmaceutically acceptable addition salts and complexes of the compounds of this invention. In cases wherein the compounds of this invention may have one or more chiral centers, unless specified, this invention includes each unique racemic compound, as well as each unique nonracemic compound.

In cases in which compounds have unsaturated carbon-carbon double bonds, both the cis (Z) and trans (E) isomers are within the scope of this invention. In cases wherein compounds may exist in tautomeric forms, such as keto-enol tautomers, such as

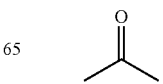

and

each tautomeric form is contemplated as being included within this invention, whether existing in equilibrium or locked in one form by appropriate substitution with R'. The meaning of any substituent at any one occurrence is independent of its meaning, or any other substituent's meaning, at any other occurrence.

Also included in this invention are prodrugs of the compounds of this invention. Prodrugs are considered to be any covalently bonded carriers which release the active parent drug in vivo.

The compounds of this invention inhibit Fab I. Inhibition of this enzyme is useful in the treatment of bacterial infections. Also, the compounds of this invention may be useful as antifungal agents. Additionally, the compounds may be useful in combination with known antibiotics.

Abbreviations and symbols commonly used in the peptide and chemical arts are used herein to describe the compounds of this invention.

$C_{1-4}$alkyl as applied herein means an optionally substituted alkyl group of 1 to 4 carbon atoms, and includes methyl, ethyl, n-propyl, isopropyl, n-butyl, isobutyl and t-butyl. $C_{1-6}$alkyl additionally includes pentyl, n-pentyl, isopentyl, neopentyl and hexyl and the simple aliphatic isomers thereof. $C_{0-4}$alkyl and $C_{0-6}$alkyl additionally indicates that no alkyl group need be present (e.g., that a covalent bond is present).

Any $C_{1-4}$alkyl or $C_{1-6}$ alkyl may be optionally substituted with the group $R^x$, which may be on any carbon atom that results in a stable structure and is available by conventional synthetic techniques. Suitable groups for $R^x$ are $C_{1-4}$alkyl, OR', SR', CN, N(R')$_2$, CH$_2$N(R')$_2$, —NO$_2$, —CF$_3$, —CO$_2$R'—CON(R')$_2$, —COR', —NR'C(O)R', F, Cl, Br, I, or —S(O)$_r$CF$_3$, wherein R' and r are as defined for formula (I) compounds.

Halogen or halo means F, Cl, Br, and I.

Ar, or aryl, as applied herein, means phenyl or naphthyl, or phenyl or naphthyl substituted by one to three substituents, such as those defined above for alkyl, or substituted by methylenedioxy.

Het, or heterocycle, indicates an optionally substituted five or six membered monocyclic ring, or a nine or ten-membered bicyclic ring containing one to three heteroatoms chosen from the group of nitrogen, oxygen and sulfur, which are stable and available by conventional chemical synthesis. Illustrative heterocycles are benzofuryl, benzimidazolyl, benzopyranyl, benzothienyl, furyl, imidazolyl, indolinyl, morpholinyl, piperidinyl, piperazinyl, pyrrolyl, pyrrolidinyl, tetrahydropyridinyl, pyridinyl, thiazolyl, thienyl, quinolinyl, isoquinolinyl, and tetra- and perhydro- quinolinyl and isoquinolinyl. Any accessible combination of up to three substituents on the Het ring, such as those defined above for alkyl, that are available by chemical synthesis and are stable are within the scope of this invention.

Certain radical groups are abbreviated herein. t-Bu refers to the tertiary butyl radical, Boc refers to the t-butyloxycarbonyl radical, Fmoc refers to the fluorenylmethoxycarbonyl radical, Ph refers to the phenyl radical, Cbz refers to the benzyloxycarbonyl radical, Bn refers to the benzyl radical, Me refers to methyl, Et refers to ethyl, Ac refers to acetyl, Alk refers to $C_{1-4}$alkyl, Nph refers to 1- or 2-naphthyl and cHex refers to cyclohexyl. Tet refers to 5-tetrazolyl.

Certain reagents are abbreviated herein. DCC refers to dicyclohexylcarbodiimide, DMAP refers to dimethylaminopyridine, EDC refers to 1-(3-dimethylaminopropyl)-3-ethylcarbodiimide, hydrochloride, HOBt refers to 1-hydroxybenzotriazole, THF refers to tetrahydrofuran, DIEA refers to diisopropylethylamine, DEAD refers to diethyl azodicarboxylate, PPh$_3$ refers to triphenylphosphine, DIAD refers to diisopropyl azodicarboxylate, DME refers to dimethoxyethane, DMF refers to dimethylformamide, NBS refers to N-bromosuccinimide, Pd/C refers to a palladium on carbon catalyst, PPA refers to polyphosphoric acid, DPPA refers to diphenylphosphoryl azide, BOP refers to benzotriazol-1-yloxy-tris(dimethyl-amino)phosphonium hexafluorophosphate, HF refers to hydrofluoric acid, TEA refers to triethylamine, TFA refers to trifluoroacetic acid, PCC refers to pyridinium chlorochromate.

In particular, compounds of this invention are prepared by the general methods described in the Schemes hereinafter.

Scheme I

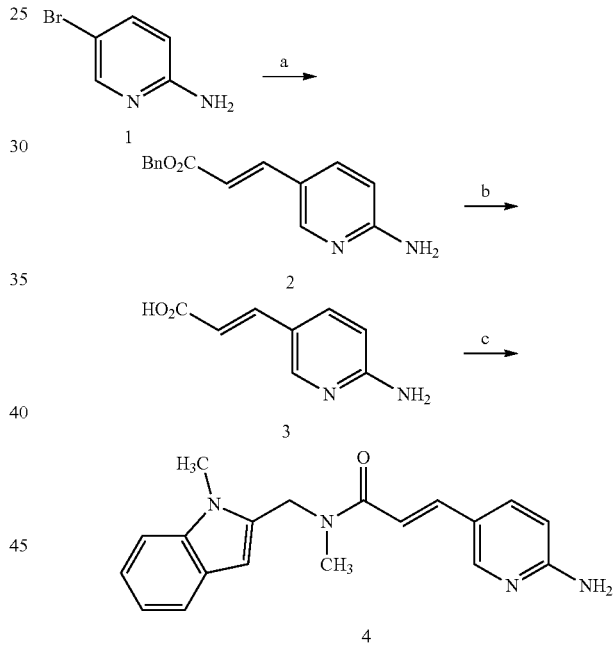

(a) benzyl acrylate, Pd(OAc)$_2$, P(o-tol)$_3$, (i-Pr)$_2$NEt, propionitrile; (b) 1.0N NaOH, MeOH; (c) 1-methyl-2-(methylaminomethyl)indole, EDC, HOBt•H$_2$O, Et$_3$N, DMF.

A suitable haloaromatic derivative, for instance 2-amino-5-bromopyridine (I-1), reacts with an appropriate α,β-unsaturated ester, for example benzyl acrylate, in a Heck-type reaction (see Heck, *Org. Reactions* 1982, 27, 345) to afford I-2. The reaction is mediated by a palladium(0) species, and generally is conducted in an inert solvent, such as CH$_3$CN, propionitrile, or toluene, in the presence of an appropriate acid scavenger, such as triethylamine (Et$_3$N) or diisopropylethylamine ((i-Pr)$_2$NEt). Typical sources of the palladium(0) species include palladium (II) acetate (Pd(OAc)$_2$) and palladium(II) chloride (PdCl$_2$), and oftentimes phosphine ligands, for instance triphenylphosphine (PPh$_3$) or tri-ortho-tolylphosphine (P(tol)$_3$), are included. The ethyl ester of I-2 is hydrolyzed using aqueous base, for example, LiOH in aqueous THF or NaOH in aqueous methanol or ethanol, and the intermediate carboxylate salt is acidified with a suitable acid, for instance TFA or HCl, to afford the carboxylic acid I-3. The carboxylic acid of I-3 is converted to an activated form using, for example, EDC and HOBt, or SOCl$_2$, and the activated form is subsequently reacted with an appropriate amine, for instance 1-methyl-2-(methylaminomethyl)indole, in a suitable solvent such as DMF, CH$_2$Cl$_2$, or CH$_3$CN, to afford I-4. Depending on whether acid neutralization is required, an added base, such as triethylamine (Et$_3$N), diisopropylethylamine ((i-Pr)$_2$NEt), or pyridine, may be used. Many additional methods for converting a carboxylic acid to an amide are known, and can be found in standard reference books, such as "Compendium of Organic Synthetic Methods", Vol. I-VI (published by Wiley-Interscience), or Bodansky, "The Practice of Peptide Synthesis" (published by Springer-Verlag).

typically with an alkali metal hydroxide such as LiOH, NaOH, or KOH, in an aqueous solvent, such as THF, ethanol, or methanol, and the resulting carboxylic acid can be converted to the desired amide. Typical methods for forming amides are described in Scheme I. Reduction of the amide II-3 to the amine II-4 is typically accomplished with lithium aluminum hydride LiAlH$_4$ in refluxing THF, although many other methods can be used to reduce amides to amines. Such methods are well-known to those of skill in the art, and can be found in standard reference volumes, such as "Compendium of Organic Synthetic Methods" (published by Wiley-Interscience).

Scheme III

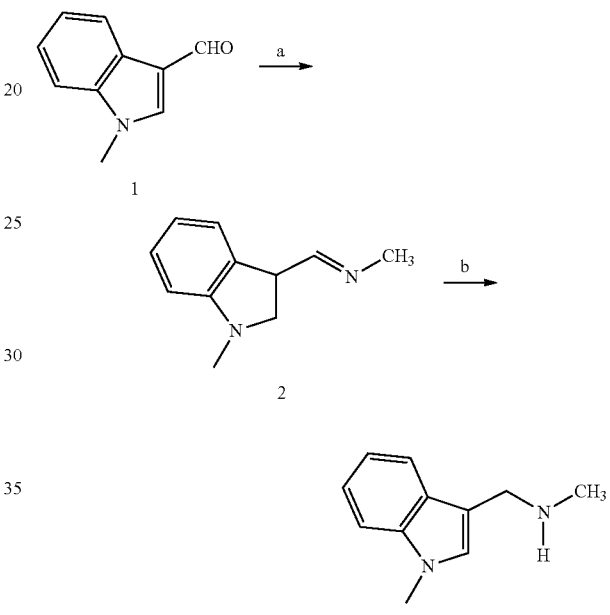

(a) CH$_3$NH$_2$, MeOH; (b) NaBH$_4$, EtOH.

Scheme II

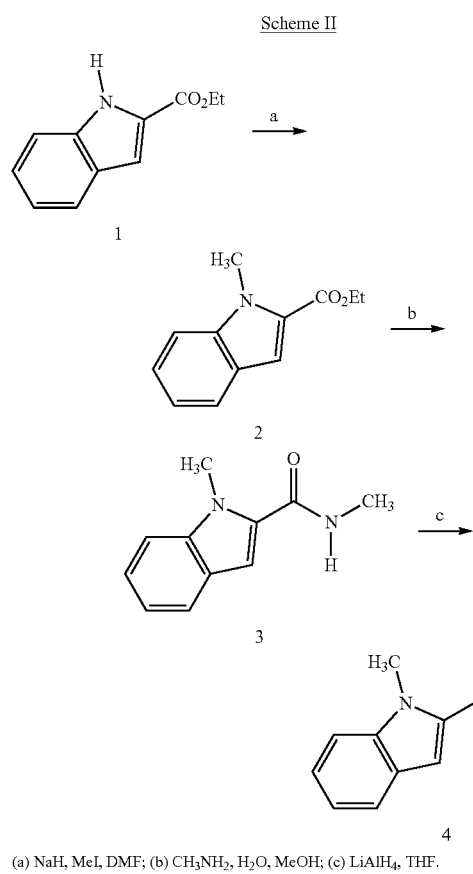

(a) NaH, MeI, DMF; (b) CH$_3$NH$_2$, H$_2$O, MeOH; (c) LiAlH$_4$, THF.

The amine coupling partners used in the present invention were prepared by established methods well-known to those of skill in the art. For example, amine II-4 is prepared by the straightforward procedure outlined in Scheme II. Commercially available ethyl indole-2-carboxylate (II-1) is deprotonated with a suitable base, generally sodium hydride (NaH), and the intermediate sodium salt is reacted with an appropriate alkylating agent, for instance methyl iodide, to afford II-2. Polar solvents such as DMF, THF, or mixtures thereof are generally preferred for this reaction. Compound II-2 can be conveniently converted to II-3 by reaction with an excess of an amine, such as methylamine, in a polar solvent, generally H$_2$O or a mixture of H$_2$O and methanol. Alternatively, the ester of II-2 can be saponified under standard conditions, The amine coupling partners used in the present invention can also be prepared by the reductive amination of an appropriate aldehyde (Scheme III). This method, which is well-known to those of skill in the art, involves the initial conversion of an aldehyde to an intermediate imine, which is subsequently reduced, oftentimes in situ, to afford the amine For example, the commercially-available aldehyde III-1 reacts with an appropriate amine, for instance methylamine, in a suitable solvent, typically methanol, to afford the imine III-2. Reaction of III-2 with a suitable reducing agent, for example sodium borohydride, sodium cyanoborohydride or sodium (triacetoxy)borohydride, gives the amine III-3.

Scheme IV

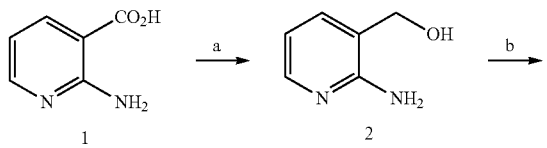

-continued

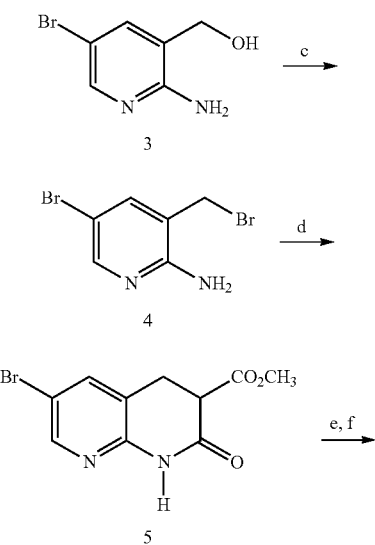

(a) LiAlH₄, THF; (b) Br₂, AcOH; (c) 48% HBr; (d) (MeO₂C)₂CH₂, NaH, DMF, THF; (e) NaOH, H₂O, MeOH; (f) HCl, H₂O, MeOH; (g) acryloyl chloride, Et₃N, CH₂Cl₂; (h) Pd(OAc)₂, P(o-tol)₃, (i-Pr)₂NEt, propionitrile.

Commercially available 2-aminonicotinic acid (IV-1) is reduced to alcohol IV-2 under standard conditions (LiAlH₄, THF), and the aromatic ring of IV-2 is brominated using, for example, bromine or N-bromosuccinimide (NBS), in a suitable solvent such as CH₂Cl₂, acetic acid (AcOH), or mixtures thereof, to afford IV-3. On reaction with 48% aqueous HBr, IV-3 is converted to bromide IV-4, which reacts with a diester of malonic acid, for instance dimethyl malonate, under basic conditions, to afford the naphthyridone derivative IV-5. Typical basic conditions include an alkali metal hydride, for instance sodium hydride, in a neutral solvent such as DMF, THF, or mixtures thereof, or an alkali metal alkoxide, such as sodium methoxide or sodium ethoxide, in an alcoholic solvent such as with methanol or ethanol. Saponification and neutralization under standard conditions affords an intermediate carboxylic acid (not shown), which is typically not isolated, but is subject to decarboxylation on gentle warming to afford the naphthyridone IV-6. This compound reacts with acrylamide IV-8 in a Heck-type reaction as described in Scheme I to afford IV-9. Alternatively, IV-6 might be converted to IV-9 according to the general procedure described in Scheme I for the conversion of I-1 to I-4. The acrylamide IV-8 is conveniently prepared by reaction of amine IV-7 (see Scheme I) with an activated form of acrylic acid in an amide bond-forming reaction. Typical conditions for the formation of amides are described in Scheme I, and are well-known to those of skill in the art.

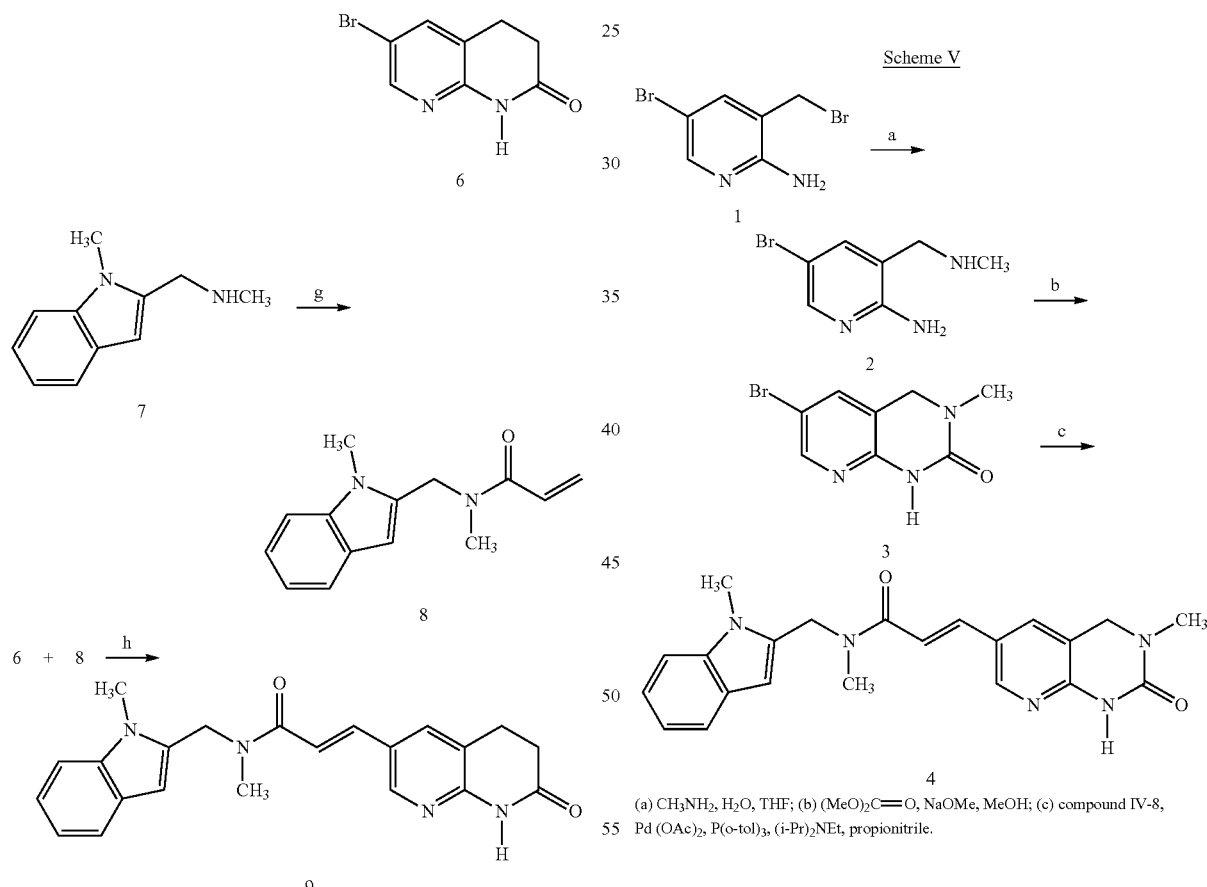

(a) CH₃NH₂, H₂O, THF; (b) (MeO)₂C═O, NaOMe, MeOH; (c) compound IV-8, Pd(OAc)₂, P(o-tol)₃, (i-Pr)₂NEt, propionitrile.

Benzylic bromide V-1, prepared as described in Scheme IV, reacts with an amine, for example aqueous methylamine, to afford benzylic amine V-2. Polar solvents such as THF, DMF, DMSO, or mixture thereof, are generally preferred for this reaction. V-2 reacts with a dialkyl carbonate, preferably dimethyl carbonate, in the presence of a suitable base, typically sodium methoxide, in an alcoholic solvent, generally methanol, to afford the cyclic urea derivative V-3. This compound is converted to V-4 by reaction with compound IV-8 as described in Scheme IV.

Scheme VI

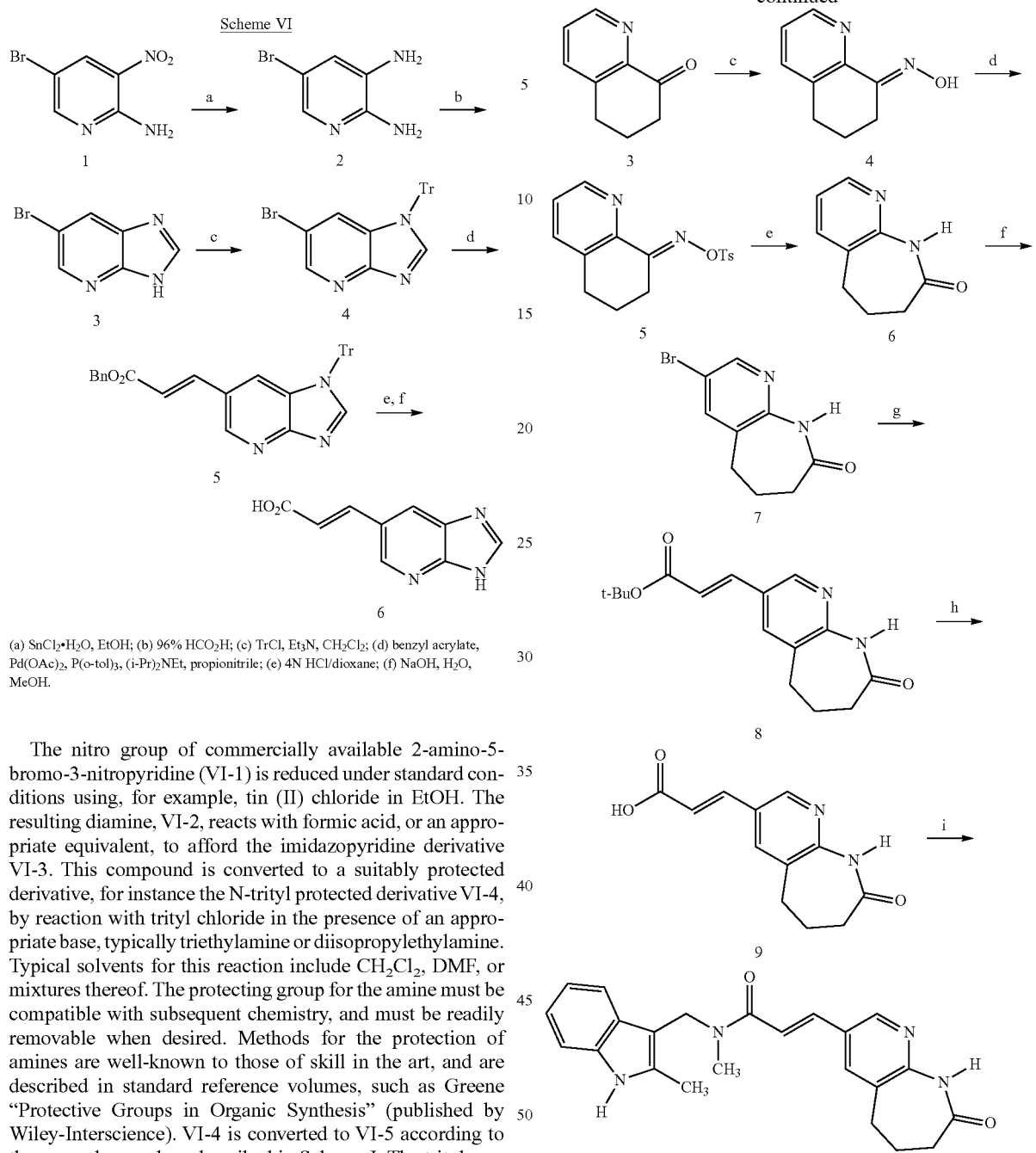

(a) SnCl₂•H₂O, EtOH; (b) 96% HCO₂H; (c) TrCl, Et₃N, CH₂Cl₂; (d) benzyl acrylate, Pd(OAc)₂, P(o-tol)₃, (i-Pr)₂NEt, propionitrile; (e) 4N HCl/dioxane; (f) NaOH, H₂O, MeOH.

The nitro group of commercially available 2-amino-5-bromo-3-nitropyridine (VI-1) is reduced under standard conditions using, for example, tin (II) chloride in EtOH. The resulting diamine, VI-2, reacts with formic acid, or an appropriate equivalent, to afford the imidazopyridine derivative VI-3. This compound is converted to a suitably protected derivative, for instance the N-trityl protected derivative VI-4, by reaction with trityl chloride in the presence of an appropriate base, typically triethylamine or diisopropylethylamine. Typical solvents for this reaction include CH₂Cl₂, DMF, or mixtures thereof. The protecting group for the amine must be compatible with subsequent chemistry, and must be readily removable when desired. Methods for the protection of amines are well-known to those of skill in the art, and are described in standard reference volumes, such as Greene "Protective Groups in Organic Synthesis" (published by Wiley-Interscience). VI-4 is converted to VI-5 according to the general procedure described in Scheme I. The trityl protecting group is removed under standard acidic conditions (see Greene above), and the ester is saponified as in Scheme I to afford VI-6.

Scheme VII

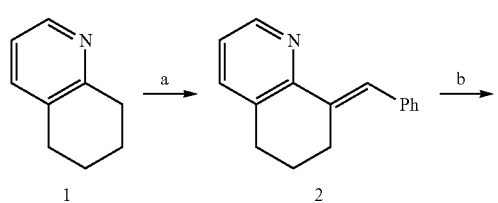

(a) PhCHO, Ac₂O; (b) O₃, CH₂Cl₂, then DMS; (c) H₂NOH•HCl, (i-Pr)₂NEt, EtOH; (d) p-TsCl, KOH, acetone, H₂O; (e) KOAc, EtOH, H₂O; (f) Br₂, CH₂Cl₂; (g) tert-butyl acrylate, Pd(OAc)₂, P(o-tol)₃, (i-Pr)₂NEt, propionitrile; (h) 4.0N HCl/dioxane; (i) 2-methyl-3-(methylaminomethyl)indole, EDC, HOBt•H₂O, (i-Pr)₂NEt, DMF.

Commercially-available tetrahydroquinoline (VII-1) is condensed with an appropriate aldehyde, typically benzaldehyde (PhCHO), under standard conditions to afford the olefinic derivative VII-2. Oxidative cleavage of the exocyclic olefin affords ketone VII-3. Generally, ozonolysis in a neutral solvent, such as methylene chloride (CH₂Cl₂), methanol (MeOH), or mixtures thereof, followed by in situ reduction of the intermediate ozonide with an appropriate reducing agent, usually dimethylsulfide, is the method of choice for this transformation. Compound VII-3 is converted to the 7-membered lactam derivative VII-6 as described by Jössang-Yanagida and Gansser (*J. Het. Chem.* 1978, 15, 249-251). This procedure involves conversion of the ketone of VII-3 to the corresponding oxime VII-4, which is subsequently converted to the O-tosyl derivative VII-5. A Beckmann-type rearrangement of VII-5 affords the lactam VII-6. Bromination of VII-6 with a suitable brominating agent, such as bromine (Br$_2$) or N-bromosuccinimide (NBS), affords the bromo derivative VII-7. Typical solvents for a bromination reaction include CH$_2$Cl$_2$, CCl$_4$, MeOH, AcOH, or mixtures thereof. Bromide VII-7 reacts with an appropriate α,β-unsaturated ester, for example tert-butyl acrylate, in a Heck-type reaction as described in Scheme I to afford VII-8. The tert-butyl ester of VII-8 is cleaved to the corresponding carboxylic acid VII-9 under standard acidic conditions. Typical conditions for this transformation are described in standard reference volumes, such as Greene "Protective Groups in Organic Synthesis" (published by Wiley-Interscience). VII-9 is converted to VII-10 by the general method described in Scheme I.

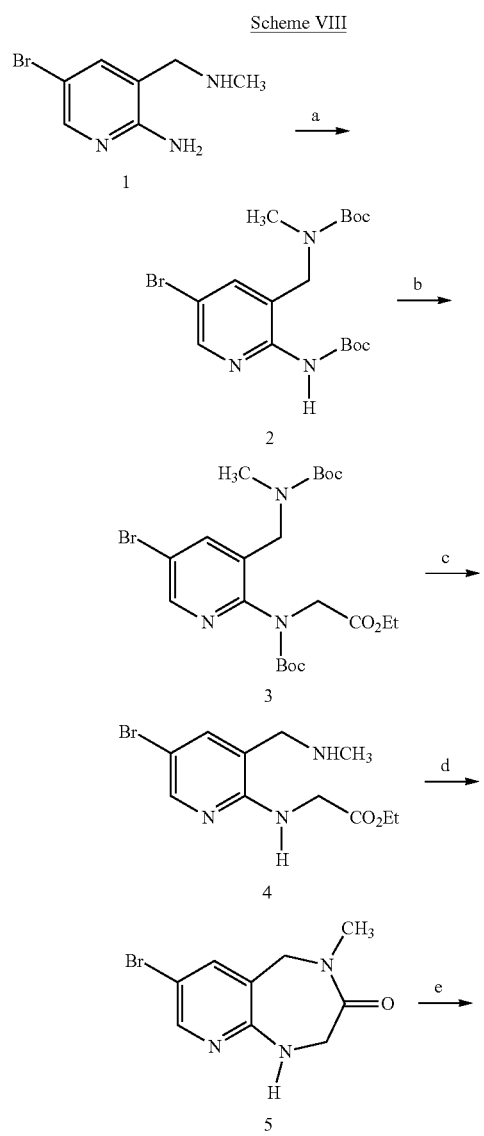

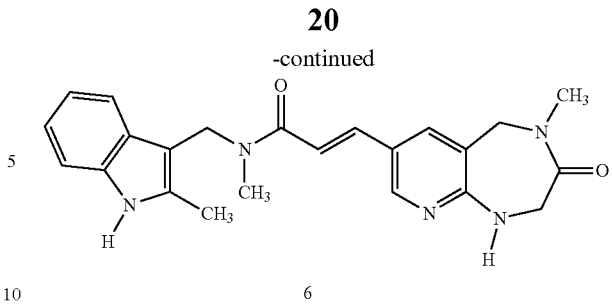

(a) (Boc)$_2$O, THF; (b) NaH, ethyl bromoacetate, THF; (c) TFA, CH$_2$Cl$_2$; (d) Et$_3$N, toluene; (e) N-methyl-N-(2-methyl-1H-indol-3-ylmethyl)acrylamide, Pd(OAc)$_2$, P(o-tol)$_3$, (i-Pr)$_2$NEt, propionitrile.

Compound VIII-1, prepared as described in Scheme V, reacts with two equivalents of an appropriate acylating agent, preferably di-tert-butyl dicarbonate, to afford VIII-2. As discussed in Scheme VI, the protecting group for the amines must be compatible with subsequent chemistry, and must be readily removable when desired. VIII-2 is deprotonated with a suitable base, generally sodium hydride (NaH), and the intermediate sodium salt is reacted with an appropriate alkylating agent, for instance ethyl bromoacetate, to afford VIII-3. Polar solvents such as DMF, THF, or mixtures thereof are generally preferred for this reaction. The Boc protecting groups are removed under standard acidic conditions (see Greene above) to afford VIII-4, which undergoes cyclization to compound VIII-5 on exposure to a suitable base, typically triethylamine (Et$_3$N) or diisopropylethylamine ((i-Pr)$_2$NEt). An inert solvent, such as toluene, is preferred. VIII-5 is converted to VIII-6 by the general method described in Scheme IV.

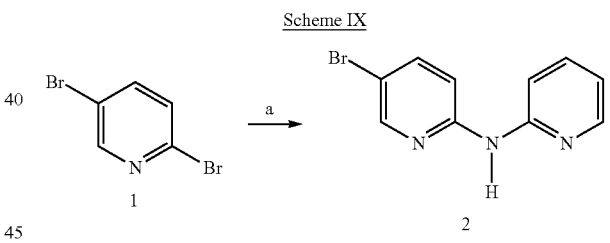

(a) 2-aminopyridine, sodium tert-butoxide, tris(dibenzylideneacetone)dipalladium(0), 1,3-bis(diphenylphosphino)propane, toluene.

Commercially available 2,5-dibromopyridine (IX-1) reacts with 2-aminopyridine in the presence of a suitable base, typically sodium tert-butoxide, to afford the dipyridylamine derivative IX-2. The reaction is mediated by a suitable palladium (0) catalyst, such as tris(dibenzylideneacetone)dipalladium(0), in the presence of an appropriate ligand, for example 1,3-bis(diphenylphosphino)propane. A neutral solvent such as toluene is preferred.

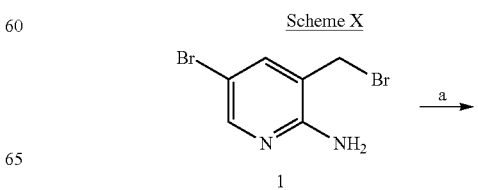

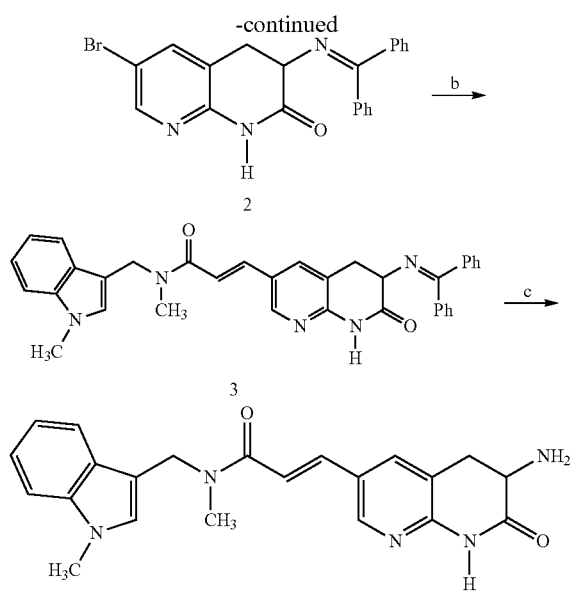

(a) N-(Diphenylmethylene)glycine ethyl ester, NaH, DMF; (b) N-methyl-N-(1-methyl-1H-indol-3-ylmethyl)acrylamide, Pd(OAc)$_2$, P(o-tol)$_3$, (i-Pr)$_2$NEt, propionitrile; (c) HCl, dioxane, H$_2$O.

Benzylic bromide V-1, prepared as described in Scheme IV, reacts with an appropriate α-aminoester equivalent, for example N-(diphenylmethylene)glycine ethyl ester, under basic conditions, to provide X-2. A polar, aprotic solvent, such as DMF, THF, DME, or mixtures thereof, is generally preferred, and sodium hydride is typically the base of choice, although LDA or LiN(TMS)$_2$ might also be used. Alternatively, the reaction might be conducted in an alcoholic solvent, such as methanol or ethanol, with an alkali metal alkoxide, for example sodium methoxide or sodium ethoxide, as the base. The diphenylmethylene group is conveniently removed under acidic conditions, such as HCl in aqueous dioxane. Other conditions for the removal of a diphenylmethylene group are known to those of skill in the art, and can be found in the chemical literature or in standard reference volumes, such as Greene (see above).

Acid addition salts of the compounds are prepared in a standard manner in a suitable solvent from the parent compound and an excess of an acid, such as hydrochloric, hydrobromic, hydrofluoric, sulfuric, phosphoric, acetic, trifluoroacetic, maleic, succinic or methanesulfonic. Certain of the compounds form inner salts or zwitterions which may be acceptable. Cationic salts are prepared by treating the parent compound with an excess of an alkaline reagent, such as a hydroxide, carbonate or alkoxide, containing the appropriate cation; or with an appropriate organic amine Cations such as Li$^+$, Na$^+$, K$^+$, Ca$^{++}$, Mg$^{++}$ and NH$_4^+$ are specific examples of cations present in pharmaceutically acceptable salts.

This invention also provides a pharmaceutical composition which comprises a compound according to the instant invention and a pharmaceutically acceptable carrier. Accordingly, the compounds of the present invention may be used in the manufacture of a medicament. Pharmaceutical compositions of the compounds of this invention prepared as hereinbefore described may be formulated as solutions or lyophilized powders for parenteral administration. Powders may be reconstituted by addition of a suitable diluent or other pharmaceutically acceptable carrier prior to use. The liquid formulation may be a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride or sodium citrate.

Alternately, these compounds may be encapsulated, tableted or prepared in a emulsion or syrup for oral administration. Pharmaceutically acceptable solid or liquid carriers may be added to enhance or stabilize the composition, or to facilitate preparation of the composition. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

For rectal administration, the compounds of this invention may also be combined with excipients, such as cocoa butter, glycerin, gelatin or polyethylene glycols, and molded into a suppository.

For topical administration, the compounds of this invention may be combined with diluents to take the form of ointments, gels, pastes, creams, powders or sprays. The compositions which are ointments, gels, pastes or creams contain diluents, for example, animal and vegetable fats, waxes, paraffins, starch, tragacanth, cellulose derivatives, polyethylene glycols, silicones, bentonites, silicic acid, talc and zinc oxide, or mixtures of these substances. The compositions which are powders or sprays contain diluents, for example, lactose, talc, silicic acid, aluminum hydroxide, calcium silicate and polyamide powder, or mixtures of these substances. Additionally, for topical ophthalmologic administration, the typical carriers are water, mixtures of water and water miscible solvents, such as lower alkanols or vegetable oils, and water-soluble non-toxic polymers, for example cellulose derivatives, such as methyl cellulose.

The compounds described herein are inhibitors of Fab I, and are useful for treating bacterial infections. For instance, these compounds are useful for the treatment of bacterial infections, such as, for example, infections of upper respiratory tract (e.g. otitis media, bacterial tracheitis, acute epiglottitis, thyroiditis), lower respiratory (e.g. empyema, lung abscess), cardiac (e.g. infective endocarditis), gastrointestinal (e.g. secretory diarrhoea, splenic abscess, retroperitoneal abscess), CNS (e.g. cerebral abscess), eye (e.g. blepharitis, conjunctivitis, keratitis, endophthalmitis, preseptal and orbital cellulitis, darcryocystitis), kidney and urinary tract (e.g. epididymitis, intrarenal and perinephric abscess, toxic shock syndrome), skin (e.g. impetigo, folliculitis, cutaneous abscesses, cellulitis, wound infection, bacterial myositis), and bone and joint (e.g. septic arthritis, osteomyelitis). Also, the compounds of this invention may be useful as antifungal agents. Additionally, the compounds may be useful in combination with known antibiotics.

The compounds of this invention are administered to the patient, in a manner such that the concentration of drug is sufficient to treat bacterial infections. The pharmaceutical composition containing the compound is administered at an oral dose of between about 10 mg to about 1000 mg, taken once or several times daily, in a manner consistent with the condition of the patient. Preferably, the oral dose would be about 50 mg to about 500 mg, although the dose may be varied depending upon the age, body weight and symptoms of the patient. For acute therapy, parenteral administration is preferred. An intravenous infusion of the compound of formula (I) in 5% dextrose in water or normal saline, or a similar formulation with suitable excipients, is most effective, although an intramuscular bolus injection is also useful. The precise level and method by which the compounds are administered is readily determined by one skilled in the art.

The compounds may be tested in one of several biological assays to determine the concentration of compound which is required to have a given pharmacological effect.

Cloning of S. aureus FabI:

The fabI gene was cloned from the chromosomal DNA of S. aureus strain WCUH29 using the polymerase chain reaction. Amplification was performed using Taq DNA polymerase (BRL) and the following primers: 5'-CGC CTCGAGATGTTAAATCTTGAAAACAAAACATATGTC-3' (SEQ ID NO: 1) and 5'-CGC GGATCCAATCAAGTCAGGTTGAAATATCCA-3' (SEQ ID NO: 2) (XhoI and BamHI sites underlined). The resulting fragment was then digested with XhoI and BamHI and ligated into XhoI- and BamHI-digested expression vector pET-16b (Novagen), producing pET-His$_{10}$-fabI. The gene sequence of fabI was confirmed by automated cycle sequencing using an Applied Biosystems model 377 machine. The untagged version of pET-fabI was constructed by digesting pET-His$_{10}$-fabI with NcoI and NdeI to remove a 97 bp fragment encoding the His 10 tag, the factor Xa cleavage site and the first 8 amino acids of FabI, and replacing it with a linker encoding the first 8 amino acids of FabI plus a glycine residue between the initiator methionine and the lysine at position 2. This plasmid was called pET-fabI. The linker was made by annealing the following two oligonucleotides: 5'-CATGGGCTTAAATCT-TGAAAACAAAACA-3'(SEQ ID NO: 3) and 5'-TAT-GTTTTGTTTTCAAGATTTAAGCC-3' (SEQ ID NO: 4). The linker sequence in pET-fabI was confirmed by dideoxy sequencing. Only native FabI was used for compound evaluation. For overproduction of native FabI, plasmid pET-fabI was transformed into BL21(DE3) (Novagen) cells, to form strain BL21(DE3):pET-fabI.

Purification of S. aureus FabI

S. aureus FabI was expressed as soluble protein to 10% of total cell protein, 400 g cells being recovered from 15 L fermentation in tryptone phosphate medium. The cells were lysed and the sample centrifuged. The resulting supernatant was filtered and purified using three consecutive chromatography columns: ion-exchange (Sourse 15Q), dye-affinity (Blue sepharose), and size exclusion chromatography columns (Superose 12). After each column the FabI containing fractions were pooled, concentrated, and checked for purity and biological activity.

Cloning/Expression Haemophilus influenzae FabI

The FabI gene was PCR amplified from Haemophilus influenzae (Q1) genomic DNA. Oligonucleotide primers were designed with unique restriction sites at both the N' and C' terminal ends of the gene to allow efficient sub-cloning into the expression vector pPROLar.

```
FORWARD PRIMER
                                            (SEQ ID NO: 5)
     KpnI
5' GCGGTACCCATGCGCTTGGTTTTCTTAGAAATATTG '3

REVERSE PRIMER
                                            (SEQ ID NO: 6)
     NotI
5' GCGGCCGCTTATTCTTCGCCTAATTCGCCCATTGC '3
```

PCR amplification was performed using Pfu Turbo DNA polymerase as per the instructions of the manufacturer (Stratagene). The following cycling conditions were used: 95° C. for 3 minutes followed by 30 cycles of 94° C. 1 minute, 55° C. 1 minute and 72° C. 3 minutes. A final extension at 72° C. for 5 minutes was carried out. PCR products of expected size for Haemophilus influenzae FabI were cloned into the PCR cloning vector TOPO TA 2.1 as per instructions of the manufacturer (Invitrogen). The fidelity of the presumptive PCR amplified Haemophilus influenzae FabI gene was confirmed by DNA sequencing on both strands using an ABI 377 Automative DNA Sequencer (Applied Biosystems). pPROLar was digested with KpnI and NotI restriction endonucleases using conditions as recommended by the supplier (New England Biolabs). Purification of the linear plasmid, was achieved using agarose gel purification and the Qia-quick gel purification kit as per the protocol supplied by the manufacturer (Qiagen). The Haemophilus influenzae FabI gene was excised from TOPO TA 2.1 by KpnI and NotI restriction endonuclease digestion and purified as above. Subsequent fragment/vector ligations were carried out using T4 DNA ligase, using conditions supplied by the manufacturer (Promega).

Transformations into E. coli TOP 10 competent cells were performed using the protocol as supplied by the manufacturer (Invitrogen). Verification of the resultant clones was carried out using colony PCR and restriction endonuclease digestion. Positive clones were then transformed into the expression strain E. coli DH5☐PRO, which expresses AraC in addition to the lac repressor.

Subsequent clones were then evaluated for expression at small-scale using the conditions as recommended by the manufacturer (Clontech). Expression analysis showed over-expressed protein bands of correct size for Haemophilus influenzae FabI clearly visible by SDS PAGE. Protein identity was further confirmed by peptide mass fingerprinting. Further analysis by N-terminal Amino Acid sequencing of the purified protein showed that the N-terminus starts 35 residues downstream of the presumptive initiation codon. DNA sequence analysis also highlighted the presence of a ribosome binding site upstream and correctly spaced from the new initiation codon. These findings match perfectly with E. coli FabI and the protein is also now a similar size to other FabIs. The over-expression construct has managed to use the correct ribosome binding site and start at the correct ATG to give the correct protein.

Purification of H. influenzae FabI

One liter of cells containing the H. influenzae FabI expression construct were grown to an OD600 of 0.6. Expression was induced as described above and the cells were grown for a further 3 h and then harvested. The cell pellet was resuspended in 10 ml 50 mM Tris pH 7.5, 1 mM PMSF, 1 mM benzamidine, 1 mM DTT (buffer A) and lysed by sonication. Cell debris was removed by centrifugation. The supernatant was loaded onto a Hi-load Q (16/10) column (Pharmacia) equilibrated in buffer A. Protein was eluted over a 200 mL gradient of 0-100% buffer B, where buffer B is buffer A+1 M KCl. Fractions containing FabI were identified by SDS PAGE and by their FabI activity and pooled.

1.5 M ammonium sulfate was added to the pooled fractions and these were then loaded onto a Hi-load phenyl sepharose (16/10) column (Pharmacia) equilibrated in 50 mM Tris pH 7.5, 1 mM PMSF, 1 mM benzamidine, 1 mM DTT, 1.5 M ammonium sulfate. Proteins were eluted with a gradient of ammonium sulfate (1.5 to 0 M) over 200 mL. Fractions containing FabI were identified as above and pooled. The pooled fractions were buffer exchanged into 100 mM Tris, pH 7.5, 2 mM DTT and glycerol was then added to 50%. The protein was stored at −20° C. The identity of the protein was confirmed by N-terminal sequencing and MALDI mass spectrometry.

Cloning of E. coli FabI:

A PCR fragment of correct size for E. coli FabI was PCR amplified from E. coli chromosomal DNA, subcloned into the TOPO TA cloning vector, and verified by colony PCR+restriction endonuclease analysis. The presumptive E. coli FabI PCR fragment was subcloned into the expression vector pBluePet. The FabI clone was transformed into E. coli strain BL21(DE3). Small Scale expression studies show an over-expressed protein band of correct molecular weight (~28 Kda) for E. coli FabI clearly visible following Coomassie staining of SDS PAGE gels. DNA sequencing of the E. coli FabI expression constructs illustrated that no errors were apparent. N' terminal amino acid sequencing has confirmed the over-expressed protein band to be E. coli FabI.

Purification of E. coli FabI

E. coli FabI was expressed as soluble protein to 15% of total cell protein, 120 g cells being recovered from 3 L fermentation in shake flasks in modified terrific broth. The cells were lysed and the sample centrifuged. The resulting supernatant was filtered and purified using three consecutive chromatography columns: ion-exchange (Sourse 15Q), dye-affinity (blue sepharose), and size exclusion (superose 12). After each column the FabI containing fractions were pooled, concentrated and checked for purity and biological activity.

S aureus FabI Enzyme Inhibition Assay (NADH):

Assays were carried out in half-area, 96-well microtitre plates. Compounds were evaluated in 50-uL assay mixtures containing 100 mM NaADA, pH 6.5 (ADA=N-[2-acetamido]-2-iminodiacetic acid), 4% glycerol, 0.25 mM crotonoyl CoA, 1 mM NADH, and an appropriate dilution of S. aureus FabI Inhibitors were typically varied over the range of 0.01-10 uM. The consumption of NADH was monitored for 20 minutes at 30° C. by following the change in absorbance at 340 nm. Initial velocities were estimated from an exponential fit of the non-linear progress curves represented by the slope of the tangent at t=0 min $IC_{50}$'s were estimated from a fit of the initial velocities to a standard, 4-parameter model and are typically reported as the mean±S.D. of duplicate determinations. Triclosan, a commercial antibacterial agent and inhibitor of FabI, is currently included in all assays as a positive control. Compounds of this invention have $IC_{50}$'s from about 5.0 micromolar to about 0.05 micromolar.

S aureus FabI Enzyme Inhibition Assay (NADPH):

Assays were carried out in half-area, 96-well microtitre plates. Compounds were evaluated in 150-uL assay mixtures containing 100 mM NaADA, pH 6.5 (ADA=N-[2-acetamido]-2-iminodiacetic acid), 4% glycerol, 0.25 mM crotonoyl CoA, 50 uM NADPH, and an appropriate dilution of S. aureus FabI. Inhibitors were typically varied over the range of 0.01-10 uM. The consumption of NADPH was monitored for 20 minutes at 30° C. by following the change in absorbance at 340 nm. Initial velocities were estimated from an exponential fit of the non-linear progress curves represented by the slope of the tangent at t=0 min $IC_{50}$'s were estimated from a fit of the initial velocities to a standard, 4-parameter model and are typically reported as the mean±S.D. of duplicate determinations. Triclosan, a commercial antibacterial agent and inhibitor of FabI, is currently included in all assays as a positive control.

H. influenzae FabI Enzyme Inhibition Assay:

Assays are carried out in half-area, 96-well microtiter plates. Compounds are evaluated in 150-uL assay mixtures containing 100 mM MES, 51 mM diethanolamine, 51 mM triethanolamine, pH 6.5 (MES=2-(N-morpholino)ethanesulfonic acid), 4% glycerol, 25 uM crotonoyl-ACP, 50 uM NADH, and an appropriate dilution of H. influenzae FabI (approximately 20 nM). Inhibitors are typically varied over the range of 0.01-10 uM. The consumption of NADH is monitored for 20 minutes at 30° C. by following the change in absorbance at 340 nm. Initial velocities are estimated from an exponential fit of the non-linear progress curves. IC50's are estimated from a fit of the initial velocities to a standard, 4-parameter model, and are typically reported as the mean±S.D. of duplicate determinations. The apparent Ki is calculated assuming the inhibition is competitive with crotonoyl-ACP. A proprietary lead compound is currently included in all assays as a positive control.

E. coli FabI Enzyme Inhibition Assay:

Assays were carried out in half-area, 96-well microtitre plates. Compounds were evaluated in 150-uL assay mixtures containing 100 mM NaADA, pH 6.5 (ADA=N-[2-acetamido]-2-iminodiacetic acid), 4% glycerol, 0.25 mM crotonoyl CoA, 50 uM NADH, and an appropriate dilution of E. coli FabI. Inhibitors were typically varied over the range of 0.01-10 uM. The consumption of NADH was monitored for 20 minutes at 30° C. by following the change in absorbance at 340 nm. Initial velocities were estimated from an exponential fit of the non-linear progress curves represented by the slope of the tangent at t=0 min $IC_{50}$'s were estimated from a fit of the initial velocities to a standard, 4-parameter model and are typically reported as the mean±S.D. of duplicate determinations. Triclosan, a commercial antibacterial agent and inhibitor of FabI, is currently included in all assays as a positive control. Compounds of this invention have $IC_{50}$'s from about 100.0 micromolar to about 0.05 micromolar.

Preparation and Purification of Crotonoyl-ACP:

Reactions contained 5 mg/mL E. coli apo-ACP, 0.8 mM crotonoyl-CoA (Fluka), 10 mM $MgCl_2$, and 30 uM S. pneumoniae ACP synthase in 50 mM NaHEPES, pH 7.5. The mixture was gently mixed on a magnetic stirrer at 23° C. for 2 hr, and the reaction was terminated by the addition of 15 mM EDTA. The reaction mixture was filtered through a 0.2 micron filter (Millipore) and applied to a MonoQ column (Pharmacia) equilibrated with 20 mM Tris-Cl, pH 7.5. The column was washed with buffer until all non-adherent material was removed (as observed by UV detection), and the crotonoyl-ACP was eluted with a linear gradient of 0 to 400 mM NaCl.

S. aureus FabI Enzyme Inhibition Assay Using Crotonoyl-ACP:

Assays are carried out in half-area, 96-well microtitre plates. Compounds are evaluated in 150 uL assay mixtures containing 100 mM NaADA, pH 6.5 (ADA=N-(2-acetamido)-2-iminodiacetic acid), 4% glycerol, 25 uM crotonoyl-ACP, 50 uM NADPH, and an appropriate dilution of S. aureus Fab I (approximately 20 nM). Inhibitors are typically varied over the range of 0.01-10 uM. The consumption of NADPH is monitored for 20 minutes at 30° C. by following the change in absorbance at 340 nm. Initial velocities are estimated from a linear fit of the progress curves. IC50's are estimated from a fit of the initial velocities to a standard, 4-parameter model (Equation 1) and are typically reported as the mean±S.D. of duplicate determinations. Compounds of this invention in this assay have IC$_{50}$'s from about 100.0 micromolar to about 0.04 micromolar. The apparent Ki is calculated from Equation 2 assuming the inhibition is competitive with crotonoyl-ACP.

$$v=\text{Range}/(1+[I]/IC50)s+\text{Background} \qquad \text{Equation 1}$$

$$Ki(app)=IC50/(1+[S]/Ks) \qquad \text{Equation 2}$$

Antimicrobial Activity Assay:

Whole-cell antimicrobial activity was determined by broth microdilution using the National Committee for Clinical Laboratory Standards (NCCLS) recommended procedure, Document M7-A4, "Methods for Dilution Susceptibility Tests for Bacteria that Grow Aerobically". The compound was tested in serial two-fold dilutions ranging from 0.06 to 64 mcg/mL. Test organisms were selected from the following laboratory strains: *Staphylococcus aureus* Oxford, *Staphylococcus aureus* WCUH29, *Streptococcus pneumoniae* ERY2, *Streptococcus pneumoniae* 1629, *Streptococcus pneumoniae* N 1387, *Enterococcus faecalis* I, *Enterococcus faecalis* 7, *Haemophilus influenzae* Q1, *Haemophilus influenzae* NEMC1, *Moraxella Catarrhalis* 1502, *Escherichia coli* 7623 AcrABEFD+, *Escherichia coli* 120 AcrAB−, *Escherichia coli* MG1655, *Escherichia coli* MG1658. The minimum inhibitory concentration (MIC) was determined as the lowest concentration of compound that inhibited visible growth. A mirror reader was used to assist in determining the MIC endpoint.

One skilled in the art would consider any compound with a MIC of less than 256 µg/mL to be a potential lead compound. Preferably, the compounds used in the antimicrobial assays of the present invention have a MIC value of less than 128 µg/mL. Most preferably, said compounds have a MIC value of less than 64 µg/mL.

The examples which follow are intended in no way to limit the scope of this invention, but are provided to illustrate how to make and use the compounds of this invention. Many other embodiments will be readily apparent to those skilled in the art.

EXAMPLES

General

Proton nuclear magnetic resonance ($^1$H NMR) spectra were recorded at either 300 or 400 MHz, and chemical shifts are reported in parts per million (δ) downfield from the internal standard tetramethylsilane (TMS). Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz. CDCl$_3$ is deuteriochloroform, DMSO-d$_6$ is hexadeuteriodimethylsulfoxide, and CD$_3$OD is tetradeuteriomethanol. Mass spectra were obtained using electrospray (ES) ionization techniques. Elemental analyses were performed by Quantitative Technologies Inc., Whitehouse, N.J. Melting points were obtained on a Thomas-Hoover melting point apparatus and are uncorrected. All temperatures are reported in degrees Celsius. Analtech Silica Gel GF and E. Merck Silica Gel 60 F-254 thin layer plates were used for thin layer chromatography. Flash chromatography was carried out on E. Merck Kieselgel 60 (230-400 mesh) silica gel. Analytical HPLC was performed on Beckman chromatography systems. Preparative HPLC was performed using Gilson chromatography systems. ODS refers to an octadecylsilyl derivatized silica gel chromatographic support. YMC ODS-AQ® is an ODS chromatographic support and is a registered trademark of YMC Co. Ltd., Kyoto, Japan. PRP-1® is a polymeric (styrene-divinylbenzene) chromatographic support, and is a registered trademark of Hamilton Co., Reno, Nev. celite® is a filter aid composed of acid-washed diatomaceous silica, and is a registered trademark of Manville Corp., Denver, Colo.

Preparation 1

Preparation of (E)-3-(6-aminopyridin-3-yl)acrylic acid (Method A)

a) Benzyl (E)-3-(6-aminopyridin-3-yl)acrylate

A solution of 2-amino-5-bromopyridine (2.25 g, 13.0 mmole), benzyl acrylate (3.2 g, 19.7 mmole), Pd(OAc)$_2$ (0.31 g, 1.4 mmole), tri-ortho-tolylphosphine (0.73 g, 2.4 mmole), and diisopropylethylamine (3.5 mL, 20.0 mmole) in propionitrile (50 mL) was heated at reflux overnight. The dark mixture was filtered through celite®, and the filtrate was concentrated. Flash chromatography on silica gel (3% MeOH/CH$_2$Cl$_2$) gave the title compound (1.3 g, 39%): MS (ES) m/e 255 (M+H)$^+$.

b) (E)-3-(6-Aminopyridin-3-yl)acrylic acid

A solution of benzyl (E)-3-(6-aminopyridin-3-yl)acrylate (1.3 g, 5.1 mmole) and 1.0 N NaOH (10 mL, 10 mmole) in MeOH was heated at reflux overnight. The solution was concentrated in vacuo, and the residue was dissolved in H$_2$O. The pH was adjusted to 6 with dilute HCl, and the solid precipitate was collected by suction filtration and dried to give the title compound (0.6 g, 72%) as a white solid: MS (ES) m/e 165 (M+H)$^+$.

Preparation 2

Preparation of (E)-3-(6-aminopyridin-3-yl)acrylic acid (Method B)

a) (E)-3-(6-Aminopyridin-3-yl)acrylic acid

Acrylic acid (23 mL, 0.33 mole) was added carefully to a solution of 2-amino-5-bromopyridine (25.92 g, 0.15 mole) and Na$_2$CO$_3$ (55.64 g, 0.53 mole) in H$_2$O (600 mL). PdCl$_2$ (0.53 g, 0.003 mole) was then added, and the mixture was heated at reflux. After 24 hr, the reaction was cooled to RT and filtered, and the filtrate was adjusted to pH 6 with aqueous HCl. Additional H$_2$O (0.5 L) was added to improve mixing, and the mixture was stirred for 1 hr. The pH was readjusted to 6, then the solid was collected by suction filtration. The filter pad was washed sequentially with H$_2$O (2×0.5 L), cold absolute EtOH (100 mL), and Et$_2$O (2×250 mL). Drying in high vacuum at elevated temperature gave the title compound (15.38 g, 62%) as a tan solid: $^1$H NMR (300 MHz, DMSO-d$_6$) δ 8.11 (d, J=2.0 Hz, 1 H), 7.75 (dd, J=8.7, 2.0 Hz, 1 H), 7.43 (d, J=15.8 Hz, 1 H), 6.53 (s, 2 H), 6.45 (d, J=8.7 Hz, 1 H), 6.22 (d, J=15.8 Hz, 1 H); MS (ES) m/e 165 (M+H)$^+$.

Preparation 3

Preparation of (E)-3-(2-aminopyrimidin-5-yl)acrylic acid a) Benzyl (E)-3-(2-aminopyrimidin-5-yl)acrylate According to the procedure of Preparation 1 (a), except substituting 5-bromo-2-aminopyrimidine (1.95 g, 11.2 mmole) for 2-amino-5-bromopyridine, the title compound (2.25 g, 79%) was prepared as a light orange solid: MS (ES) m/e 256 (M+H)$^+$.

b) (E)-3-(2-Aminopyrimidin-5-yl)acrylic acid

According to the procedure of Preparation 1 (b), except substituting benzyl (E)-3-(2-aminopyrimidin-5-yl)acrylate (2.93 g, 11.5 mmole) for benzyl (E)-3-(6-aminopyridin-3-yl) acrylate, the title compound (1.71 g, 90%) was prepared as an off-white solid: MS (ES) m/e 166 (M+H)$^+$.

Preparation 4

Preparation of
6-bromo-3,4-dihydro-1H-1,8-naphthyridin-2-one a) 2-Amino-3-(hydroxymethyl)pyridine Solid 2-aminonicotinic acid (199 g, 1.44 mole) was added in portions over 4 hr to 1.0 M LiAlH$_4$ in THF (3 L, 3 mole) with stirring under Argon. An ice-bath was applied to control the temperature below 30° C. After the addition was complete, the reaction was heated at reflux for 16 hr, then was cooled to 0° C. and carefully quenched by sequential addition of H$_2$O (120 mL), 15% NaOH in H$_2$O (120 mL), and H$_2$O (350 mL). The resulting thick suspension was stirred for 1 hr, then was filtered through a pad of celite®. The filter pad was rinsed with THF (1 L), and the filtrate was concentrated to dryness to give the title compound (156 g, 87%) as a pale yellow waxy solid: MS (ES) m/e 125.1 (M+H)$^+$; $^1$H NMR (400 MHz, DMSO-d$_6$) δ 7.84 (dd, 1 H), 7.37 (m, 1 H), 6.53 (dd, 1 H), 5.65 (br s, 2 H), 5.16 (t, 1 H), 4.34 (d, J=4.6 Hz, 2 H).

b) 2-Amino-5-bromo-3-(hydroxymethyl)pyridine hydrobromide

To a stirred solution of 2-amino-3-(hydroxymethyl)pyridine (156 g, 1.257 mole) in HOAc (2.5 L) at ambient temperature was added bromine (64.1 mL, 1.257 mole) dropwise over 1 hr. A suspension began to form during the addition. An exotherm to 36° C. was controlled with an ice bath. After the addition, the reaction mixture was stirred at ambient temperature overnight. The yellow precipitate was filtered, washed with ether and air-dried to give the title compound (289 g, 81%): MS (ES) m/e 203.2 (M+H)$^+$; $^1$H NMR (400 MHz, DMSO-d$_6$, free base) δ 7.89 (d, J=2.3 Hz, 1 H), 7.52 (s, 1 H), 5.92 (br s, 2 H), 5.29 (br s, 1 H), 4.30 (s, 2 H).

c) 2-Amino-5-bromo-3-(bromomethyl)pyridine hydrobromide

A suspension of 2-amino-5-bromo-3-(hydroxymethyl)pyridine hydrobromide (289 g, 1.02 mole) in 48% aqueous HBr (2.9 L) was heated at reflux for 12 hrs. Complete solution occurred during heating. The reaction mixture was cooled and a crystalline precipitate formed. This was filtered and washed with ethyl acetate and air dried to give the title compound (305 g, 86%).

d) Methyl (±)-6-bromo-2-oxo-1,2,3,4-tetrahydro-1H-1,8-naphthyridine-3-carboxylate To a solution of dimethyl malonate (224 g, 1.7 mole) in DMF (2 L) and THF (2 L) stirred under argon and chilled to 3° C. with an ice-acetone bath was added NaH (60% Nujol dispersion, 69.2 g, 1.7 mole) in portions over 1.5 hr. The anion solution was stirred for 15 min at ca. 5° C., then 2-amino-5-bromo-3-(bromomethyl)pyridine hydrobromide (200 g, 0.56 mole) was added in portions over 15 min. The reaction mixture was allowed to warm to ambient temperature during overnight stirring and then was heated to 80° C. for 2 hr. The reaction was then cooled and filtered and the precipitate was washed with ethyl acetate. This solid was then vigorously stirred in 2 L water for 15 min and again filtered and air-dried to give the title compound (113 g, 71%): MS (ES) m/e 286 (M+H)$^+$.

e) 6-Bromo-3,4-dihydro-1H-1,8-naphthyridin-2-one

To a suspension of methyl (±)-6-bromo-2-oxo-1,2,3,4-tetrahydro-1H-1,8-naphthyridine-3-carboxylate (170 g, 0.596 mole) in CH$_3$OH (10 L) was added 1.0 M NaOH (2.5 L). The reaction mixture was stirred and heated at reflux for 5 hrs and then cooled to ambient temperature. The suspension was acidified with 1.0 M HCl (3.0 L) and then was stirred and heated at reflux overnight. The reaction slurry was cooled and filtered and the solid was washed with water and vacuum dried to give the title compound (122 g of the hydrate, 90%) as an off-white solid, HPLC purity, 94%: MS (ES) m/e 228 (M+H)$^+$.

Preparation 5

Preparation of 6-bromo-3-methyl-3,4-dihydro-1H-pyrido[2,3-d]pyrimidin-2-one a) 2-Amino-5-bromo-3-(methylaminomethyl)pyridine A solution of 2-amino-5-bromo-3-(hydroxymethyl)pyridine (5.00 g, 24.6 mmole), from Preparation 4 (b), in 48% aqueous HBr (50 mL) was heated at reflux for 12 hrs. The reaction was concentrated and toluene was used to azeotrope the residual H$_2$O. The resulting light brown solid was placed under high vacuum overnight and used directly.

A solution of the 2-amino-3-(bromomethyl)-5-bromopyridine hydrobromide salt (prepared above) in 40% aqueous methylamine (50 mL) and THF (50 mL) was stirred at RT overnight in a pressure bottle. The reaction solution was concentrated and extracted with EtOAc (2×100 mL). The combined organic phases were washed with H$_2$O, dried over Na$_2$SO$_4$ and concentrated. Purification on silica gel afforded the title compound (4.25 g, 80%) as a yellow oil: MS (ES) m/e 217 (M+H)$^+$.

b) 6-Bromo-3-methyl-3,4-dihydro-1H-pyrido[2,3-d]pyrimidin-2-one

To a solution of 2-amino-5-bromo-3-(methylaminomethyl)pyridine (2.0 g, 9.3 mmole) in dichloroethane (50 mL) was added 1,1'-carbonyldiimidazole (1.9 g, 11.5 mmole). The reaction was heated at 50° C. overnight and concentrated. The residue was purified on silica gel (9:1 CHCl$_3$/CH$_3$OH containing 5% NH$_4$OH) to give the title compound (1.72 g, 77%) as an off-white solid: MS (ES) m/e 243 (M+H)$^+$.

Preparation 6

Preparation of
(E)-3-(3H-imidazo[4,5-b]pyridin-6-yl)acrylic acid a) 5-Bromo-2,3-diaminopyridine To a suspension of 2-amino-5-bromo-3-nitropyridine (2.0 g, 9.17 mmole) in absolute EtOH (50 mL) was added SnCl$_2$ hydrate (9.3 g, 41.3 mmole), then the mixture was heated to reflux. After 3 hr the mixture was cooled to RT and concentrated. The residue was taken up in 2.0 M NaOH and extracted with EtOAc (3×). The combined organic layers were dried (MgSO$_4$), filtered, and concentrated to give the title compound (1.69 g, 98%) which was sufficiently pure for use in the next step: MS (ES) m/e 188/190 (M+H)$^+$.

b) 6-Bromo-3H-imidazo[4,5-b]pyridine

5-Bromo-2,3-diaminopyridine (1.69 g, 8.99 mmole) was taken up in 96% formic acid (50 mL) and heated to reflux. After 18 hr the mixture was cooled to RT and concentrated. The residue was taken up in H$_2$O and the pH was adjusted to 7 with 2.0 M NaOH. The title compound (1.54 g, 87%) was collected as a solid by filtration, washed with H$_2$O, and dried in vacuo: MS (ES) m/e 198/200 (M+H)$^+$.

c) 6-Bromo-4-trityl-3H-imidazo[4,5-b]pyridine

To a suspension of 6-bromo-3H-imidazo[4,5-b]pyridine (1.2 g, 6.06 mmole) in CH$_2$Cl$_2$ (30 mL) was added Et$_3$N (1.3 mL, 9.09 mmole) then trityl chloride (2.03 g, 7.27 mmole) at RT. After 72 hr the mixture was washed with H$_2$O (2×) and brine, then was dried (MgSO$_4$), filtered, and concentrated under reduced pressure to afford the title compound. This was used directly in the next step.

d) Benzyl (E)-3-(4-trityl-3H-imidazo[4,5-b]pyridin-6-yl) acrylate

A solution of 6-bromo-4-trityl-3H-imidazo[4,5-b]pyridine (from step a) (6.06 mmole), benzyl acrylate (1.18 g, 7.27 mmole), Pd(OAc)$_2$ (67 mg, 0.30 mmole), P(o-tolyl)$_3$ (183 mg, 0.6 mmole), and (i-Pr)$_2$NEt (2.64 mL, 15.15 mmole) in propionitrile (30 mL) was degassed (3×N$_2$/vacuum) then heated to reflux. After 4 hr the mixture was cooled to RT and concentrated. Flash chromatography on silica gel (30% EtOAc/hexanes) gave the title compound (1.75 g, 55% over 2 steps) as an off-white foam: $^1$H NMR (400 MHz, CDCl$_3$) δ 8.24 (d, J=2.0 Hz, 1 H), 8.19 (d, J=2.0 Hz, 1 H), 8.06 (s, 1 H), 7.77 (d, J=16.0 Hz, 1 H), 7.42-7.11 (m, 20 H), 6.48 (d, J=16.0 Hz, 1 H), 5.25 (s, 2 H).

d) (E)-3-(3H-Imidazo[4,5-b]pyridin-6-yl)acrylic acid

Benzyl (E)-3-(4-trityl-3H-imidazo[4,5-b]pyridin-6-yl) acrylate (1.75 g, 3.35 mmole) was dissolved in 4 N HCl in dioxane (20 mL). After 1 hr the mixture was concentrated. The residue was taken up in 1:1 MeOH/H$_2$O (15 mL). 2.0 N NaOH (15 mL, 15 mmole) was added and the mixture was heated to reflux. After 18 hr the mixture was cooled to RT and concentrated to approximately ⅓ volume. The mixture was adjusted to pH 4 using 10% HCl. The solid was collected by filtration, washed with H$_2$O, and dried in vacuo to give the title compound (329 mg, 52% over 2 steps) as a white solid: $^1$H NMR (400 MHz, d$^6$-DMSO) δ 9.10 (s, 1 H), 8.94 (s, 1 H), 8.84 (s, 1 H), 8.20 (d, J=16.0 Hz, 1 H), 7.10 (d, J=16.0 Hz, 1 H).

Preparation 7

Preparation of (E)-3-(3,4-dihydro-2H-pyrido[3,2-b]-1,4-oxazin-7-yl)acrylic acid a) 3,4-Dihydro-2H-pyrido[3,2-b]-1,4-oxazine To a suspension of 2H-pyrido[3,2-b]-1,4-oxazin-3(4H)-one (2.0 g, 13.3 mmole) in dry THF (40 mL) was added a solution of LiAlH$_4$ in THF (1.0 M, 26.6 mL, 26.6 mmole) slowly at 0° C. After 1 hr the mixture was quenched with 2.0 M NaOH until a solid formed. The mixture was dried (MgSO$_4$), filtered, and concentrated under reduced pressure to give the title compound (1.44 g, 79%) as a white solid which was sufficiently pure for use in the next step: MS (ES) m/e 137 (M+H)$^+$.

b) 4-(tert-Butoxycarbonyl)-3,4-dihydro-2H-pyrido[3,2-b]-1,4-oxazine

To a solution of 3,4-dihydro-2H-pyrido[3,2-b]-1,4-oxazine (1.44 g, 10.6 mmole) and di-tert-butyl dicarbonate (2.78 g, 12.7 mmole) in dry THF (50 mL) was added a solution of LiHMDS in THF (1.0 M, 12.7 mL, 12.7 mmole) dropwise at 0° C. After 30 min the mixture was quenched with saturated NH$_4$Cl and extracted with EtOAc (3×). The combined organic layers were dried (MgSO$_4$), filtered, and concentrated. Flash chromatography on silica gel (40% EtOAc/hexanes) gave the title compound (2.0 g, 80%) as a clear oil: MS (ES) m/e 237 (M+H)$^+$.

c) 4-(tert-Butoxycarbonyl)-7-bromo-3,4-dihydro-2H-pyrido [3,2-b]-1,4-oxazine

To a solution of 4-(tert-butoxycarbonyl)-3,4-dihydro-2H-pyrido[3,2-b]-1,4-oxazine (2.0 g, 8.46 mmole) in MeOH (40 mL) was added Br$_2$ (0.53 mL, 10.2 mmole) dropwise at 0° C. After 1 hr the mixture was concentrated. The residue was taken up in 1:1 Et$_2$O/hexanes and filtered. The filtrate was concentrated under reduced pressure to give the title compound (1.27 g, 48%) as an oil which solidified under vacuum: $^1$H NMR (400 MHz, CDCl$_3$) δ 8.10 (s, 1 H), 7.33 (s, 1 H), 4.25 (m, 2 H), 3.92 (m, 2 H), 1.54 (s, 9 H).

d) (E)-3-[4-(tert-Butoxycarbonyl)-3,4-dihydro-2H-pyrido[3,2-b]-1,4-oxazin-7-yl]acrylic acid A solution of 4-(tert-butoxycarbonyl)-7-bromo-3,4-dihydro-2H-pyrido[3,2-b]-1,4-oxazine (1.27 g, 4.03 mmole), benzyl acrylate (785 mg, 4.84 mmole), Pd(OAc)$_2$ (45 mg, 0.20 mmole), P(o-tolyl)$_3$ (122 mg, 0.4 mmole), and (i-Pr)$_2$NEt (1.76 mL, 10.1 mmole) in propionitrile (20 mL) was degassed (3×N$_2$/vacuum) then heated to reflux. After 18 hr the mixture was cooled to RT and concentrated. Flash chromatography on silica gel (25% EtOAc/hexanes) gave the title compound (1.17 g, 73%) as a yellow oil: MS (ES) m/e 397 (M+H)$^+$.

e) (E)-3-(3,4-dihydro-2H-pyrido[3,2-b][1,4]oxazin-7-yl) acrylic acid (E)-3-[4-(tert-Butoxycarbonyl)-3,4-dihydro-2H-pyrido[3,2-b]-1,4-oxazin-7-yl]acrylic acid (1.17 g, 2.95 mmole) was dissolved in 4 N HCl in dioxane (15 mL). After 72 hr the mixture was concentrated. The residue was taken up in 1:1 MeOH/H$_2$O (20 mL). 1.0 N LiOH (15 mL, 15 mmole) was added and the mixture was heated to reflux. After 18 hr the mixture was cooled to RT and concentrated to approximately ⅓ volume. The mixture was adjusted to pH 6 using 10% HCl. The solid was collected by filtration, washed with H$_2$O and dried in vacuo to give the title compound (315 mg, 52% over 2 steps): MS (ES) m/e 207 (M+H)$^+$.

Preparation 8

Preparation of 5-bromo-2,2'-dipyridylamine

To a stirred solution of 2,5-dibromopyridine (2.4 g, 10.1 mmole) in dry toluene (75 mL) were added 2-aminopyridine (1.0 g, 10.6 mmole), tris(dibenzylideneacetone)dipalladium (0) (183 mg, 0.2 mmole), 1,3-bis(diphenylphosphino)propane (165 mg, 0.4 mmole) and sodium tert-butoxide (1.35 g, 14 mmole). The reaction was purged with Ar then heated with stirring at 70° C. After 4 h the reaction was cooled to RT, taken up in Et$_2$O (200 mL), washed with brine, dried (MgSO$_4$) and concentrated to dryness. The remaining residue was purified by flash chromatography on silica gel (0.5% (5% NH$_4$OH/MeOH)/CHCl$_3$), triturated with hexane and dried under vacuum to give the title product (1.31 g, 52%) as a pale yellow solid: $^1$H NMR (400 MHz, CDCl$_3$) δ 9.88 (s, 1 H), 8.31 (s, 1 H), 8.23 (d, J=4.8 Hz, 1 H), 7.83 (m, 2 H), 7.67 (t, 1 H), 7.62 (d, J=8.4 Hz, 1 H), 6.90 (t, 1 H); MS (ES) m/e 250.0 (M+H)$^+$.

Preparation 9

Preparation of 1-methyl-2-(methylaminomethyl)-1H-indole a) Ethyl 1-methyl-1H-indole-2-carboxylate NaH (60% dispersion in mineral oil, 8.02 g, 200.49 mmole) was washed with hexanes, then was suspended in dry DMF (530 mL). Solid ethyl indole-2-carboxylate (25.29 g, 133.66 mmole) was added portionwise over 5-10 min, allowing gas evolution to subside between additions. When the addition was complete, the yellow mixture was stirred for 15 min, then methyl iodide (42 mL, 668.3 mmole) was added all at once. The reaction was exothermic, and the internal temperature rose to 40-45° C. After 1 hr, the reaction was quenched with 10% $NH_4Cl$ (100 mL) and concentrated on the rotavap (high vacuum). The residue was partitioned between $Et_2O$ (500 mL) and $H_2O$ (100 mL), and the layers were separated. The $Et_2O$ layer was washed with $H_2O$ (100 mL), dried ($MgSO_4$), and concentrated to leave the title compound (27.10 g, quantitative) as a light yellow solid. This was used without further purification: TLC (10% EtOAc/hexanes) Rf=0.39.

b) N,1-Dimethyl-1H-indole-2-carboxamide

A suspension of ethyl 1-methyl-1H-indole-2-carboxylate (27.10 g, 133.34 mmole) in 40% aqueous $CH_3NH_2$ (300 mL) and MeOH (30 mL) was stirred at RT. A solid tended to gradually creep up the walls of the flask, and was washed down periodically with MeOH. The flask was tightly stoppered to keep the material inside the flask. As the reaction proceeded, the solid dissolved, but eventually the product began to precipitate. The reaction was stirred at RT for 5 days, then was concentrated to remove approximately 200 mL of the solvent. The remaining residue was diluted with $H_2O$ (300 mL), and the solid was collected by suction filtration and washed with $H_2O$. Drying at 50-60° C. in high vacuum left the title compound (23.45 g, 93%) as a faintly yellow solid: $^1H$ NMR (300 MHz, $CDCl_3$) δ 7.63 (d, J=8.0 Hz, 1 H), 7.27-7.43 (m, 2 H), 7.10-7.20 (m, 1 H), 6.80 (s, 1 H), 6.10-6.30 (m, 1 H), 4.06 (s, 3 H), 3.01 (d, J=4.9 Hz, 3 H).

c) 1-Methyl-2-(methylaminomethyl)-1H-indole

A 3-liter 3-necked roundbottom flask equipped with overhead stirring was charged with N,1-dimethyl-1H-indole-2-carboxamide (23.45 g, 124.58 mmole) and anhydrous THF (170 mL). The solution was stirred while a solution of $LiAlH_4$ in THF (1.0 M, 250 mL, 250 mmole) was added via syringe. Gas was evolved during the addition of the first 50 mL of $LiAlH_4$ solution. When the addition was complete, the resulting light yellow solution was heated at gentle reflux. After 23 hr, the reaction was cooled in ice and quenched by the sequential dropwise addition of $H_2O$ (9.5 mL), 15% NaOH (9.5 mL), and $H_2O$ (28.5 mL). The mixture was stirred for 15 min, then was filtered through celite®, and the filter pad was washed thoroughly with THF. The filtrate was concentrated and the residue was flash chromatographed on silica gel (10% MeOH/$CHCl_3$ containing 0.5% conc. $NH_4OH$). The title compound (20.17 g, 93%) was obtained as a light yellow oil: $^1H$ NMR (300 MHz, $CDCl_3$) δ 7.56 (d, J=7.8 Hz, 1 H), 7.02-7.35 (m, 3 H), 6.38 (s, 1 H), 3.88 (s, 2 H), 3.75 (s, 3 H), 2.49 (s, 3 H).

Preparation 10

Preparation of 1-methyl-3-(methylaminomethyl)-1H-indole (Method A)

a) Methyl 1-methyl-1H-indole-3-carboxylate

NaH (60% dispersion in mineral oil, 8.56 g, 214.0 mmole) was added portionwise, allowing for gas evolution, to a solution of methyl 1H-indole-3-carboxylate (25.00 g, 142.7 mmole) in DMF (350 mL) at 0° C. When the NaH addition was complete, methyl iodide (44.4 mL, 713.5 mmole) was added at 0° C. The reaction was stirred at 0° C. for 15 minutes then at RT overnight. The reaction was diluted with water and extracted with ethyl acetate. The combined extracts were dried over $K_2CO_3$ and concentrated to afford the title compound (26.00 g, 96%) as an orange solid: MS (ES) m/e 190 (M+H)$^+$.

b) N,1-Dimethyl-1H-indole-3-carboxamide

A suspension of methyl 1-methyl-1H-indole-3-carboxylate (4.30 g, 22.74 mmole) in 40% aqueous $CH_3NH_2$ (400 mL) was stirred at RT. The flask was tightly stoppered to keep the material inside the flask. As the reaction proceeded the product began to precipitate. The reaction was stirred at RT for 3 days, then was concentrated to remove approximately 200 mL of the solvent. The remaining residue was diluted with $H_2O$ (500 mL), and the solid was collected by suction filtration and washed with $H_2O$. Flash chromatography on silica gel (ethyl acetate) gave the title compound (2.4 g, 56%) as a white solid: MS (ES) m/e 189 (M+H)$^+$.

c) 1-Methyl-3-(methylaminomethyl)-1H-indole

A solution of $LiAlH_4$ in THF (1.0 M, 5.20 mL, 5.2 mmole) was slowly added via syringe to a solution of N,1-dimethyl-1H-indole-3-carboxamide (0.50 g, 2.6 mmole) in anhydrous THF (15 mL). Gas was evolved during the addition of the first 2 mL of $LiAlH_4$ solution. When the addition was complete, the resulting light yellow solution was heated at gentle reflux. After 23 hr, the reaction was cooled in ice and quenched by the sequential dropwise addition of $H_2O$ (0.5 mL), 1.0 N NaOH (0.5 mL), and $H_2O$ (0.5 mL). The mixture was stirred for 15 min, then was filtered through celite®, and the filter pad was washed thoroughly with THF. The filtrate was concentrated and the residue was flash chromatographed on silica gel (10% MeOH/$CHCl_3$ containing 0.5% conc. $NH_4OH$) to afford the title compound (0.30 g, 67%) as a light yellow oil: MS (ES) m/e 175 (M+H)$^+$.

Preparation 11

Preparation of 1-methyl-3-(methylaminomethyl)-1H-indole (Method B)

To a solution of 1-methylindole-3-carboxaldehyde (10.0 g, 62.8 mmole) in MeOH (100 mL) was added a solution of 2.0 M $CH_3NH_2$ in MeOH (126 mL, 252.0 mmole). The reaction was stirred at RT for 2 hrs, then was concentrated to a light yellow oil. This oil was dissolved in EtOH (300 mL), and $NaBH_4$ (2.38 g, 62.8 mmole) was added. After 2 hrs the reaction was concentrated to a slurry and dissolved in 1.0 N NaOH (75 mL). The aqueous solution was extracted with $Et_2O$ (2×200 mL) and the combined organic fractions were dried over $Na_2SO_4$ and concentrated. Flash chromatography on silica gel (9:1 $CHCl_3$/MeOH containing 5% $NH_4OH$) and drying in high vacuum left the title compound (10.1 g, 92%) as a faintly yellow oil: MS (ES) m/e 175 (M+H)$^+$.

Preparation 12

Preparation of 2-methyl-3-(methylaminomethyl)indole

To a solution of 2-methylindole-3-carboxaldehyde (10.00 g, 62.84 mmole) in MeOH (100 mL) was added 2 M $CH_3NH_2$ in MeOH (200 mL). After stirring for 3 hours at RT, the reaction solution was concentrated to a yellow oil which solidified under vacuum. This solid was dissolved in ethanol (350 mL) and $NaBH_4$ (2.38 g, 62.8 mmole) was added. The reaction was stirred at RT for 6 hours, then was concentrated under vacuum. The remaining residue was diluted with saturated aqueous $Na_2CO_3$ (50 mL) and extracted with EtOAc (2×200 mL). The organic phase was separated, washed with brine, and dried over $Na_2SO_4$. Flash chromatography on silica gel (9:1 $CHCl_3$/MeOH containing 5% $NH_4OH$) and drying under high vacuum gave the title compound (6.88 g, 63%) as a faintly yellow viscous solid: MS (ES) m/e 175 (M+H)$^+$.

Preparation 13

Preparation of 1,3-dimethyl-2-(methylaminomethyl)-1H-indole a) 1,3-Dimethyl-1H-indole To a stirred solution of 3-methylindole (15.0 g, 114 mmole) in dry DMF (200 mL) was added NaH (60% dispersion in oil, 5.0 g, 125 mmole) in portions. Gas evolution was observed. The mixture was stirred for 30 min, then iodomethane (8 mL, 129 mmole) was added in one portion. The reaction became exothermic and was cooled in an ice bath. After 16 hr at RT, the reaction was concentrated under vacuum and the residue was taken up in ethyl acetate. The solution was washed with $H_2O$ then with brine, dried ($MgSO_4$), and concentrated to dryness. Purification by short path distillation under vacuum (bp 88-92° C., 0.5 mmHg) gave the title compound (16.10 g, 97%) as a pale yellow oil: $^1H$ NMR (400 MHz, $CDCl_3$) δ 7.47 (d, J=7.9 Hz, 1 H), 7.35 (d, J=8.2 Hz, 1 H), 7.13 (t, 1 H), 7.06 (s, 1 H), 7.00 (t, 1 H), 3.71 (s, 3 H), 2.24 (s, 3 H).

b) 1,3-Dimethyl-1H-indole-2-carboxaldehyde

To a stirred solution of phosphorus oxychloride (7.0 mL, 75 mmole) in DMF (25 mL) was added dropwise a solution of 1,3-dimethylindole (12.0 g, 83 mmole) in dry DMF (6.0 mL). The reaction was stirred at RT for 2 hr then was poured onto ice. The mixture was basified with a solution of NaOH (13.2 g, 330 mmole) in $H_2O$ (44 mL), then was extracted with $Et_2O$ (2×50 mL). The combined organic layers were washed with brine, dried ($MgSO_4$), and concentrated under vacuum. Flash chromatography on silica gel (10% ethyl acetate/hexanes) gave the title compound (13.03 g, 91%) as an off-white solid: LCMS (ES) m/e 174.2 $(M+H)^+$; $^1H$ NMR (400 MHz, $CDCl_3$) δ 10.16 (s, 1 H), 7.68 (d, J=8.1 Hz, 1 H), 7.42 (t, 1 H), 7.32 (d, J=8.5 Hz, 1 H), 7.15 (t, 1 H), 4.04 (s, 3 H), 2.63 (s, 3 H).

c) 1,3-Dimethyl-2-(methylaminomethyl)-1H-indole

To 1,3-dimethyl-1H-indole-2-carboxaldehyde (13.0 g, 75 mmole) was added a solution of 2.0 M methylamine in methanol (150 mL, 300 mmole) and HOAc (4.3 mL, 75 mmole). The solution was stirred at RT for 4 hr, then was cooled to 0° C., and sodium cyanoborohydride (5.0 g, 80 mmole) was added portionwise over 5 min. The reaction was then allowed to warm to RT. After 16 hr, the reaction was concentrated under vacuum and the residue was taken up in $Et_2O$. The solution was washed with 1.0 N NaOH then with brine, dried ($Na_2SO_4$), and concentrated to dryness. Flash chromatography on silica gel (95:5 $CHCl_3$/methanol containing 5% $NH_4OH$) gave the title compound (7.34 g, 52%) as a yellow oil: $^1H$ NMR (400 MHz, $CDCl_3$) δ 7.53 (d, J=7.8 Hz, 1 H), 7.26 (d, J=7.8 Hz, 1 H), 7.20 (t, 1 H), 7.09 (t, 1 H), 3.88 (s, 2 H), 3.76 (s, 3 H), 2.46 (s, 3 H), 2.32 (s, 3 H), 1.36 (br s, 1 H).

Preparation 14

Preparation of 1-methyl-3-(methylaminomethyl)-1H-pyrrolo[2,3-b]pyridine a) 1-Methyl-1H-pyrrolo[2,3-b]pyridine According to the procedure of Preparation 13 (a), except substituting 7-azaindole (2.28 g, 1.83 mmole) for the 3-methylindole, the title compound (1.4 g, 58%) was prepared as a yellow oil: MS (ES) m/e 133 $(M+H)^+$.

b) 1-Methyl-1H-pyrrolo[2,3-b]pyridine-3-carboxaldehyde

According to the procedure of Preparation 13 (b), except substituting 1-methyl-1H-pyrrolo[2,3-b]pyridine (0.7 g, 5.3 mmole) for the 1,3-dimethylindole, the title compound (0.4 g, 47%) was prepared as a white solid: MS (ES) m/e 161 $(M+H)^+$.

c) 1-Methyl-3-(methylaminomethyl)-1H-pyrrolo[2,3-b]pyridine

According to the procedure of Preparation 13 (c), except substituting 1-methyl-1H-pyrrolo[2,3-b]pyridine-3-carboxaldehyde (0.4 g, 2.5 mmole) for the 1,3-dimethyl-1H-indole-2-carboxaldehyde, the title compound (0.2 g, 45%) was prepared as a yellow oil: MS (ES) m/e 176 $(M+H)^+$.

Preparation 15

Preparation of 2-methyl-3-(methylaminomethyl)benzo[b]thiophene a) 2-Methylbenzo[b]thiophene-3-carboxaldehyde $SnCl_4$ (20 mL, 67 mmole) was added over 5 min to a stirred solution of 2-methylbenzo[b]thiophene (5.0 g, 33.7 mmole) in $CH_2Cl_2$ (75 mL) at 0° C. under argon. After 15 minutes, dichloromethyl methyl ether (3.7 mL, 41 mmole) was added. The reaction became a yellowish colored suspension. The reaction was allowed to warm to RT and stirred for 16 h, then was poured onto ice water (200 mL). The aqueous mixture was acidified with 1.0 N HCl (100 mL) and stirred until the suspension dissolved. The organic phase was separated, dried ($MgSO_4$), and concentrated under vacuum. Purification by flash chromatography on silica gel (10% ethyl acetate/hexane) gave the title compound (5.83 g, 98%) as a white crystalline solid: $^1H$ NMR (400 MHz, $CDCl_3$) δ 10.38 (s, 1 H), 8.61 (d, J=8.1 Hz, 1 H), 7.77 (d, J=8.0 Hz, 1 H), 7.48 (t, 1 H), 7.39 (t, 1 H), 2.93 (s, 3 H).

b) 2-Methyl-3-(methylaminomethyl)benzo[b]thiophene

According to the procedures of Preparation 1, except substituting 2-methylbenzo[b]thiophene-3-carboxaldehyde (5.0 g, 28.4 mmole) for 1-methylindole-3-carboxaldehyde, the title compound (4.89 g, 90%) was prepared as an oil which solidified in the freezer: $^1H$ NMR (400 MHz, $CDCl_3$) δ 7.78 (d, J=7.9 Hz, 1 H), 7.75 (d, J=7.9 Hz, 1 H), 7.37 (t, 1 H), 7.29 (t, 1 H), 3.95 (s, 2 H), 2.60 (s, 3 H), 2.50 (s, 3 H).

Preparation 16

Preparation of 3-(methylaminomethyl)-1H-indole a) 3-(Methylaminomethyl)-1H-indole To a solution of indole-3-carboxaldehyde (5.4 g, 34.1 mmole) in MeOH (30 mL) was added a solution of 2.0 M $CH_3NH_2$ in MeOH (51.3 mL, 102.6 mmole). The reaction was stirred at RT overnight, then was concentrated to a light yellow oil. This oil was dissolved in EtOH (40 mL), and $NaBH_4$ (1.3 g, 34.1 mmole) was added. After 16 hrs the reaction was concentrated to a slurry and dissolved in 10% $Na_2CO_3$ (100 mL). The aqueous solution was extracted with EtOAc (2×200 mL) and the combined organic fractions were dried over $Na_2SO_4$ and concentrated. Drying in high vacuum left the title compound (5.2 g, 94%) as a faintly yellow oil: MS (ES) m/e 161 $(M+H)^+$.

Preparation 17

Preparation of 1-benzyl-3-(methylaminomethyl)-1H-indole a) 3-[N-(Benzyloxycarbonyl)-N-methylaminomethyl]-1H-indole N-(Benzyloxycarbonyloxy)succinimide (8.9 g, 35.7 mmole) was added to a solution of 3-(methylaminomethyl)-1H-indole (5.2 g, 32.5 mmole), from Preparation 16, and triethylamine (5.0 mL, 65.7 mmole) in DMF (100 mL) at RT.

The reaction was stirred overnight then was concentrated in vacuo. The residue was diluted with water and the mixture was extracted with ethyl acetate. The combined extracts were dried over $Na_2SO_4$ and concentrated. Flash chromatography on silica gel (33% ethyl acetate/hexanes) gave the title compound (7.0 g, 74%) as an off-white solid: MS (ES) m/e 295 $(M+H)^+$.

b) 3-[N-(Benzyloxycarbonyl)-N-methylaminomethyl]-1-benzyl-1H-indole

NaH (60% dispersion in mineral oil, 0.15 g, 3.8 mmole) was added portionwise, allowing for gas evolution, to a solution of 3-[N-(benzyloxycarbonyl)-N-methylaminomethyl]-1H-indole (0.7 g, 2.5 mmole) in DMF (25 mL) at 0° C. When the NaH addition was complete, benzyl bromide (1.2 mL, 10.0 mmole) was added at 0° C. The reaction was stirred at 0° C. for 15 minutes then at RT overnight. The reaction was diluted with water and extracted with ethyl acetate. The combined extracts were dried over $Na_2SO_4$ and concentrated. Flash chromatography on silica gel (33% ethyl acetate/hexanes) gave the title compound (0.9 g, 93%) as an off white solid: MS (ES) m/e 385 $(M+H)^+$.

c) 1-Benzyl-3-(methylaminomethyl)-1H-indole

3-[N-(Benzyloxycarbonyl)-N-methylaminomethyl]-1-benzyl-1H-indole (0.9 g, 2.3 mmole) was added to a suspension of Pearlman's catalyst (about 0.30 g) in MeOH at RT in a Parr flask. The reaction was placed under 50 p.s.i. of $H_2$ and shaken for 5 hr. The mixture was filtered through celite® and the filter pad was washed with MeOH. The filtrate was concentrated to afford the title compound (0.5 g, 86%) as a light yellow solid: MS (ES) m/e 251 $(M+H)^+$.

Preparation 18

Preparation of 2,3-dihydro-8-(methylaminomethyl)-1H-3a-azacyclopenta[a]indene a) 2,3-Dihydro-1H-3a-azacyclopenta[a]indene-8-carboxaldehyde According to the procedure of Preparation 13 (b), except substituting 2,3-dihydro-1H-3a-azacyclopenta[a]indene (J. Med. Chem. 1965, 8, 700; 0.24 g, 1.53 mmole) for the 1,3-dimethylindole, the title compound (0.17 g, 60%) was prepared as a yellow solid: MS (ES) m/e 186 $(M+H)^+$.

b) 2,3-Dihydro-8-(methylaminomethyl)-1H-3a-azacyclopenta[a]indene

According to the procedure of Preparation 13 (c), except substituting 2,3-dihydro-1H-3a-azacyclopenta[a]indene-8-carboxaldehyde (0.17 g, 0.92 mmole) for the 1,3-dimethyl-1H-indole-2-carboxaldehyde, the title compound (0.1 g, 54%) was prepared as a yellow oil: MS (ES) m/e 201 $(M+H)^+$.

Preparation 19

Preparation of 1,4-dimethyl-3-(methylaminomethyl)-1H-indole a) 1,4-Dimethyl-1H-indole According to the procedure of Preparation 9 (a), except substituting 4-methylindole for ethyl indole-2-carboxylate, the title compound (1.5 g, 94%) was prepared as an amber oil: MS (ES) m/e 146.2 $(M+H)^+$.

b) 1,4-Dimethyl-1H-indole-3-carboxaldehyde

According to the procedure of Preparation 9 (b), except substituting 1,4-dimethyl-1H-indole for 1,3-dimethylindole, the title compound (1.8 g, 95%) was prepared as an amber oil: MS (ES) m/e 174.2 $(M+H)^+$.

c) 1,4-Dimethyl-3-(methylaminomethyl)-1H-indole

According to the procedure of Preparation 11, except substituting 1,4-dimethyl-1H-indole-3-carboxaldehyde for 1,3-dimethyl-1H-indole-1-carboxaldehyde, the title compound (1.9 g, 99%) was prepared as an oil: MS (ES) m/e 189.0 $(M+H)^+$.

Preparation 20

Preparation of (E)-3-(2-oxo-2,3-dihydro-1H-indol-5-yl)acrylic acid hydrochloride salt a) 3,3,5-Tribromo-1,3-dihydropyrrolo[2,3-b]pyridin-2-one To a solution of 7-azaindole (5.0 g, 42.3 mmole) in $H_2O$ (210 mL) and tert-butanol (210 mL) at RT was added $Br_2$ (27 mL, 529.0 mmole) over 20 minutes. The reaction was stirred for 12 hr at RT and concentrated to an aqueous slurry. The reaction contents were made basic with solid $NaHCO_3$ and the remaining solid was filtered and washed with $H_2O$. The filtered mass was dried under high vacuum to give the title compound (14.0 g, 89%) as a brown solid: MS (ES) m/e 370 $(M+H)^+$.

b) 5-Bromo-1,3-dihydropyrrolo[2,3-b]pyridin-2-one

To a stirred solution of 3,3,5-tribromo-1,3-dihydropyrrolo[2,3-b]pyridin-2-one (2.0 g, 5.4 mmole) in acetic acid (50 mL) at RT was added Zn metal. The reaction became exothermic and was cooled by the use of an ice bath during the initial 30 minutes. After 5 hr the reaction was filtered through celite®, and the filter pad was washed with EtOAc. The filtrate was concentrated under vacuum and neutralized with saturated aqueous $NaHCO_3$ solution. The neutralized aqueous filtrate was then extracted with EtOAc (2×200 mL), and the combined organic extracts were dried over $Na_2SO_4$ and concentrated to a solid. The solid was washed with hexanes and dried under high vacuum to give the title compound (0.36 g, 32%): MS (ES) m/e 215 $(M+H)^+$. This was used without further purification.

c) tert-Butyl (E)-3-(2-oxo-2,3-dihydro-1H-indol-5-yl)acrylate

A solution of 5-bromo-1,3-dihydropyrrolo[2,3-b]pyridin-2-one (2.0 g, 9.49 mmole), tert-butyl acrylate (1.8 g, 14.1 mmole), $Pd(OAc)_2$ (0.32 g, 1.4 mmole), tri-ortho-tolylphosphine (0.57 g, 1.9 mmole), and diisopropylethylamine (4.9 mL, 28.2 mmole) in propionitrile (100 mL) and DMF (10 mL) was heated at reflux overnight. The dark mixture was filtered through celite®, and the filtrate was concentrated. Flash chromatography on silica (9:1 $CHCl_3/CH_3OH$ containing 5% $NH_4OH$) gave the title compound (0.80 g, 33%) as a light yellow solid. MS (ES) m/e 261 $(M+H)^+$.

d) (E)-3-(2-Oxo-2,3-dihydro-1H-indol-5-yl)acrylic acid hydrochloride salt

To a stirred solution of tert-butyl (E)-3-(2-oxo-2,3-dihydro-1H-indol-5-yl)acrylate (0.80 g, 3.1 mmole) in $CH_2Cl_2$ (50 mL) at RT was added trifluoroacetic acid (20 mL). After 1 hr the reaction solution was concentrated and the residue was dried under vacuum. An HCl solution (20 mL, 4 M in dioxane) was added and the mixture was concentrated under vacuum. The remaining solid was triturated with diethyl ether and filtered giving the title compound (0.74 g, 33%) as a white solid: MS (ES) m/e 205 $(M+H—HCl)^+$.

Preparation 21

Preparation of 1-ethyl-3-(methylaminomethyl)-1H-indole a) 3-[N-(Benzyloxycarbonyl)-N-methylaminomethyl]-1-ethyl-1H-indole According to the procedure of Preparation 17 (b), except substituting ethyl iodide (0.92 mL, 11.44 mmole) for the benzyl bromide, the title compound (0.90 g, 98%) was prepared as a white solid: MS (ES) m/e 323 (M+H)+.

b) 1-Ethyl-3-(methylaminomethyl)-1H-indole

According to the procedure of Preparation 17 (c), except substituting 3-[N-(benzyloxycarbonyl)-N-methylaminomethyl]-1-ethyl-1H-indole (0.90 g, 2.80 mmole) for the 3-[N-(benzyloxycarbonyl)-N-methylaminomethyl]-1-benzyl-1H-indole, the title compound (0.50 g, 94%) was prepared as a white solid: MS (ES) m/e 189 (M+H)+.

Preparation 22

Preparation of 1-isopropyl-3-(methylaminomethyl)-1H-indole a) 3-[N-(Benzyloxycarbonyl)-N-methylaminomethyl]-1-isopropyl-1H-indole According to the procedure of Preparation 17 (b), except substituting isopropyl iodide (1.34 mL, 11.84 mmole) for the benzyl bromide, the title compound (0.99 g, 99%) was prepared as a white solid: MS (ES) m/e 337 (M+H)+.

b) 1-ethyl-3-(methylaminomethyl)-1H-indole

According to the procedure of Preparation 17 (c), except substituting 3-[N-(Benzyloxycarbonyl)-N-methylaminomethyl]-1-isopropyl-1H-indole (0.99 g, 2.98 mmole) for the 3-[N-(Benzyloxycarbonyl)-N-methylaminomethyl]-1-benzyl-1H-indole, the title compound (0.49 g, 82%) was prepared as a white solid: MS (ES) m/e 405 (2M+H)+.

Preparation 23

Preparation of 1-acetyl-3-(methylaminomethyl)-1H-indole a) 1-Acetyl-3-(methylaminomethyl)indole According to the procedure of Preparation 16 (a), except substituting N-acetyl-3-indole carboxaldehyde (1.33 g, 7.10 mmole), the title compound (1.40 g, 99%) was prepared as a light yellow oil: MS (ES) m/e 203 (M+H)+.

Preparation 24

Preparation of N-(1H-indol-3-ylmethyl)-N-methylacrylamide a) N-(1H-Indol-3-ylmethyl)-N-methylacrylamide Acryloyl chloride (0.33 mL, 4.10 mmole) was added to a solution of 3-(methylaminomethyl)-1H-indole (0.60 g, 3.70 mmole) and Et₃N (1.03 mL, 7.40 mmole) in CH₂Cl₂ (30 mL) at 0° C. The reaction was held at 0° C. for ten minutes, then was stirred overnight at RT. The solution was concentrated in vacuo and the residue was diluted with water. The solution was extracted with ethyl acetate, and the combined organic extracts were washed with brine and dried over Na₂SO₄. The title compound (0.64 g, 80%) was obtained as a light yellow solid: MS (ES) m/e 215 (M+H)+.

Preparation 25

Preparation of N-(1-benzyl-1H-indol-3-ylmethyl)-N-methylacrylamide a) N-(1-Benzyl-1H-indol-3-ylmethyl)-N-methylacrylamide According to the procedure of Preparation 24 (a), except substituting 1-benzyl-3-(methylaminomethyl)-1H-indole (1.30 g, 5.20 mmole) for of 3-(methylaminomethyl)-1H-indole, the title compound (1.40 g, 89%) was a brown solid: MS (ES) m/e 305 (M+H)+.

Preparation 26

Preparation of N-[1-(2-dimethylamino)-1H-indol-3-ylmethyl]-N-methylacrylamide a) N-[1-(2-dimethylamino)-1H-indol-3-ylmethyl]-N-methylacrylamide According to the procedure of Preparation 25 (a), except substituting [1-(2-dimethylamino)]-3-(methylaminomethyl)-1H-indole (1.00 g, 2.74 mmole) for of 3-(methylaminomethyl)-1H-indole, the title compound (0.50 g, 79%) was a yellow solid: MS (ES) m/e 463 (2M+H)+.

Preparation 27

Preparation of 3-bromo-5,6,7,9-tetrahydro-pyrido[2,3-b]azepin-8-one a) 8-Benzylidene-5,6,7,8-tetrahydro-quinoline Benzaldehyde (3.59 mL, 35.30 mmole) was added to a solution of 5,6,7,8-tetrahydro-quinoline (4.70 g, 35.30 mmole) in acetic anhydride (25 mL), and the solution was heated to reflux under a nitrogen atmosphere. After overnight at reflux, the reaction was concentrated in vacuo. The residue was diluted with water and extracted with ethyl acetate. The combined organic extracts were washed with brine, dried over Na₂SO₄, and concentrated. The residue was purified by flash chromatography on silica gel (33% EtOAc/hexanes) to give the title compound (4.50 g, 58%) as a waxy yellow solid after drying in vacuo: MS (ES) m/e 222 (M+H)+.

b) 6,7-Dihydro-5H-quinolin-8-one

A solution of 8-benzylidene-5,6,7,8-tetrahydro-quinoline (4.30 g, 19.4 mmole) in CH₂Cl₂ (150 mL) was reacted with ozone at −78° C. for 30 minutes. Dimethyl sulfide (5 mL) was added, and the reaction was warmed to RT and stirred overnight. The mixture was concentrated in vacuo and the residue was purified by flash chromatography on silica gel (EtOAc). The title compound (2.20 g, 79%) was obtained as an off-white solid after drying in vacuo: MS (ES) m/e 148 (M+H)+.

c) 6,7-Dihydro-5H-quinolin-8-one oxime

According to the reported procedure (*J. Het. Chem.* 1978, 15, 249-251), 6,7-dihydro-5H-quinolin-8-one was reacted with hydroxylamine hydrochloride to afford the title compound (2.40 g, 96%) as a white solid after drying in vacuo: MS (ES) m/e 163 (M+H)+.

d) 6,7-Dihydro-5H-quinolin-8-one, O-toluenesulfonyloxime

According to the reported procedure (*J. Het. Chem.* 1978, 15, 249-251), 6,7-dihydro-5H-quinolin-8-one oxime was reacted with p-toluenesulfonyl chloride to afford the title compound (4.00 g, 85%) as a white solid after drying in vacuo: MS (ES) m/e 317 (M+H)+.

e) 5,6,7,9-Tetrahydro-pyrido[2,3-b]azepin-8-one

According to the reported procedure (*J. Het. Chem.* 1978, 15, 249-251), 6,7-dihydro-5H-quinolin-8-one, O-toluenef) 3-Bromo-5,6,7,9-tetrahydro-pyrido[2,3-b]azepin-8-one A 10% solution of bromine (0.57 mL, 11.1 mmole) in $CH_2Cl_2$ was added dropwise over 1 hr to a solution of 5,6,7,9-tetrahydro-pyrido[2,3-b]azepin-8-one (1.20 g, 7.4 mmole) in $CH_2Cl_2$ at RT. The mixture was stirred at RT overnight, then was concentrated in vacuo. The residue was diluted with 10% $Na_2CO_3$ and extracted with EtOAc. The combined organics were dried over $Na_2SO_4$ and concentrated. Flash chromatography on silica gel (EtOAc) gave the title compound (1.00 g, 56%) as a light yellow solid after drying in vacuo: MS (ES) m/e 241/243.

Preparation 28

Preparation of 5-bromo-2-(methylaminocarbonylmethyl)aminopyridine a) 5-Bromo-2-(tert-butoxycarbonyl)aminopyridine To a solution of 2-amino-5-bromopyridine (27.56 g, 159 mmole) in THF (150 mL) was added di-tert-butyl dicarbonate (38 g, 174 mmole). The reaction was gradually heated to reflux. Vigorous gas evolution was observed initially, which subsided after approximately 10 min. After 18 hr at reflux, the reaction was concentrated to dryness. The residue was triturated with 1:1 $Et_2O$/petroleum ether, filtered and dried under vacuum to give the title compound (34.79 g, 80%) as a white solid: $^1$H NMR (400 MHz, $CDCl_3$) δ 8.49 (s, 1 H), 8.37 (dd, 1 H), 7.94 (d, J=9.0 Hz, 1 H), 7.77 (dd, 1 H), 1.57 (s, 9 H).

b) 5-Bromo-2-[N-(tert-butoxycarbonyl)-N-(methoxycarbonylmethyl)amino]pyridine

To a solution of 5-bromo-2-(tert-butoxycarbonyl)aminopyridine (25.0 g, 91.5 mmole) in DMF (400 mL) was added portionwise with stirring a 60% dispersion of NaH in mineral oil (4.0 g, 100 mmole). The reaction was stirred for 15 min, then methyl bromoacetate (15 mL, 158.5 mmole) was added dropwise over 15 min. After stirring for 18 h at room temperature the reaction was concentrated to dryness. The remaining residue was taken up in EtOAc (200 mL) and $H_2O$ (200 mL) and filtered to remove insoluble material. The EtOAc phase was separated, washed with brine, dried ($Na_2SO_4$) and concentrated to dryness. Purification by flash chromatography on silica gel (10% EtOAc/Hexane) gave the title compound (16.56 g, 50%): $^1$H NMR (400 MHz, $CDCl_3$) δ 8.33 (s, 1 H), 7.73 (d, J=2.5 Hz, 1 H), 7.71 (d, J=2.5 Hz, 1 H), 4.69 (s, 2 H), 3.75 (s, 3 H), 1.51 (s, 9 H).

c) 5-Bromo-2-(methoxycarbonylmethyl)aminopyridine

A 50% solution of TFA in $CH_2Cl_2$ (200 mL) was added to 5-bromo-[N-(tert-butoxycarbonyl)-N-(methoxycarbonylmethyl)amino]pyridine (16.5 g, 46 mmole). After stirring for 45 min the reaction was concentrated to dryness, and the residue was diluted with 1.0 N $Na_2CO_3$ (300 mL). The mixture was extracted with EtOAc (300 mL), and the organic layer was washed with brine, dried ($Na_2SO_4$), and concentrated to dryness under vacuum. The title compound (11.32 g, 100%) was obtained as a white solid: $^1$H NMR (400 MHz, $CDCl_3$) δ 8.13 (d, J=2.3 Hz, 1 H), 7.48 (dd, 1 H), 6.40 (d, J=8.8 Hz, 1 H), 4.95 (br s, 1H), 4.12 (d, J=5.5 Hz, 2 H), 3.78 (s, 3H).

d) 5-Bromo-2-(methylaminocarbonylmethyl)aminopyridine

A solution of 2.0 M methylamine in MeOH (75 mL) was added to 5-bromo-2-(methoxycarbonylmethyl)aminopyridine (2.9 g, 12 mmole). The reaction was stirred for 24 h then was concentrated to dryness. The residue was triturated with 10% petroleum ether/$Et_2O$ (100 mL), then was collected and dried under vacuum to give the title compound (2.96 g, 100%) as an off-white solid: MS (ES) m/e 244.2 (M+H)$^+$.

Preparation 29

Preparation of methyl 2-amino-5-bromonicotinate a) Methyl 2-aminonicotinate

Concentrated $H_2SO_4$ (20 mL, 360 mmole) was added dropwise over 5 minutes to a suspension of 2-aminonicotinic acid (25 g, 181 mmole) in MeOH (400 mL), and the mixture was heated at reflux; a homogeneous solution formed within 5 min. After 72 h, the reaction was cooled to room temperature and concentrated under vacuum. The residue was basified with 1.0 N $Na_2CO_3$ (500 mL) (Gas evolution!) and extracted with EtOAc (500 mL). The organic layer was washed with brine, dried ($Na_2SO_4$), and concentrated to dryness to give the title compound (19.6 g, 71%) as a white solid: $^1$H NMR (400 MHz, $CDCl_3$) δ 8.22 (dd, 1 H), 8.13 (dd, 1 H), 6.63 (dd, 1 H), 6.30 (br s, 2 H), 3.89 (s, 3 H).

b) Methyl 2-amino-5-bromonicotinate

Bromine (0.7 mL, 14 mmole) was added dropwise to a stirred solution of methyl 2-aminonicotinate (2.0 g, 13 mmole) in HOAc (50 mL). A suspension formed within 30 min. The reaction was allowed to stir at room temperature for 2 h, then was concentrated under vacuum. The residue was triturated with 1.0 N $Na_2CO_3$ (50 mL) and the solid was collected by suction filtration. The solid was washed with $H_2O$ (50 mL) and dried under vacuum to give the title compound (2.95 g, 98%) as a pale yellow solid: $^1$H NMR (400 MHz, $CDCl_3$) δ 8.24 (d, J=2.5 Hz, 1 H), 8.23 (d, J=2.5 Hz, 1 H), 6.40 (br s, 2 H), 3.90 (s, 3 H).

Preparation 30

Preparation of (E)-3-[6-[N-methoxycarbonylmethyl)amino]pyridin-3-yl]acrylic acid hydrochloride salt a) tert-Butyl (E)-3-[6-[N-(methoxycarbonylmethyl)amino]pyridin-3-yl]acrylate A solution of 5-bromo-2-(methoxycarbonylmethyl)aminopyridine (4.69 g, 19.1 mmole, from Preparation 28 (c)), tert-butyl acrylate (11.2 mL, 76.5 mmole), DIEA (6.7 mL, 38.5 mmole), Pd(OAc)$_2$ (215 mg, 1 mmole), and P(o-tol)$_3$ (583 mg, 2 mmole) in propionitrile (100 mL) was purged with Ar, then was heated at reflux. After 18 h, the reaction was allowed to cool to room temperature then was concentrated to dryness. The residue was purified by flash chromatography on silica gel (40% EtOAc/hexane) to give the title compound (5.21 g, 93%) as a white solid: $^1$H NMR (400 MHz, $CDCl_3$) δ 8.19 (s, 1 H), 7.62 (dd, 1 H), 7.47 (d, J=16.0 Hz, 1 H), 6.48 (d, J=8.7 Hz, 1 H), 6.17 (d, J=15.9 Hz, 1 H), 5.21 (br s, 1 H), 4.20 (d, J=5.4 Hz, 2 H), 3.79 (s, 3 H), 1.52 (s, 1 H).

b) (E)-3-[6-[N-(Methoxycarbonylmethyl)amino]pyridin-3-yl]acrylic acid hydrochloride salt A solution of 50% TFA in $CH_2Cl_2$ (75 mL) was added to tert-butyl (E)-3-[6-[N-(methoxycarbonylmethyl)amino]pyridin-3-yl]acrylate (5.20 g, 17.8 mmole). The reaction was stirred at room temperature for 45 min then was concentrated under vacuum. The residue was taken up in 4.0 N HCl in dioxane (75 mL), stirred for 5 min, then concentrated to dryness under vacuum. The remaining solid was triturated with 1:1 $Et_2O$/petroleum ether, filtered and dried under vacuum to give the title compound (4.87 g, 100%) as a white solid: MS (ES) m/e 237.2 (M+H)$^+$.

Preparation 31

Preparation of (E)-3-(7-oxo-5,6,7,8-tetrahydro-1,8-naphthyridin-3-yl)acrylic acid hydrochloride salt a) tert-Butyl (E)-3-(7-oxo-5,6,7,8-tetrahydro-1,8-naphthyridin-3-yl)acrylate A solution of 6-bromo-3,4-dihydro-1H-1,8-naphthyridin-2-one (12.99 g, 57 mmole), tert-butyl acrylate (34 mL, 232 mmole), DIEA (21.2 mL, 122 mmole), Pd(OAc)$_2$ (1.3 g, 5.8 mmole) and P(o-tol)$_3$ (3.5 g, 11.5 mmole) in propionitrile (200 mL) and DMF (50 mL) was purged with Ar, then was heated at reflux. After 18 h the reaction was allowed to cool to room temperature and was concentrated to dryness. The residue was purified by flash chromatography on silica gel (2-4% MeOH/CHCl$_3$). The resulting residue was triturated with 1:1 Et$_2$O/petroleum ether, collected, and dried, and the resulting material was triturated with 1:1 MeOH/H$_2$O, collected, and dried, to give the title compound (7.09 g, 45%) as an off-white solid: $^1$H NMR (400 MHz, d$_6$-DMSO) δ 10.70 (s, 1 H), 8.35 (d, J=2.0 Hz, 1H), 8.04 (s, 1 H), 7.50 (d, J=16.0 Hz, 1 H), 6.51 (d, J=16.0 Hz, 1 H), 2.89 (t, 2 H), 2.53 (t, 2 H), 1.48 (s, 9H); MS (ES) m/e 275.2 (M+H)$^+$.

b) (E)-3-(7-oxo-5,6,7,8-tetrahydro-1,8-naphthyridin-3-yl)acrylic acid hydrochloride salt To tert-butyl (E)-3-(7-oxo-5,6,7,8-tetrahydro-1,8-naphthyridin-3-yl)acrylate (7.0 g, 25.5 mmole) was added 1:1 TFA/CH$_2$Cl$_2$ (100 mL). The reaction was stirred for 30 min, then was concentrated under vacuum. The residue was suspended in 4 N HCl/dioxane (100 mL), triturated, and concentrated to dryness. The resulting solid was triturated with Et$_2$O, collected, and dried under vacuum to give the title compound (6.55 g, 100%) as a off-white solid: $^1$H NMR (400 MHz, d$_6$-DMSO) δ 10.72 (s, 1 H), 8.35 (d, J=2.0 Hz, 1 H), 8.04 (s, 1 H), 7.54 (d, J=16.0 Hz, 1 H), 6.51 (d, J=16.0 Hz, 1 H), 2.91 (t, 2 H), 2.53 (t, 2 H); MS (ES) m/e 219.0 (M+H)$^+$.

Preparation 32

Preparation of N-methyl-N-(1-methyl-1H-pyrrolo[2,3-b]pyridin-ylmethyl)acrylamide A solution of acryloyl chloride (0.43 g, 5.58 mmole) in CH$_2$Cl$_2$ (10 mL) was added dropwise with stirring to a solution of 1-methyl-3-(methylaminomethyl)-1H-pyrrolo[2,3-b]pyridine (0.93 g, 5.28 mmole) and triethylamine (0.8 mL, 5.8 mmole) in CH$_2$Cl$_2$ (40 mL) at 0° C. under N$_2$. The reaction was allowed to warm to RT and stir for 1 hr, then was concentrated in vacuo. The residue was dissolved in 10% NaOH and extracted with CH$_2$Cl$_2$ (3×20 mL). The extracts were dried (MgSO$_4$), filtered, and concentrated. The residual oil was flash chromatographed on silica gel (5% MeOH/CH$_2$Cl$_2$) to give the title compound (1.0 g, 80%) as a colorless oil: MS (ES) m/e 216 (M+H)$^+$.

Preparation 33

Preparation of 7-fluoro-1-methyl-3-(methylaminomethyl)-1H-indole a) 7-Fluoro-1H-indole-3-carboxaldehyde According to the procedure of Preparation 11 (b), except substituting 7-fluoroindole (0.5 g, 3.7 mmole) for the 1,3 dimethylindole, the title compound (0.5 g, 83%) was prepared as a waxy solid: MS (ES) m/e 164 (M+H)$^+$.

b) 7-Fluoro-1-methyl-1H-indole-3-carboxaldehyde

According to the procedure of Preparation 9 (a), except substituting 7-fluoro-1H-indole-3-carboxaldehyde (0.5 g, 3.1 mmole) for the ethyl indole-2-carboxylate, the title compound (0.23 g, 43%) was prepared as a viscous oil: MS (ES) m/e 178 (M+H)$^+$.

c) 7-Fluoro-1-methyl-3-(methylaminomethyl)-1H-indole

According to the procedure of Preparation 11 (c), except substituting 7-fluoro-1-methyl-1H-indole-3-carboxaldehyde (0.23, 1.3 mmole) for the 1,3-dimethyl-1H-indole-2-carboxaldehyde, the title compound (0.18 g, 72%) was prepared as a viscous oil: MS (ES) m/e 193 (M+H)$^+$.

Preparation 34

Preparation of 6-fluoro-1-methyl-3-(methylaminomethyl)-1H-indole a) 6-Fluoro-1H-indole-3-carboxaldehyde According to the procedure of Preparation 11 (b), except substituting 6-fluoroindole (0.5 g, 3.7 mmole) for the 1,3-dimethylindole, the title compound (0.3 g, 50%) was prepared as a waxy solid: MS (ES) m/e 164 (M+H)$^+$.

b) 6-Fluoro-1-methyl-1H-indole-3-carboxaldehyde

According to the procedure of Preparation 9 (a), except substituting 6-fluoro-1H-indole-3-carboxaldehyde (0.3 g, 1.8 mmole) for the ethyl indole-2-carboxylate, the title compound (0.3 g, 94%) was prepared as a viscous oil: MS (ES) m/e 178 (M+H)$^+$.

c) 6-Fluoro-1-methyl-3-(methylaminomethyl)-1H-indole

According to the procedure of Preparation 11 (c), except substituting 6-fluoro-1-methyl-1H-indole-3-carboxaldehyde (0.3 g, 1.69 mmole) for the 1,3-dimethyl-1H-indole-2-carboxaldehyde, the title compound (0.11 g, 35%) was prepared as a viscous oil: MS (ES) m/e 193 (M+H)$^+$.

Preparation 35

Preparation of 5-fluoro-1-methyl-3-(methylaminomethyl)-1H-indole a) 5-Fluoro-1H-indole-3-carboxaldehyde According to the procedure of Preparation 11 (b), except substituting 5-fluoroindole (0.5 g, 3.7 mmole) for the 1,3-dimethylindole, the title compound (0.3 g, 50%) was prepared as a waxy solid: MS (ES) m/e 164 (M+H)$^+$.

b) 5-Fluoro-1-methyl-1H-indole-3-carboxaldehyde

According to the procedure of Preparation 9 (a), except substituting 5-fluoro-1H-indole-3-carboxaldehyde (0.3 g, 1.8 mmole) for the ethyl indole-2-carboxylate, the title compound (0.16 g, 50%) was prepared as a viscous oil: MS (ES) m/e 178 (M+H)$^+$.

c) 5-Fluoro-1-methyl-3-(methylaminomethyl)-1H-indole

According to the procedure of Preparation 11 (c), except substituting 5-fluoro-1-methyl-1H-indole-3-carboxaldehyde (0.3 g, 1.69 mmole) for the 1,3dimethyl-1H-2-carboxaldehyde, the title compound (0.11 g, 35%) was prepared as a viscous oil: MS (ES) m/e 193 (M+H)$^+$.

Preparation 36

Preparation of 4-fluoro-1-methyl-3-(methylaminomethyl)-1H-indole a) 4-Fluoro-1H-indole-3-carboxaldehyde According to the procedure of Preparation 11 (b), except substituting 4-fluoroindole (0.5 g, 3.7 mmole) for the 1,3- dimethylindole, the title compound (0.41 g, 68%) was prepared as a waxy solid: MS (ES) m/e 164 (M+H)+.

b) 4-Fluoro-1-methyl-1H-indole-3-carboxaldehyde

According to the procedure of Preparation 9 (a), except substituting 4-fluoro-1H-indole-3-carboxaldehyde (0.41 g, 2.5 mmole) for the ethyl-indole-2-carboxylate, the title compound (0.24 g, 54%) was prepared as a viscous oil: MS (ES) m/e 178 (M+H)+.

c) 4-Fluoro-1-methyl-3-(methylaminomethyl)-1H-indole

According to the procedure of Preparation 11 (c), except substituting 4-fluoro-1-methyl-1H-indole-3-carboxaldehyde (0.3 g, 1.69 mmole) for the 1,3-dimethyl-1H-indole-2-carboxaldehyde, the title compound (0.2 g, 77%) was prepared as a viscous oil: MS (ES) m/e 193 (M+H)+.

Preparation 37

Preparation of (1-ethyl-5-fluoro-3-(methylaminomethyl)-1H-indole a) 5-Fluoro-1H-indole-3-carboxaldehyde According to the procedure of Preparation 11 (b), except substituting 5-fluoroindole (0.5 g, 3.7 mmole) for the 1,3-dimethylindole, the title compound (0.3 g, 50%) was prepared as a waxy solid: MS (ES) m/e 164 (M+H)+.

b) 1-Ethyl-5-fluoro-1H-indole-3-carboxaldehyde

According to the procedure of Preparation 9 (a), except substituting 5-fluoro-1H-indole-3-carboxaldehyde (0.41 g, 2.5 mmole) for the ethylindole-2-carboxylate, the title compound (0.20 g, 57%) was prepared as a viscous oil: MS (ES) m/e 191 (M+H)+.

c) 1-Ethyl-5-fluoro-3-(methylaminomethyl)-1H-indole

According to the procedure of Preparation 11 (c), except substituting 1-ethyl-5-fluoro-1H-indole-3-carboxaldehyde (0.2 g, 1.9 mmole) for the 1,3-dimethyl-1H-indole-2-carboxaldehyde, the title compound (0.1 g, 50%) was prepared as a viscous oil: MS (ES) m/e 207 (M+H)+.

Preparation 38

Preparation of 4,6-dichloro-1-methyl-2-(methylaminomethyl)-1H-indole a) Ethyl 4,6-dichloro-1-methyl-1H-indole-2-carboxylate NaH (60% dispersion in mineral oil, 0.24 g, 6 mmole) was washed with hexanes, then was suspended in anhydrous DMF (16 mL). The mixture was cooled to 0° C., and ethyl 4,6-dichloroindole-2-carboxylate (1.03 g, 4 mmole) was added. After 2-3 min, iodomethane (1.3 mL, 20 mmole) was added, and the mixture was warmed to RT. The mixture became thick, and stirring became difficult for several minutes. After 0.5 hr, the reaction was cooled to 0° C. and quenched with 10% NH$_4$Cl (2 mL). The mixture was concentrated to dryness, and the residue was partitioned between Et$_2$O (50 mL) and H$_2$O (10 mL). The layers were separated and the organic layer was washed with H$_2$O (5 mL), dried (MgSO$_4$), and filtered, and the filter pad was washed with a little CH$_2$Cl$_2$. Concentration afforded the title compound (1.06 g, 97%) as an off-white solid: $^1$H NMR (400 MHz, CDCl$_3$) δ 7.34 (s, 1 H), 7.30 (s, 1 H), 7.17 (d, J=1.5 Hz, 1 H), 4.39 (q, J=7.1 Hz, 2 H), 4.05 (s, 3 H), 1.42 (t, J=7.1 Hz, 3 H); MS (ES) m/e 272 and 274 (M+H)+.

b) N,1-Dimethyl-4,6-dichloro-1H-indole-2-carboxamide

A suspension of ethyl 4,6-dichloro-1-methyl-1H-indole-2-carboxylate (1.06 g, 3.90 mmole) in 2.0 M CH$_3$NH$_2$/CH$_3$OH (40 mL) in a sealed pressure bottle was heated in an oil bath preset at 50° C. A homogeneous solution formed within 2.5 hr. The reaction was kept at 50° C. for 17.5 hr, during which time a solid precipitated. The mixture was cooled to RT and poured into H$_2$O (40 mL). The resulting mixture was concentrated on the rotavap to remove the methanol, and the solid was collected by suction filtration. This was washed with plenty of H$_2$O and dried in high vacuum at 45-50° C. to afford the title compound (0.99 g, 99%) as an off-white solid: $^1$H NMR (400 MHz, CDCl$_3$) δ 7.29 (s, 1 H), 7.16 (d, J=1.5 Hz, 1 H), 6.86 (s, 1 H), 6.21 (br s, 1 H), 4.02 (s, 3 H), 3.02 (d, J=4.9 Hz, 3 H); MS (ES) m/e 257 and 259 (M+H)+.

c) 4,6-Dichloro-1-methyl-2-(methylaminomethyl)-1H-indole

A solution of 2.0 M BH$_3$.DMS in THF (3.6 mL, 7.2 mmole) was added to a solution of N,1-dimethyl-1H-indole-2-carboxamide (0.74 g, 2.88 mmole) in anhydrous THF (25 mL), and the reaction was heated at reflux. After 18 hr, the reaction was cooled to 0° C. and quenched with MeOH (5 mL). The solution was warmed to RT, stirred for 0.5 hr, then concentrated on the rotavap. The residue was re-concentrated from MeOH, then was purified by flash chromatography on silica gel (5% MeOH/CHCl$_3$ containing 0.5% conc. NH$_4$OH). The title compound (197.5 mg, 28%) was obtained as a white solid: $^1$H NMR (400 MHz, CDCl$_3$) δ 7.19 (dd, J=1.5, 0.8 Hz, 1 H), 7.09 (d, J=1.5 Hz, 1 H), 6.45 (s, 1 H), 3.88 (s, 2 H), 3.74 (s, 3 H), 2.50 (s, 3 H); MS (ES) m/e 212 and 214 (M+H—CH$_3$NH$_2$)+.

Preparation 39

Preparation of 1,7-dimethyl-3-(methylaminomethyl)-1H-indole a) 1,7-Dimethyl-1H-indole According to the procedure of Preparation 13 (a), except substituting 7-methylindole for the 3-methylindole, the title compound (1.95 g, 90%) was obtained as a light-colored oil: MS (ES) m/e 146.2 (M+H)+.

b) 1,7-Dimethyl-1H-indole-3-carboxaldehyde

According to the procedure of Preparation 13 (b), except substituting 1,7-dimethylindole for the 1,2-dimethylindole, the title compound (1.85 g, 82%) was obtained as an off white solid: MS (ES) m/e 174.2 (M+H)+.

c) 1,7-Dimethyl-3-(methylaminomethyl)-1H-indole

According to the procedure of Preparation 13 (c), except substituting 1,7-dimethyl-1H-indole-3-carboxylate for the 1,3-dimethyl-1H-indole-2-carboxylate, the title compound (0.74 g, 98%) was obtained as an amber oil: MS (ES) m/e 189.2 (M+H)+.

Preparation 40

Preparation of 4-methoxy-1-methyl-3-(methylaminomethyl)-1H-indole a) 4-Methoxy-1-methyl-1H-indole-3-carboxaldehyde According to the procedure of Preparation 13 (b), except substituting 1-methyl-4-methoxyindole for the 1,2-dimethylindole, the title compound (2.17 g, 93%) was obtained as an off white solid: MS (ES) m/e 190.2 (M+H)+.

b) 4-Methoxy-1-methyl-3-(methylaminomethyl)-1H-indole

According to the procedure of Preparation 13 (c), except substituting 1-methyl-4-methoxy-1H-indole-3-carboxaldehyde for the 1,3-dimethyl-1H-indole-2-carboxaldehyde, the title compound (2.0 g, 95%) was obtained as a white solid: MS (ES) m/e 205.2 (M+H)+.

Preparation 41

Preparation of 5-methoxy-1-methyl-3-(methylaminomethyl)-1H-indole a) 5-Methoxy-1-methyl-1H-indole-3-carboxaldehyde According to the procedure of Preparation 13 (a), except substituting 5-methoxy-1H-indole-3-carboxaldehyde for the 3-methyl-1H-indole-3-carboxaldehyde, the title compound (0.86 g, 92%) was obtained as a light tan solid: MS (ES) m/e 190.2 (M+H)$^+$.

b) 5-Methoxy-1-methyl-3-(methylaminomethyl)-1H-indole

According to the procedure of Preparation 13 (c), except substituting 5-methoxy-1-methyl-1H-indole-3-carboxaldehyde for the 1,3-dimethyl-1H-indole-2-carboxaldehyde, the title compound (0.85 g, 98%) was obtained as a light yellow oil: MS (ES) m/e 205.2 (M+H)$^+$.

Preparation 42

Preparation of 7-methoxy-1-methyl-3-(methylaminomethyl)-1H-indole a) 7-Methoxy-1-methyl-1H-indole According to the procedure of Preparation 13 (a), except substituting 7-methoxyindole for 3-methylindole, the title compound (1.55 g, 96%) was obtained as a tan solid: MS (ES) m/e 162.2 (M+H)$^+$.

b) 7-Methoxy-1-methyl-1H-indole-3-carboxaldehyde

According to the procedure of Preparation 13(b), except substituting 7-methoxy-1-methyl-1H-indole for the 1,2-dimethylindole, the title compound (1.6 g, 91%) was obtained as an off white solid: MS (ES) m/e 190.2 (M+H)$^+$.

c) 7-Methoxy-1-methyl-3-(methylaminomethyl)-1H-indole

According to the procedure of Preparation 13(c), except substituting 7-methoxy-1-methyl-1H-indole-3-carboxaldehyde for the 1,3-dimethyl-1H-indole-2-carboxaldehyde, the title compound (1.6 g, 94%) was obtained as an amber oil: MS (ES) m/e 205.2 (M+H)$^+$.

Preparation 43

Preparation of 7-chloro-1-methyl-3-(methylaminomethyl)-1H-indole a) 7-Chloro-1-methyl-1H-indole According to the procedure of Preparation 13 (a), except substituting 7-chloroindole for the 3-methylindole, the title compound (2.2 g, 100%) was obtained as a white solid: MS (ES) m/e 166.2 (M+H)$^+$.

b) 7-Chloro-1-methyl-1H-indole-3-carboxaldehyde

According to the procedure of Preparation 13 (b), except substituting 7-chloro-1-methyl-1H-indole for the 1,2-dimethylindole, title compound (2.1 g, 84%) was obtained as a white solid: MS (ES) m/e 194.0 (M+H)$^+$.

c) 7-Chloro-1-methyl-3-(methylaminomethyl)-1H-indole

According to the procedure of Preparation 13 (c), except substituting 7-chloro-1-methyl-1H-indole-3-carboxaldehyde for the 1,3-dimethyl-1H-indole-2-carboxaldehyde, the title compound (2.0 g, 93%) was obtained as an amber oil: MS (ES) m/e 209.2 (M+H)$^+$.

Preparation 44

Preparation of 6-chloro-1-methyl-3-(methylaminomethyl)-1H-indole a) 6-Chloro-1-methyl-1H-indole According to the procedure of Preparation 13 (a), except substituting 6-chloroindole for the 3-methylindole, the title compound (2.2 g, 100%) was obtained as a white solid: MS (ES) m/e 166.2.0 (M+H)$^+$.

b) 6-Chloro-1-methyl-1H-indole-3-carboxaldehyde

According to the procedure of Preparation 13 (b), except substituting 6-chloro-1-methyl-1H-indole for the 1,2-dimethylindole, title compound (2.2 g, 88%) was obtained as an amber oil: MS (ES) m/e 194.2 (M+H)$^+$.

c) 6-Chloro-1-methyl-3-(methylaminomethyl)-1H-indole

According to the procedure of Preparation 13 (c), except substituting 6-chloro-1-methyl-1H-indole-3-carboxaldehyde for the 1,3-dimethyl-1H-indole-2-carboxaldehyde, the title compound (2.1 g, 93%) was obtained as an amber oil: MS (ES) m/e 209.2 (M+H)$^+$.

Preparation 45

Preparation of 5-chloro-1-methyl-3-(methylaminomethyl)-1H-indole a) 5-Chloro-1-methyl-1H-indole According to the procedure of Preparation 13 (a), except substituting 5-chloroindole for the 3-methylindole, the title compound (2.0 g, 91%) was obtained as an amber oil: MS (ES) m/e 166.0 (M+H)$^+$.

b) 5-Chloro-1-methyl-1H-indole-3-carboxaldehyde

According to the procedure of Preparation 13 (b), except substituting 5-chloro-1-methyl-1H-indole for the 1,2-dimethylindole, title compound (2.0 g, 83%) was obtained as an white solid: MS (ES) m/e 194.0 (M+H)$^+$.

c) 5-Chloro-1-methyl-3-(methylaminomethyl)-1H-indole

According to the procedure of Preparation 13 (c), except substituting 5-chloro-1-methyl-1H-indole-3-carboxaldehyde for the, 3-dimethyl-1H-indole-2-carboxaldehyde, the title compound (2.1 g, 93%) was obtained as an amber oil: MS (ES) m/e 209.0 (M+H)$^+$.

Preparation 46

Preparation of 4-chloro-1-methyl-3-(methylaminomethyl)-1H-indole a) 4-Chloro-1-methyl-1H-indole According to the procedure of Preparation 13 (a), except substituting 4-chloroindole for the 3-methylindole, the title compound (2.2 g, 100%) was obtained as an amber oil: MS (ES) m/e 166.0 (M+H)$^+$.

b) 4-Chloro-1-methyl-1H-indole-3-carboxaldehyde

According to the procedure of Preparation 13 (b), except substituting 4-chloro-1-methyl-1H-indole for the 1,2-dimethylindole, title compound (1.9 g, 76%) was obtained as an off-white solid: MS (ES) m/e 194.0 (M+H)$^+$.

c) 4-Chloro-1-methyl-3-(methylaminomethyl)-1H-indole

According to the procedure of Preparation 13 (c), except substituting 4-chloro-1-methyl-1H-indole-3-carboxaldehyde for the 1,3-dimethyl-1H-indole-2-carboxaldehyde, the title compound (1.75 g, 78%) was obtained as a yellow solid: MS (ES) m/e 209.0 (M+H)$^+$.

Preparation 47

Preparation of 1,1-dimethyl-3-(methylaminomethyl)-3H-indene a) 1,1-Dimethyl-3H-indene-3-carboxaldehyde The title compound was obtained in quantitative yield according to established literature procedures (*Chem. Pharm. Bull.* 1986, 34, 390-395; *Tet. Lett.* 1993, 34, 2979): $^1$H NMR (400 MHz, CDCl$_3$) δ 10.05 (s, 1 H), 8.05 (d, 2 H), 7.35 (m, 4 H), 1.40 (s, 6 H).

b) 1,1-Dimethyl-3-(methylaminomethyl)-3H-indene

According to the procedure of Preparation 12, except substituting 1,1-dimethyl-3H-indene-3-carboxaldehyde for the 2-methylindole-3-carboxaldehyde, the title compound (3 g, 81%) was obtained as a reddish oil: MS (ES) m/e 188.2 (M+H)$^+$.

Preparation 48

Preparation of 7-hydroxy-1-methyl-3-(methylaminomethyl)-1H-indole a) 7-Benzyloxy-1-methyl-1H-indole According to the procedure of Preparation 13 (a), except substituting 7-benzyloxyindole for the 3-methylindole, the title compound (4.8 g, 100%) was obtained as an amber oil: MS (ES) m/e 238.0 (M+H)$^+$.

b) 7-Benzyloxy-1-methyl-1H-indole-3-carboxaldehyde

According to the procedure of Preparation 13 (b), except substituting 7-benzyloxy-1-methyl-1H-indole for the 1,2-dimethylindole, title compound (4.5 g, 85%) was obtained as an oil: MS (ES) m/e 266.0 (M+H)$^+$.

c) 7-Benzyloxy-1-methyl-3-(methylaminomethyl)-1H-indole

According to the procedure of Preparation 13 (c), except substituting 7-benzyloxy-1-methyl-1H-indole-3-carboxaldehyde for the 1,3-dimethyl-1H-indole-2-carboxaldehyde, the title compound (3.7 g, 88%) was obtained as an oil: MS (ES) m/e 281.2 (M+H)$^+$.

d) 7-Hydroxy-1-methyl-3-(methylaminomethyl)-1H-indole

According to the literature procedure (*J. Org. Chem.* 1978, 43, 4195-96), 7-benzyloxy-1-methyl-3-(methylaminomethyl)-1H-indole was hydrogenated to afford the title compound (300 mg, 79%) as a brown solid: MS (ES) m/e 191.2 (M+H)$^+$.

Preparation 49

Preparation of 3-(methylaminomethyl)-1,2,7-trimethyl-1H-indole a) 1,2,7-Trimethyl-1H-indole According to the procedure of Preparation 13 (a), except substituting 2,7-dimethylindole for the 3-methylindole, the title compound (960 mg, 87%) was obtained as an oil: MS (ES) m/e 160.2 (M+H)$^+$.

b) 1,2,7-Trimethylindole-3-carboxaldehyde

According to the procedure of Preparation 13 (b), except substituting 1,2,7-trimethyl-1H-indole for the 1,4-dimethylindole, the title compound (800 mg, 62%) was obtained as a light tan solid: MS (ES) m/e 188.2 (M+H)$^+$.

c) 3-(Methylaminomethyl)-1,2,7-trimethyl-1H-indole

According to the procedure of Preparation 13 (c) except substituting 1,2,7-trimethyl-1H-indole-3-carboxaldehyde for the 1,3-dimethyl-1H-indole-2-carboxaldehyde, the title compound (570 mg, 71%) was obtained as an oil which slowly crystallized: MS (ES) m/e 405.4 (2M+H)$^+$.

Preparation 50

Preparation of 7-chloro-3-(methylaminomethyl)-1H-indole a) 7-Chloro-1H-indole-3-carboxaldehyde According to the procedure of Preparation 13 (b), except substituting 7-chloroindole for the 1,2-dimethylindole, the title compound (0.48 g, 44%) was obtained as a white solid after recrystallization from hot EtOAc: MS (ES) m/e 180.0 (M+H)$^+$.

b) 7-Chloro-3-(methylaminomethyl)-1H-indole

According to the procedure of Preparation 13 (c), except substituting 7-chloro-1H-indole-3-carboxaldehyde for the 1,3-dimethyl-1H-indole-2-carboxaldehyde, the title compound (440 mg, 92%) was obtained as an off white solid: MS (ES) m/e 195.2 (M+H)$^+$.

Preparation 51

Preparation of 2-(methylaminomethyl)naphthalene

To a stirred solution of 40 wt % methylamine in H$_2$O (50 mL, 581 mmole) in THF (50 mL) at 0° C. was added 2-(bromomethyl)naphthalene (10 g, 43 mmole) in one portion. The reaction was allowed to warm to RT and stirred for 16 hr, then was then concentrated under vacuum. The residue was taken up in Et$_2$O and washed with 1.0 N NaOH then with brine, dried (Na$_2$SO$_4$), and concentrated to dryness. Purification by flash chromatography on silica gel (98:2 to 9:1 CHCl$_3$/methanol containing 5% NH$_4$OH) gave the title compound (3.95 g, 54%) as a clear oil: $^1$H NMR (400 MHz, CDCl$_3$) δ 7.85 (m, 3 H), 7.79 (s, 1 H), 7.49 (m, 3 H), 3.94 (s, 2 H), 2.53 (s, 3 H).

Preparation 52

Preparation of 3-(methylaminomethyl)quinoline

A solution of 3-quinolinecarboxaldehyde (1.5 g, 10 mmole), 2.0 M CH$_3$NH$_2$/MeOH (10 mL, 20 mmole), glacial AcOH (0.6 mL, 10 mmole), and NaBH$_3$CN (0.35 g, 11 mmole) in MeOH (20 mL) was stirred at RT overnight, then was concentrated in vacuo. The residue was diluted with 5% NaOH and extracted with CH$_2$Cl$_2$. The combined organic extracts were washed with brine, dried over MgSO$_4$, and concentrated. Flash chromatography on silica gel (10% MeOH/CH$_2$Cl$_2$) gave the title compound (0.83 g, 24%) as a slightly yellow viscous oil: MS (ES) m/e 173 (M+H)$^+$.

Preparation 53

Preparation of (E)-2-methyl-3-(7-oxo-5,6,7,8-tetrahydro-1,8-naphthyridin-3-yl)acrylic acid hydrochloride salt a) tert-Butyl (E)-2-methyl-3-(7-oxo-5,6,7,8-tetrahydro-1,8-naphthyridin-3-yl)acrylate According to the procedure of Preparation 31 (a), except substituting tert-butyl methacrylate (4.7 g, 33.2 mmole) for the tert-butyl acrylate, the title compound (2.7 g, 42%) was prepared as a yellow solid: MS (ES) m/e 289 (M+H)$^+$.

b) (E)-2-methyl-3-(7-oxo-5,6,7,8-tetrahydro-1,8-naphthyridin-3-yl)acrylic acid hydrochloride salt According to the procedure of Preparation 31 (b), except substituting tert-butyl (E)-2-methyl-3-(7-oxo-5,6,7,8-tetrahydro-1,8-naphthyridin-3-yl)acrylate (2.7 g, 9.3 mmole) for the tert-butyl (E)-3-(7-oxo-5,6,7,8-tetrahydro-1,8-naphthyridin-3-yl)acrylate, the title compound (2.5 g, 99%) was prepared as a white solid: MS (ES) m/e 232 (M+H)+.

Preparation 54

Preparation of (E)-3-methyl-3-(7-oxo-5,6,7,8-tetrahydro-1,8-naphthyridin-3-yl)acrylic acid hydrochloride salt a) tert-Butyl (E)-3-methyl-3-(7-oxo-5,6,7,8-tetrahydro-1,8-naphthyridin-3-yl)acrylate According to the procedure of Preparation 31 (a), except substituting tert-butyl crotonate (4.7 g, 33.2 mmole) for the tert-butyl acrylate, the title compound (3.7 g, 58%) was prepared as a yellow solid: MS (ES) m/e 289 (M+H)+.

b) (E)-3-methyl-3-(7-oxo-5,6,7,8-tetrahydro-1,8-naphthyridin-3-yl)acrylic acid hydrochloride salt According to the procedure of Preparation 31 (b), except substituting tert-butyl (E)-3-methyl-3-(7-oxo-5,6,7,8-tetrahydro-1,8-naphthyridin-3-yl)acrylate (3.7 g, 12.8 mmole) for the tert-butyl (E)-3-(7-oxo-5,6,7,8-tetrahydro-1,8-naphthyridin-3-yl)acrylate, the title compound (3.4 g, 99%) was prepared as a white solid: MS (ES) m/e 232 (M+H)+.

Preparation 55

Preparation of 7-bromo-4-methyl-1,2,4,5-tetrahydropyrido[2,3-e]-1,4-diazepin-3-one a) 5-Bromo-3-[N-(tert-butoxycarbonyl)-N-methylaminomethyl]-2-[N-(tert-butoxycarbonyl)amino]pyridine To a solution of 2-amino-5-bromo-3-(methylaminomethyl)pyridine (3.8 g, 17.6 mmole), from Preparation 5 (a), in THF was added di-tert-butyl dicarbonate (8.8 g, 40.5 mmole). The reaction was heated to reflux for 12 hr then was concentrated under vacuum. Flash chromatography on silica gel (1:1 hexanes/EtOAc) gave the title compound (6.2 g, 85%) as a white waxy solid: MS (ES) m/e 416 (M+H)+.

b) 5-Bromo-2-[(ethoxycarbonyl)methylamino]-3-(methylaminomethyl)-2-[N-(tert-butoxycarbonyl)amino]pyridine bis-trifluoroacetic acid salt To a suspension of 60% NaH (0.46 g, 11.5 mmole) in THF (100 mL) at RT was added 5-bromo-3-[N-(tert-butoxycarbonyl)-N-methylaminomethyl]-2-[N-(tert-butoxycarbonyl) amino]pyridine (4.0 g, 9.61 mmole). After 30 min, ethyl bromoacetate (1.8 g, 10.6 mmole) was added. The reaction was stirred at RT for 12 hr, then was quenched with $H_2O$ (5 mL) and concentrated. The residue was dissolved in EtOAc (200 mL), and the solution was washed with $H_2O$ (100 mL), dried over $Na_2SO_4$, and concentrated under high vacuum to a light yellow solid. This was dissolved in $CH_2Cl_2$ (50 mL) and trifluoroacetic acid (20 mL). After 2 hr, the reaction was concentrated under vacuum and the residue was purified flash chromatography on silica gel (95:5 $CHCl_3/CH_3OH$). The title compound (4.1 g, 80%) was obtained as a yellow solid: MS (ES) m/e 302 (M+H)+.

c) 7-Bromo-4-methyl-1,2,4,5-tetrahydropyrido[2,3-e]-1,4-diazepin-3-one

To a solution of 5-bromo-2-[(ethoxycarbonyl)methylamino]-3-(methylaminomethyl)-2-[N-tert-butoxycarbonyl) amino]pyridine bis-trifluoroacetic acid salt (4.1 g, 7.7 mmole) in toluene was added triethylamine (3.3 mL, 23.7 mmole). The reaction was heated at reflux for 72 hr then concentrated under vacuum. Flash chromatography on silica gel (9:1 $CHCl_3/CH_3OH$ containing 5% $NH_4OH$) gave the title compound (1.4 g, 72%) as a tan solid: MS (ES) m/e 256 (M+H)+.

Preparation 56

Preparation of (E)-3-(8-oxo-6,7,8,9-tetrahydro-5H-pyrido[2,3-b]azepin-3-0)-acrylic acid hydrochloride salt a) tert-butyl (E)-3-(8-oxo-6,7,8,9-tetrahydro-5H-pyrido[2,3-b]azepin-3-yl)acrylate A solution of 3-bromo-5,6,7,9-tetrahydro-pyrido[2,3-b] azepin-8-one (1.00 g, 4.15 mmole), tert-butyl acrylate (0.67 mL, 4.60 mmole), DIEA (1.45 mL, 8.30 mmole), Pd(OAc)$_2$ (0.09 g, 0.42 mmole) and P(o-tol)$_3$ (0.25 g, 0.85 mmole) in propionitrile (25 mL) was purged with N$_2$ and then heated at reflux overnight. The dark mixture was filtered through a pad of celite®, and the filter pad was rinsed with acetonitrile (250 mL). The filtrate was concentrated in vacuo, and the residue was purified by flash chromatography on silica gel (ethyl acetate). The title compound (0.70 g, 58%) was obtained as a light yellow solid after drying in vacuo: MS (ES) m/e 289 (M+H)+.

b) (E)-3-(8-oxo-6,7,8,9-tetrahydro-5H-pyrido[2,3-b]azepin-3-yl)-acrylic acid hydrochloride salt According to the procedure of Preparation 31 (b), except substituting tert-butyl (E)-3-(8-oxo-6,7,8,9-tetrahydro-5H-pyrido[2,3-b]azepin-3-yl)acrylate (0.70 g, 2.40 mmole) for the tert-butyl (E)-3-(7-oxo-5,6,7,8-tetrahydro-1,8-naphthyridin-3-yl)acrylate, the title compound (0.49 g, 77%) was obtained as an off-white solid after drying in vacuo: MS (ES) m/e 233 (M+H)+.

Preparation 57

Preparation of 1-(2-hydroxyethyl)-3-(methylaminomethyl)-1H-indole

According to the reported literature procedure (J. Org. Chem. 1998, 63, 6721-6726) except substituting 3-[N-(benzyloxycarbonyl)-N-methylaminomethyl]-1H-indole (3.70 g, 12.60 mmole) for the 5-bromoindole, the title compound (4.00 g, 93%) was obtained as a yellow solid after drying in vacuo: MS (ES) m/e 338 (M+H)+.

Preparation 58

Preparation of 2-chloro-1-methyl-2-(methylaminomethyl)-1H-indole a) 2-Chloro-1H-indole-3-carboxaldehyde To DMF (30 mL) with stirring at 0° C. was added dropwise phosphorus oxychloride (10 mL, 107 mmole) over 5 minutes. The reaction was stirred for an additional 15 minutes, then oxindole (6.0 g, 45 mmole) was added portionwise over 5 min. The reaction was allowed to warm to RT and stirred for 18 h then was carefully poured into ice water (350 mL). The solution was stirred for 6 h after which time a suspension formed. The solids were filtered off, washed with cold water, pressed dry and dried under vacuum to give the title compound (6.83 g, 84%) as a yellowish solid: $^1$H NMR (400 MHz, d$_6$-DMSO) δ 10.0 (s, 1 H), 8.05 (dd, 1 H), 7.43 (dd, 1 H), 7.23-7.31 (m, 2 H); MS (ES) m/e 179.0 (M+H)+.

b) 2-Chloro-1-methyl-1H-indole-3-carboxaldehyde

NaH (60% dispersion in mineral oil) (0.9 g, 22.5 mmole) was added portionwise over 5 min to a solution of 2-chloro-1H-indole-3-carboxaldehyde (3.8 g, 21.2 mmole) and iodomethane (1.5 mL, 24 mmole) in DMF (50 mL) with stirring at 0° C. The reaction was allowed to warm to RT and stir for 4 h, then was concentrated under vacuum. The remaining residue was taken up in EtOAc, and the solution was washed with water then brine, dried (MgSO$_4$), and concentrated to dryness. Trituration with 1:1 Et$_2$O/petroleum ether, filtration, and drying under vacuum gave the title compound (3.10 g, 76%) as an off-white solid: $^1$H NMR (400 MHz, CDCl$_3$) δ 10.12 (s, 1 H), 8.29 (m, 1 H), 7.33 (m, 3 H), 3.81 (s, 3 H); MS (ES) m/e 194.0 (M+H)$^+$.

c) 2-Chloro-1-methyl-2-(methylaminomethyl)-1H-indole

According to the procedure of Preparation 12, except substituting 2-chloro-1-methyl-1H-indole-3-carboxaldehyde (3.0 g, 15.5 mmole) for the 1-methylindole-3-carboxaldehyde, the title compound (2.91 g, 90%) was prepared as an oil: $^1$H NMR (400 MHz, CDCl$_3$) δ 7.60 (d, J=7.9 Hz, 1 H), 7.22 (m, 2 H), 7.13 (m, 1 H), 3.92 (s, 2 H), 3.71 (s, 3 H), 2.44 (s, 3 H).

Preparation 59

Preparation of 3-(benzhydrylideneamino)-6-bromo-3,4-dihydro-1H-1,8-naphthyridin-2-one NaH (60% dispersion in mineral oil, 1.2 g, 30 mmole) was added portionwise over 10 min to a solution of N-(diphenylmethylene)glycine ethyl ester (8.0 g, 30 mmole) in DMF (150 mL) with stirring under Ar at 0° C. The reaction was stirred for 15 min, then 2-amino-5-bromo-3-(bromomethyl)pyridine hydrobromide (5.0 g, 14.4 mmole) was added in one portion. The reaction was allowed to warm to RT and stir for 18 h, then was concentrated under vacuum. The remaining residue was taken up in EtOAc (150 mL), hexane (150 mL), and H$_2$O (150 mL). The resulting suspension was triturated and filtered, and the solid was dried under vacuum to give the title compound (3.27 g, 56%) as an off-white solid: $^1$H NMR (400 MHz, d$_6$-DMSO) δ 10.92 (s, 1 H), 8.23 (s, 1 H), 7.86 (s, 1 H), 7.26-7.55 (m, 10 H), 4.05 (dd, 1 H), 3.10 (t, 2 H); MS (ES) m/e 406.0 (M+H)$^+$.

Preparation 60

Preparation of 2-(methylaminomethyl)benzofuran

To a stirred solution of 2-benzofurancarboxaldehyde (2.22 g, 15.2 mmole) in MeOH (5 mL) was added 2 M methylamine in MeOH (15 mL), HOAc (0.86 mL, 15 mmole), and NaBH$_3$CN (1.0 g, 15.9 mmole). The reaction was stirred for 18 h at RT then concentrated under vacuum. The remaining residue was taken up in Et$_2$O, and the solution was washed with 1 N NaOH then brine, dried (Na$_2$SO$_4$), and concentrated to dryness. Purification by flash chromatography on silica gel (5% (5% NH$_4$OH in MeOH)/CHCl$_3$) gave the title compound (1.23 g, 50%) as a pale yellow oil: MS (ES) m/e 162.4 (M+H)$^+$.

Preparation 61

Preparation of methyl 1-methyl-3-(methylaminomethyl)-1H-indole-7-carboxylate a) Methyl 1-methyl-1H-indole-7-carboxylate According to the procedure of Preparation 9 (a), except substituting methyl indole-7-carboxylate for the ethyl indole-2-carboxylate, the title compound (2.4 g, 90%) was obtained as an oil: MS (ES) m/e 190.2 (M+H)$^+$.

b) N-Methyl-7-methoxycarbonyl-1H-indole-3-carboxaldehyde

According to the procedure of Preparation 13 (b), except substituting methyl 1-methyl-1H-indole-7-carboxylate for the 1,3-dimethylindole, the title compound (1.8 g, 70%) was obtained as a white solid: MS (ES) m/e 218.2 (M+H)$^+$.

c) Methyl 1-methyl-3-(methylaminomethyl)-1H-indole-7-carboxylate

According to the procedure of Preparation 12, except substituting 1-methyl-7-methoxycarbonyl-1H-indole 3-carboxaldehyde for the 2-methylindole-3-carboxaldehyde, the title compound (1.7 g, 92%) was obtained as an oil: MS (ES) m/e 233.2 (M+H)$^+$.

Preparation 62

Preparation of methyl 1-methyl-3-(methylaminomethyl)-1H-indole-6-carboxylate a) Methyl 1-methyl-1H-indole-6-carboxylate According to the procedure of Preparation 9 (a), except substituting methyl indole-6-carboxylate for the ethyl indole-2-carboxylate, the title compound (2.5 g, 95%) was obtained as white solid: MS (ES) m/e 190.2 (M+H)$^+$.

b) N-Methyl-7-methoxycarbonyl-1H-indole-3-carboxaldehyde

According to the procedure of Preparation 13 (b), except substituting methyl 1-methyl-1H-indole-6-carboxylate for the 1,3-dimethylindole, the title compound (2.6 g, 98%) was obtained as a white solid: MS (ES) m/e 218.2 (M+H)$^+$.

c) Methyl 1-methyl-3-(methylaminomethyl)-1H-indole-6-carboxylate

According to the procedure of Preparation 12, except substituting 1-methyl-7-methoxycarbonyl-1H-indole 3-carboxaldehyde for the 2-methylindole-3-carboxaldehyde, the title compound (1.9 g, 63%) was obtained as an oil: MS (ES) m/e 233.2 (M+H)$^+$.

Preparation 63

Preparation of 6-methoxy-1-methyl-3-(methylaminomethyl)-1H-indole a) 6-Methoxy-1-methyl-1H-indole According to the procedure of Preparation 9 (a), except substituting 6-methoxy-1H-indole for the ethyl indole-2-carboxylate, the title compound (2.3 g, 95%) was obtained as an oil: MS (ES) m/e 162.2 (M+H)$^+$.

b) 6-Methoxy-1-methyl-1H-indole-3-carboxaldehyde

According to the procedure of Preparation 13 (b), except substituting 6-methoxy-1-methyl-1H-indole for the 1,3-dimethylindole, the title compound (2.3 g, 82%) was obtained as a tan solid: MS (ES) m/e 190.2 (M+H)$^+$.

c) 6-Methoxy-1-methyl-3-(methylaminomethyl)-1H-indole

According to the procedure of Preparation 12, except substituting 6-methoxy-1-methyl-1H-indole-3-carboxaldehyde for the 2-methylindole-3-carboxaldehyde, the title compound (2.1 g, 87%) was obtained as an oil: MS (ES) m/e 205.2 (M+H)$^+$.

Preparation 64

Preparation of 7-fluoro-3-(methylaminomethyl)-1H-indole a) 7-Fluoro-1H-indole-3-carboxaldehyde According to the procedure of Preparation 13 (b), except substituting 7-fluoroindole (0.5 g, 3.7 mmole) for the 1,3-dimethylindole, the title compound (0.3 g, 55%) was prepared as a waxy solid: MS (ES) m/e 164 (M+H)$^+$.

b) 7-Fluoro-3-(methylaminomethyl)-1H-indole

According to the procedure of Preparation 13 (c), except substituting 7-fluoro-1H-indole-3-carboxaldehyde (0.5 g, 3.1 mmole) for the 1,3-dimethyl-1H-indole-2-carboxaldehyde, the title compound (0.5 g, 90%) was prepared as a viscous oil: MS (ES) m/e 179 (M+H)$^+$.

Preparation 65

Preparation of 4-fluoro-3-(methylaminomethyl)-1H-indole a) 4-Fluoro-1H-indole-3-carboxaldehyde According to the procedure of Preparation 13 (b), except substituting 4-fluoroindole (0.4 g, 2.45 mmole) for the 1,3-dimethylindole, the title compound (0.31 g, 72%) was prepared as a viscous oil: MS (ES) m/e 164 (M+H)$^+$.

b) 4-Fluoro-3-(methylaminomethyl)-1H-indole

According to the procedure of Preparation 13 (c), except substituting 4-fluoro-1H-indole-3-carboxaldehyde for the 1,3-dimethyl-1H-indole-2-carboxaldehyde, the title compound was prepared as a viscous oil: MS (ES) m/e 179 (M+H)$^+$.

Preparation 66

Preparation of 6-bromo-3-(2-methoxyethyl)-3,4-dihydro-1H-pyrido[2,3-d]pyrimidin-2-one a) 2-Amino-5-bromo-3-[(2-methoxyethyl)aminomethyl]pyridine 2-Methoxyethylamine (1.49 mL, 17.16 mmole) was added to a solution of 2-amino-5-bromo-3-(bromomethyl)pyridine hydrobromide (1.49 g, 4.29 mmole) and DIEA (2.24 mL, 12.87 mmole) in CH$_2$Cl$_2$ (10 mL) at RT. The reaction was stirred overnight then was concentrated in vacuo. The residue was diluted with water and the solution was extracted with ethyl acetate. The combined organic extracts were washed with brine, dried over Na$_2$SO$_4$, and concentrated to afford the title compound (1.00 g, 90%) as a light brown liquid after drying in vacuo: MS (ES) m/e 260/262 (M+H)$^+$.

b) 6-Bromo-3-(2-methoxyethyl)-3,4-dihydro-1H-pyrido[2,3-d]pyrimidin-2-one 1,1'-Carbonyldiimidazole (0.74 g, 4.60 mmole) was added to a solution of 2-amino-5-bromo-3-[(2-methoxyethyl)aminomethyl]pyridine (1.00 g, 3.80 mmole) in 1,2-dichloroethane (35 mL) at RT. The reaction was heated at 65° C. with stirring overnight, then was concentrated in vacuo. Flash chromatography on silica gel (5% MeOH/CHCl$_3$) gave title compound (0.90 g, 83%) as a yellow solid after drying in vacuo: MS (ES) m/e 286/288 (M+H)$^+$.

The following examples illustrate methods for preparing the biologically active compounds of this invention from intermediate compounds such as those described in the foregoing Preparations.

Example 1

Preparation of (E)-3-(2-aminopyrimidin-5-yl)-N-(2-methyl-1H-indol-3-ylmethyl)-N-methylacrylamide a) N-Methyl-N-(2-methyl-1H-indol-3-ylmethyl)acrylamide To a solution of 2-methyl-3-(methylaminomethyl)indole (1.5 g, 8.6 mmole) and triethylamine (1.7 g, 17.3 mmole) in CH$_2$Cl$_2$ at 5° C. under a nitrogen atmosphere was added acryloyl chloride (0.86 g, 9.48 mmole). After 1 hr the reaction solution was poured into H$_2$O (100 mL) and the layers were separated. The organic fraction was washed with H$_2$O (100 mL) followed by brine and then dried over Na$_2$SO$_4$. Concentration under vacuum gave the title compound as an orange oil which solidified under high vacuum: MS (ES) m/e 457 (2M+H)$^+$. This material was used without further purification.

b) (E)-3-(2-Aminopyrimidin-5-yl)-N-(2-methyl-1H-indol-3-ylmethyl)-N-methylacrylamide A solution of N-methyl-N-(2-methyl-1H-indol-3-ylmethyl)acrylamide (1.18 g, 6.5 mmole), 2-amino-5-bromopyrimidine (0.5 g, 2.9 mmole), Pd(OAc)$_2$ (0.11 g, 0.49 mmole), tri-ortho-tolylphosphine (0.17 g, 0.55 mmole), and diisopropylethylamine (1.5 mL, 8.6 mmole) in propionitrile (100 mL) and DMF (10 mL) was heated at reflux overnight. The dark mixture was filtered through celite®, and the filtrate was concentrated. Flash chromatography on silica gel (9:1 CHCl$_3$/CH$_3$OH containing 5% NH$_4$OH) gave the title compound (1.2 g, 65%): MS (ES) m/e 372 (M+H)$^+$.

Example 2

Preparation of (E)-N-methyl-N-(2-methyl-1H-indol-3-ylmethyl)-3-(3-methyl-2-oxo-1,2,3,4-tetrahydropyrido[2,3-d]pyrimidin-6-yl)acrylamide According to the procedure of Example 1 (b), except substituting 6-bromo-3-methyl-3,4-dihydro-1H-pyrido[2,3-d]pyrimidin-2-one (1.2 g, 5.0 mmole) for the 2-amino-5-bromopyrimidine, the title compound (73%) was prepared as a light yellow solid: MS (ES) m/e 390 (M+H)$^+$.

Example 3

Preparation of (E)-N-methyl-N-(1-methyl-1H-indol-3-ylmethyl)-3-(3-methyl-2-oxo-1,2,3,4-tetrahydropyrido[2,3-d]pyrimidin-6-yl)acrylamide a) N-Methyl-N-(1-methyl-indol-3-ylmethyl)acrylamide According to the procedure of Example 1 (a), except substituting 1-methyl-3-(methylaminomethyl)indole for the 2-methyl-3-(methylaminomethyl)indole, the title compound (1.7 g, 99%) was prepared as an orange oil that solidified under vacuum: MS (ES) m/e 229 (M+H)$^+$. This material was used without further purification.

b) (E)-N-methyl-N-(1-methyl-1H-indol-3-ylmethyl)-3-(3-methyl-2-oxo-1,2,3,4-tetrahydropyrido[2,3-d]pyrimidin-6-yl)acrylamide According to the procedure of Preparation 1 (b), except substituting N-methyl-N-(1-methyl-indol-3-ylmethyl)acrylamide (1.7 g, 7.5 mmole) for N-methyl-N-(2-methyl-1H-indol-3-ylmethyl)acrylamide, the title compound (70%) was prepared as a light yellow solid: MS (ES) m/e 390 (M+H)$^+$.

Example 4

Preparation of (E)-N-methyl-N-(2-methyl-1H-indol-3-ylmethyl)-3-(2-oxo-2,3-dihydro-1H-pyrrolo[2,3-b]pyridin-5-yl)acrylamide To a solution of (E)-3-(2-oxo-2,3-dihydro-1H-indol-5-yl)acrylic acid hydrochloride salt (0.50 g, 2.1 mmole), hydroxybenzotriazole monohydrate (0.31 g, 2.3 mmole), diisopropylethylamine (0.80 mL, 4.6 mmole), and 2-methyl-3-(methylaminomethyl)indole (0.40 g, 2.3 mmole) in DMF (50 mL) at RT was added EDC (0.46, 2.3 mmole). After 12 hr the reaction solution was concentrated under vacuum and the residue was purified by flash chromatography on silica gel (9:1 $CHCl_3/CH_3OH$ containing 5% $NH_4OH$) to give the title compound (0.66 g, 88%) as a light yellow solid: MS (ES) m/e 361 $(M+H)^+$.

Example 5

Preparation of (E)-3-(3H-imidazo[4,5-b]pyridin-6-yl)-N-methyl-N-(1-methyl-1H-indol-3-ylmethyl)acrylamide According to the procedure of Example 4, except substituting (E)-3-(3H-imidazo[4,5-b]pyridin-6-yl)acrylate (0.14 g, 0.74 mmole), from Preparation 6, for the (E)-3-(2-oxo-2,3-dihydro-1H-indol-5-yl)acrylic acid hydrochloride salt, and substituting 1-methyl-3-(methylaminomethyl)indole (0.14 g, 0.81 mmole) for the 2-methyl-3-(methylaminomethyl)-1H-indole, the title compound (0.23 g, 89%) was prepared as a light yellow solid: MS (ES) m/e 346 $(M+H)^+$.

Example 6

Preparation of (E)-3-(3,4-dihydro-2H-pyrido[3,2-b]-1,4-oxazin-7-yl)-N-methyl-N-(1-methyl-1H-indol-3-ylmethyl)acrylamide According to the procedure of Example 4, except substituting (E)-3-(3,4-dihydro-2H-pyrido[3,2-b][1,4]oxazin-7-yl)acrylic acid (0.11 g, 0.53 mmole), from Preparation 7, for the (E)-3-(2-oxo-2,3-dihydro-1H-indol-5-yl)acrylic acid hydrochloride salt, and substituting 1-methyl-3-(methylaminomethyl)indole (0.10 g, 0.59 mmole) for the 2-methyl-3-(methylaminomethyl)-1H-indole, the title compound (0.16 g, 82%) was prepared as a light yellow solid: MS (ES) m/e 363 $(M+H)^+$.

Example 7

Preparation of (E)-3-[6-amino-5-[[N-methyl-N-(2-methyl-1H-indol-3-ylmethyl)amino]carbonylethyl]pyridin-3-yl]-N-methyl-N-(2-methyl-1H-indol-3-ylmethyl)acrylamide a) Ethyl (E)-3-(7-oxo-5,6,7,8-tetrahydro-1,8-naphthyridin-3-yl)acrylate A solution of 6-bromo-3,4-dihydro-1H-1,8-naphthyridin-2-one (5.0 g, 21.9 mmole), from Preparation 4, ethyl acrylate (3.3 g, 32.9 mmole), $Pd(OAc)_2$ (1.1 g, 0.74 mmole), tri-ortho-tolylphosphine (1.3 g, 4.4 mmole), and diisopropylethylamine (11.4 mL, 65.7 mmole) in propionitrile (200 mL) and DMF (25 mL) was heated at reflux overnight. The dark mixture was filtered through celite®, and the filtrate was concentrated. Flash chromatography on silica gel (9:1 $CHCl_3/CH_3OH$ containing 5% $NH_4OH$) gave the title compound (3.0 g, 59%) as a light yellow solid: MS (ES) m/e 233 $(M+H)^+$.

b) (E)-3-[6-Amino-5-(2-carboxyethyl)pyridin-3-yl]acrylic acid hydrochloride salt Ethyl (E)-3-(7-oxo-5,6,7,8-tetrahydro-1,8-naphthyridin-3-yl)acrylate (1.54 g, 6.6 mmole) was dissolved in acetic acid (25 mL) and concentrated hydrochloric acid (25 mL) and the solution was heated to 100° C. After 6 hr the solution was concentrated and the residue was dried under high vacuum. The resulting solid was triturated with diethyl ether and filtered to give a 1.46 g of a mixture of (E)-3-(7-oxo-5,6,7,8-tetrahydro-1,8-naphthyridin-3-yl)acrylic acid hydrochloride salt (82%) and the title compound (18%), both as white solids: MS (ES) m/e 218 (M+H)+(major) and MS (ES) m/e 236 (M+H)+(minor). This mixture was used without further purification.

c) (E)-3-[6-Amino-5-[[N-methyl-N-(2-methyl-1H-indol-3-ylmethyl)amino]carbonylethyl]pyridin-3-yl]-N-methyl-N-(2-methyl-1H-indol-3-ylmethyl)acrylamide According to the procedure of Example 4, except substituting a mixture (1.46 g) of (E)-3-[6-amino-5-(2-carboxyethyl)pyridin-3-yl]acrylic acid hydrochloride salt and (E)-3-(7-oxo-5,6,7,8-tetrahydro-1,8-naphthyridin-3-yl)acrylic acid hydrochloride salt for the (E)-3-(2-oxo-2,3-dihydro-1H-indol-5-yl)acrylic acid hydrochloride salt, the title compound (0.47 g) was prepared as a light yellow solid: MS (ES) m/e 549 $(M+H)^+$. (E)-N-Methyl-N-(2-methyl-1H-indol-3-ylmethyl)-3-(7-oxo-5,6,7,8-tetrahydro-1,8-naphthyridin-3-yl)acrylamide (1.56 g) was also obtained as a light yellow solid: MS (ES) m/e 375 $(M+H)^+$.

Example 8

Preparation of (E)-3-(6-aminopyridin-3-yl)-N-(1-ethyl-1H-indol-3-ylmethyl)-N-methylacrylamide EDC (0.56 g, 2.93 mmole) was added to a solution of (E)-3-(6-aminopyridin-3-yl)acrylic acid (0.48 g, 2.93 mmole), 1-ethyl-3-(methylaminomethyl)-1H-indole (0.50 g. 2.66 mmole), $HOBt.H_2O$ (0.40 g, 2.93 mmole) and diisopropylethylamine (0.93 mL, 5.32 mmole) in DMF (30 mL) at RT. The reaction was stirred overnight then was concentrated in vacuo. The residue was diluted with water and extracted with ethyl acetate. The combined organic extracts were washed with brine and dried over $Na_2SO_4$. Flash chromatography on silica gel (10% $MeOH/CHCl_3$) gave title compound (0.46 g, 52%) as a yellow solid after drying in vacuo: MS (ES) m/e 335 $(M+H)^+$.

Example 9

Preparation of (E)-3-(6-aminopyridin-3-yl)-N-(1-isopropyl-1H-indol-3-ylmethyl)-N-methylacrylamide EDC (0.51 g, 2.64 mmole) was added to a solution of (E)-3-(6-aminopyridin-3-yl)acrylic acid (0.43 g, 2.64 mmole), 1-isopropyl-3-(methylaminomethyl)indole (0.49 g, 2.40 mmole), $HOBt.H_2O$ (0.36 g, 2.64 mmole) and diisopropylethylamine (0.84 mL 4.80 mmole) in DMF (40 mL) at RT. The reaction was stirred overnight then was concentrated in vacuo. The residue was diluted with water and extracted with ethyl acetate. The combined organic extracts were washed with brine and dried over $Na_2SO_4$. Flash chromatography on silica gel (10% $MeOH/CHCl_3$) gave the title compound (0.49 g, 58%) as a yellow solid after drying in vacuo: MS (ES) m/e 349 $(M+H)^+$.

Example 10

Preparation of (E)-3-(6-aminopyridin-3-yl)-N-(1H-indol-3-ylmethyl)-N-methylacrylamide EDC (1.03 g, 5.40 mmole) was added to a solution of (E)-3-(6-aminopyridin-3-yl)acrylic acid (0.89 g, 5.40 mmole), 1-acetyl-3-(methylaminomethyl)indole (1.00 g, 4.95 mmole), HOBt.H$_2$O (0.73 g., 5.40 mmole) and diisopropylethylamine (1.72 mL, 9.90 mmole) in DMF (50 mL) at RT. The reaction was stirred overnight then was concentrated in vacuo. The residue was diluted with water and extracted with ethyl acetate. The combined organic extracts were washed with brine and dried over Na$_2$SO$_4$. Flash chromatography on silica gel (5% MeOH/CHCl$_3$) gave the title compound (0.90 g, 52%) as a light yellow solid after drying in vacuo: MS (ES) m/e 307 (M+H)$^+$.

Example 11

Preparation of (E)-N-(1H-indol-3-ylmethyl)-N-methyl-3-(7-oxo-5,6,7,8-tetrahydro-1,8-naphthyridin-3-yl)acrylamide A solution of 6-bromo-3,4-dihydro-1H-1,8-naphthyridin-2-one (0.64 g, 2.80 mmole), N-(1H-indol-3-ylmethyl)-N-methylacrylamide (0.60 g, 2.80 mmole), Pd(OAc)$_2$ (0.06 g, 0.28 mmole), tri-ortho-tolylphosphine (0.17 g, 0.56 mmole) and diisopropylethylamine (0.73 mL, 4.2 mmole) in propionitrile (50 mL) was deoxygenated, then was heated to reflux under N$_2$ overnight. The dark mixture was filtered through a pad of celite®, and the filter pad was rinsed with acetonitrile (250 mL). The filtrate was concentrated in vacuo, and the residue was purified by flash chromatography on silica gel (10% MeOH/CHCl$_3$). The title compound (0.37 g, 37%) was obtained as a light yellow solid after drying in vacuo: MS (ES) m/e 361 (M+H)$^+$.

Example 12

Preparation of (E)-N-(1-benzyl-1H-indol-3-ylmethyl)-N-methyl-3-(7-oxo-5,6,7,8-tetrahydro-1,8-naphthyridin-3-yl)acrylamide A solution of 6-bromo-3,4-dihydro-1H-1,8-naphthyridin-2-one (1.05 g, 4.60 mmole), N-(1-benzyl-1H-indol-3-ylmethyl)-N-methyl-acrylamide (1.40 g, 4.60 mmole), Pd(OAc)$_2$ (0.10 g, 0.46 mmole), tri-ortho-tolylphosphine (0.28 g, 0.92 mmole) and diisopropylethylamine (1.20 mL 6.90 mmole) in propionitrile (75 mL) was deoxygenated, then was heated to reflux under a N$_2$ overnight. The dark mixture was filtered through a pad of celite®, and the filter pad was rinsed with acetonitrile (300 mL). The filtrate was concentrated in vacuo, and the residue was purified by flash chromatography on silica gel (5% MeOH/CHCl$_3$). The title compound (0.70 g. 35%) was obtained as a light yellow solid after drying in vacuo: MS (ES) m/e 451 (M+H)$^+$.

Example 13

Preparation of (E)-N-[1-(2-dimethylaminoethyl)-1H-indol-3-ylmethyl]-N-methyl-3-(7-oxo-5,6,7,8-tetrahydro-1,8-naphthyridin-3-yl)acrylamide A solution of 6-bromo-3,4-dihydro-1H-1,8-naphthyridin-2-one (0.61 g, 2.70 mmole), N-[1-(2-dimethylaminoethyl)-1H-indol-3-ylmethyl]-N-methyl-acrylamide (1.00 g, 3.50 mmole), Pd(OAc)$_2$ (0.08 g, 0.35 mmole), tri-ortho-tolylphosphine (0.21 g, 0.70 mmole), and diisopropylethylamine (0.91 mL, 5.25 mmole) in propionitrile (70 mL) was deoxygenated, then was and heated to reflux under a N$_2$ overnight. The dark mixture was filtered through a pad of celite®, and the filter pad was rinsed with acetonitrile (250 mL).

The filtrate was concentrated in vacuo, and the residue was purified by flash chromatography on silica gel (10% MeOH/CHCl$_3$ containing 5% NH$_4$OH in the MeOH). The title compound (0.20 g. 13%) was obtained as a light yellow solid after drying in vacuo: MS (ES) m/e 432 (M+H)$^+$.

Example 14

Preparation of (E)-N-methyl-3-(8-oxo-6,7,8,9-tetrahydro-5H-pyrido[2,3-b]azepin-3-yl)acrylamide A solution of 3-bromo-5,6,7,9-tetrahydro-pyrido[2,3-b]azepin-8-one (0.60 g, 2.50 mmole), N-(2-methyl-1H-indol-3-ylmethyl)-N-methylacrylamide (0.85 g, 3.75 mmole), Pd(OAc)$_2$ (0.06 g, 0.25 mmole), tri-ortho-tolylphosphine (0.15 g, 0.50 mmole) and diisopropylethylamine (0.87 mL, 5.00 mmole) in propionitrile (50 mL) was deoxygenated, then was and heated to reflux under a N$_2$ overnight. The dark mixture was filtered through a pad of celite®, and the filter pad was rinsed with acetonitrile (200 mL). The filtrate was concentrated in vacuo, and the residue was purified by flash chromatography on silica gel (10% MeOH/CHCl$_3$). The title compound (0.35 g. 35%) was obtained as a light tan solid after drying in vacuo: MS (ES) m/e 246 (M+H)$^+$.

Example 15

Preparation of (E)-N-methyl-N-(1-methyl-1H-indol-3-ylmethyl)-3-[6-(pyridin-2-ylamino)pyridin-3-yl]acrylamide a) N-(1-methyl-1H-indol-3-ylmethyl)-N-methylacrylamide
   To a stirred solution of 1-methyl-3-(methylaminomethyl)-1H-indole (1.0 g, 5.7 mmole) and Et$_3$N (0.8 mL, 5.7 mmole) in CH$_2$Cl$_2$ (50 mL) at 0° C. was added acryloyl chloride (0.47 mL, 5.8 mmole) in one portion. After stirring for 1 h the reaction was washed with cold H$_2$O and brine, then was dried (MgSO$_4$) and concentrated under vacuum. This material was used without further purification.
b) (E)-N-Methyl-N-(1-methyl-1H-indol-3-ylmethyl)-3-[6-(pyridin-2-ylamino)pyridin-3-yl]acrylamide
   To a solution of N-(1-methyl-1H-indol-3-ylmethyl)-N-methylacrylamide, from Example 1 (a), in propionitrile (50 mL) was added 5-bromo-2,2'-dipyridylamine (1.2 g, 4.8 mmole), DIEA (1.8 mL, 10.3 mmole), Pd(OAc)$_2$ (112 mg, 0.5 mmole), and P(o-tol)$_3$ (304 mg, 1 mmole). The reaction was purged with Ar then stirred at reflux for 16 h. After cooling to room temperature the reaction was concentrated to dryness under vacuum. Flash chromatography on silica gel (3% (5% NH$_4$OH/MeOH)/CHCl$_3$), trituration with 1:1 Et$_2$O/petroleum ether, filtration, and drying under vacuum gave the title compound (1.24 g, 65%) as an off-white solid: MS (ES) m/e 398.2 (M+H)$^+$.

Example 16

Preparation of (E)-N-methyl-N-(2-methylbenzo[b]thiophen-3-ylmethyl)-3-(7-oxo-5,6,7,8-tetrahydro-1,8-naphthyridin-3-yl)acrylamide a) N-(Benzo[b]thiophen-3-ylmethyl)-N-methylacrylamide
   According to the procedure of Example 15 (a), except substituting 2-methyl-3-(methylaminomethyl)benzo[b]thiophene (1.0 g, 5.2 mmole) for 1-methyl-3-(methylaminomethyl)-1H-indole, the title compound was prepared. This was used without further purification.

b) (E)-N-Methyl-N-(2-methylbenzo[b]thiophen-3-ylmethyl)-3-(7-oxo-5,6,7,8-tetrahydro-1,8-naphthyridin-3-yl)acrylamide According to the procedure of Example 15 (b), except substituting 6-bromo-3,4-dihydro-1H-1,8-naphthyridin-2-one (1.3 g, 5.7 mmole) for the 5-bromo-2,2'-dipyridylamine, the title compound (0.849 g, 42%) was prepared as a white solid: MS (ES) m/e 392.2 (M+H)$^+$.

Example 17

Preparation of (E)-N-methyl-N-(1-methyl-1H-indol-2-ylmethyl)-3-[6-[N-(methylaminocarbonylmethyl)amino]pyridin-3-yl]acrylamide a) N-(1-methyl-1H-indol-2-ylmethyl)-N-methylacrylamide According to the procedure of Example 15 (a), except substituting 1-methyl-2-(methylaminomethyl)-1H-indole (1.2 g, 6.9 mmole) for the 1-methyl-3-(methylaminomethyl)-1H-indole, the title compound was prepared. This was used without further purification.

b) (E)-N-Methyl-N-(1-methyl-1H-indol-2-ylmethyl)-3-[6-[N-(methylaminocarbonylmethyl)amino]pyridin-3-yl]acrylamide According to the procedure of Example 15 (b), except substituting 5-bromo-2-(methylaminocarbonylmethyl)aminopyridine (1.5 g, 6.2 mmole) for the 5-bromo-2,2'-dipyridylamine, the title compound (1.7 g, 72%) was prepared as a white solid: MS (ES) m/e 392.2 (M+H)$^+$.

Example 18

Preparation of (E)-3-(6-amino-5-(methoxycarbonyl)pyridin-3-yl)-N-(1-methyl-1H-indol-3-ylmethyl)-N-methylacrylamide a) N-(1-methyl-1H-indol-2-ylmethyl)-N-methylacrylamide According to the procedure of Example 15 (a), except substituting 1-methyl-2-(methylaminomethyl)-1H-indole (1.2 g, 6.9 mmole) for the 1-methyl-3-(methylaminomethyl)-1H-indole, the title compound was prepared. This was used without further purification.

b) (E)-3-(6-Amino-5-(methoxycarbonyl)pyridin-3-yl)-N-(1-methyl-1H-indol-3-ylmethyl)-N-methylacrylamide According to the procedure of Example 15 (b), except substituting methyl 2-amino-5-bromonicotinate (1.4 g, 6.1 mmole) for the 5-bromo-2,2'-dipyridylamine, the title compound (1.78 g, 77%) was prepared as a white solid: MS (ES) m/e 379.2 (M+H)$^+$.

Example 19

Preparation of (E)-3-[6-[N-(methoxycarbonylmethyl)amino]pyridin-3-yl]-N-methyl-N-(2-methyl-1H-indol-3-ylmethyl)acrylamide To a stirred solution of (E)-3-[6-[N-(methoxycarbonylmethyl)amino]pyridin-3-yl]acrylic acid hydrochloride salt (2.0 g, 7.3 mmole) in 1:1 DMF/CH$_2$Cl$_2$ (100 mL) was added 2-methyl-3-(methylaminomethyl)indole (1.3 g, 7.5 mmole), Et$_3$N (2.1 mL, 15 mmole), and HOBt.H$_2$O (1.0 g, 7.4 mmole), followed by EDC (1.4 g, 7.3 mmole). After stirring at room temperature for 18 h the reaction was concentrated to dryness. The residue was taken up in EtOAc, and the solution was washed with H$_2$O then brine, dried (Na$_2$SO$_4$), and concentrated under vacuum. The remaining residue was purified by flash chromatography on silica gel (4% MeOH/CHCl$_3$) to give the title compound (2.08 g, 73%) as an off-white solid: MS (ES) m/e 393.2 (M+H)$^+$.

Example 20

Preparation of (E)-3-[6-[N-(carboxymethyl)amino]pyridin-3-yl]-N-methyl-N-(2-methyl-1H-indol-3-ylmethyl)acrylamide To a stirred solution of (E)-3-[6-[N-(methoxycarbonylmethyl)amino]pyridin-3-yl]-N-methyl-N-(2-methyl-1H-indol-3-ylmethyl)acrylamide (0.5 g, 1.3 mmole) in dioxane (30 mL) was added 1 N NaOH (2 mL, 2 mmole). After stirring for 18 h the reaction was neutralized with 1 N HCl (2 mL, 2 mmole) and concentrated to near dryness. The resulting suspension was diluted with H$_2$O and filtered. The solid was washed with H$_2$O and dried under vacuum to give the title compound (505 mg, 100%) as a off-white solid: MS (ES) m/e 379.2 (M+H)$^+$.

Example 21

Preparation of (E)-N-methyl-N-(2-methyl-1H-indol-3-ylmethyl)-3-[6-[N-(methylaminocarbonylmethyl)amino]pyridin-3-yl]acrylamide To (E)-3-[6-[N-(methoxycarbonylmethyl)amino]pyridin-3-yl]-N-methyl-N-(2-methyl-1H-indol-3-ylmethyl)acrylamide (0.7 g, 1.8 mmole) was added a solution of 2.0 M methylamine in MeOH (50 mL). After stirring for 72 h the reaction was concentrated to dryness. The residue was triturated with Et$_2$O, filtered, and dried under vacuum to give the title compound (0.703 g, 100%) as an off-white solid: MS (ES) m/e 392.2 (M+H)$^+$.

Example 22

Preparation of (E)-3-(2-aminopyrimidin-5-yl)-N-methyl-N-(1-methyl-1H-pyrrolo[2,3-b]pyridin-3-ylmethyl)acrylamide A solution of 2-amino-5-bromopyrimidine (0.27 g, 1.55 mmole), N-methyl-N-(1-methyl-1H-pyrrolo[2,3-b]pyridin-3-ylmethyl)acrylamide (0.5 g, 2.33 mmole), Pd(OAc)$_2$ (0.037 g, 0.163 mmole), P(o-tolyl)$_3$ (0.085 g, 0.28 mmole), and (i-Pr)$_2$NEt (0.42 mL, 2.33 mmole) in propionitrile (20 mL) was degassed then heated to reflux. After 18 hr the mixture was cooled to RT and concentrated. Flash chromatography on silica gel (10% MeOH/CH$_2$Cl$_2$) gave the title compound (0.100 g, 18%): MS (ES) m/e 363 (M+H)$^+$.

Example 23

Preparation of (E)-N-methyl-N-(1-methyl-1H-pyrrolo[2,3-b]pyridin-3-ylmethyl)-3-(7-oxo-5,6,7,8-tetrahydro-1,8-naphthyridin-3-yl)acrylamide According to the procedure of Example 22, except substituting 6-bromo-3,4-dihydro-1H-1,8-naphthyridin-2-one (0.352 g, 1.55 mmole) for the 2-amino-5-bromopyrimidine, the title compound (0.14 g, 16%) was prepared as a white powder: MS (ES) m/e 376 (M+H)+.

Example 24

Preparation of (E)-N-(2,3-dihydro-1H-3a-azacyclopenta indene-8-ylmethyl)-N-methyl-3-(7-oxo-5,6,7,8-tetrahydro-1,8-naphthyridin-3-yl)acrylamide EDC (0.192 g, 1.0 mmole) was added to a solution of (E)-3-(7-oxo-5,6,7,8-tetrahydro-1,8-naphthyridin-3-yl) acrylic acid hydrochloride salt (0.254 g, 1.0 mmole), 2,3-dihydro-8-(methylaminomethyl)-1H-3a-azacyclopenta[a]indene (0.2 g, 1.0 mmole), HOBt.H$_2$O (0.135 g, 1.0 mmole), and Et$_3$N (0.15 mL, 1.1 mmole) in DMF (20 mL) at RT. The reaction was stirred overnight, then was poured into H$_2$O (50 mL) and extracted with CH$_2$Cl$_2$ (2×30 mL). The combined extracts were washed with brine and dried (MgSO$_4$). Flash chromatography on silica gel (5% MeOH/CH$_2$Cl$_2$) gave the title compound (0.1 g, 25%) a yellow solid: MS (ES) m/e 401 (M+H)+.

Example 25

Preparation of (E)-N-(1-ethyl-5-fluoro-1H-indol-3-ylmethyl)-N-methyl-3-(7-oxo-5,6,7,8-tetrahydro-1,8-naphthyridin-3-yl)acrylamide According to the procedure of Example 24, except substituting (1-ethyl-5-fluoro-3-(methylaminomethyl)-1H-indole (0.1 g, 0.49 mmole) for the 2,3-dihydro-8-(methylaminomethyl)-1H-3a-azacyclopenta[a]indene, the title compound (0.028 g, 15%) was prepared as a white powder: MS (ES) m/e 407 (M+H)+.

Example 26

Preparation of (E)-N-(5-fluoro-1-methyl-1H-indol-3-ylmethyl)-N-methyl-3-(7-oxo-5,6,7,8-tetrahydro-1,8-naphthyridin-3-yl)acrylamide According to the procedure of Example 24, except substituting 5-fluoro-1-methyl-3-(methylaminomethyl)-1H-indole (0.13 g, 0.67 mmole) for the 2,3-dihydro-8-(methylaminomethyl)-1H-3a-azacyclopenta[a]indene, the title compound (0.1 g, 37%) was prepared as a slightly yellow crystalline solid: MS (ES) m/e 393 (M+H)+.

Example 27

Preparation of (E)-N-(5-fluoro-1-methyl-1H-indol-3-ylmethyl)-N-methyl-3-(7-oxo-5,6,7,8-tetrahydro-1,8-naphthyridin-3-yl)acrylamide According to the procedure of Example 24, except substituting 6-fluoro-1-methyl-3-(methylaminomethyl)-1H-indole (0.12 g, 0.59 mmole) for the 2,3-dihydro-8-(methylaminomethyl)-1H-3a-azacyclopenta[a]indene, the title compound (0.1 g, 43%) was prepared as a white crystalline solid: MS (ES) m/e 393 (M+H)+.

Example 28

Preparation of (E)-N-(7-fluoro-1-methyl-1H-indol-3-ylmethyl)-N-methyl-3-(7-oxo-5,6,7,8-tetrahydro-1,8-naphthyridin-3-yl)acrylamide According to the procedure of Example 24, except substituting 7-fluoro-1-methyl-3-(methylaminomethyl)-1H-indole (0.18 g, 0.93 mmole) for the 2,3-dihydro-8-(methylaminomethyl)-1H-3a-azacyclopenta[a]indene, the title compound (0.1 g, 27%) was prepared as a white powder: MS (ES) m/e 393 (M+H)+.

Example 29

Preparation of (E)-3-(6-aminopyridin-3-yl)-N-(6-fluoro-1-methyl-1H-indol-3-ylmethyl)-N-methylacrylamide According to the procedure of Example 24, except substituting 6-fluoro-1-methyl-3-(methylaminomethyl)-1H-indole (0.11 g, 0.59 mmole) for the 2,3-dihydro-8-(methylaminomethyl)-1H-3a-azacyclopenta[a]indene, and substituting (E)-3-(6-amino-pyridin-3-yl)acrylic acid (0.098 g, 0.59 mmole) for the (E)-3-(7-oxo-5,6,7,8-tetrahydro-1,8-naphthyridin-3-yl)acrylic acid hydrochloride salt, the title compound (0.1 g, 27%) was prepared as a white powder: MS (ES) m/e 339 (M+H)+.

Example 30

Preparation of (E)-3-(6-aminopyridin-3-yl)-N-(4,6-dichloro-1-methyl-1H-indol-2-ylmethyl)-N-methylacrylamide EDC (84.4 mg, 0.44 mmole) was added all at once to a solution of (E)-3-(6-amino-pyridin-3-yl)acrylic acid (65.7 mg, 0.40 mmole), 4,6-dichloro-1-methyl-2-(methylaminomethyl)-1H-indole (107.0 mg, 0.44 mmole), HOBt.H$_2$O (59.5 mg, 0.44 mmole), and Et$_3$N (0.14 mL, 1.0 mmole) in anhydrous DMF (4 mL) at RT. After 17 hr, the reaction was concentrated to dryness and the residue was re-concentrated from CHCl$_3$/xylenes (2×). Flash chromatography on silica gel (7% MeOH in 1:1 EtOAc/CHCl$_3$) gave the R$_f$ 0.44 component (10% MeOH in 1:1 EtOAc/CHCl$_3$) as a foam. This was solidified by re-concentration from MeOH/EtOAc/CHCl$_3$ several times. This material was triturated with hot EtOAc/MeOH, and the mixture was cooled to 0° C. The title compound was collected by suction filtration. The filtrate was concentrated and the residue was triturated with EtOAc to afford additional title compound. The combined desired solids were dried in high vacuum at 50-60° C. to afford the title compound (108.9 mg, 70%) as a light yellow solid: $^1$H NMR (400 MHz, CDCl$_3$) 1.8:1 mixture of amide rotamers; δ 8.08-8.20 (2×s, 1 H), 7.70-7.90 (2×d, 1 H), 7.57-7.70 (2×s, 1 H), 7.46 (d, J=15.2 Hz, 1 H), 7.18 (s, 1 H), 6.97 (d, J=15.2 Hz, 1 H), 6.45 and 6.15 (2×m, 4 H), 5.02 and 4.82 (2×s, 2 H), 3.60-3.80 (2×s, 3 H), 2.99 and 3.11 (2×s, 3 H); MS (ES) m/e 239 and 391 (M+H)+.

Example 31

Preparation of (E)-3-(6-aminopyridin-3-yl)-N-(1,4-dimethyl-1H-indole-3-ylmethyl)-N-methylacrylamide To a stirred solution of 1,4-dimethyl-3-(methylaminomethyl)-1H-indole (188.2 mg, 1 mmole) and (E)-3-(6-aminopyridin-3-yl)acrylic acid (164 mg, 1 mmole) in dry DMF (12 mL) containing dry Et$_3$N (4 mL) was added HOBt.H$_2$O (153 mg, 1 mmole) and EDC (191.8 mg, 1 mmole). The reaction was stirred overnight under argon at ambient temperature, then was concentrated in vacuo. The residue was partitioned between EtOAc and 5% NaHCO$_3$ solution, and the layers were separated. The organic layer was washed with brine, dried (MgSO$_4$), filtered, and concentrated. Flash chromatography on silica gel afforded the title compound (120 mg, 36%) as a white solid: MS (ES) m/e 335.2 (M+H)$^+$.

Anal. Calcd for C$_{20}$H$_{22}$N$_4$O.0.25 H$_2$O: C, 70.88; H, 6.69; N, 16.53. Found: C, 71.11; H, 6.72; N, 16.36.

Example 32

Preparation of (E)-3-(6-aminopyridin-3-yl)-N-(4-methoxy-1-methyl-1H-indol-3-ylmethyl)-N-methylacrylamide According to the procedure of Example 31, except substituting 4-methoxy-1-methyl-3-(methylaminomethyl)-1H-indole for the 1,4-dimethyl-3-(methylaminomethyl)-indole, the title compound (100 mg, 29%) was obtained as a light yellow solid: MS (ES) m/e 351.2 (M+H)$^+$. Anal. Calcd for C$_{20}$H$_{22}$N$_4$O$_2$.0.25 H$_2$O: C, 67.68; H, 6.39; N, 15.79. Found: C, 67.31; H, 6.21; N, 15.97.

Example 33

Preparation of (E)-3-(6-aminopyridin-3-yl)-N-(5-methoxy-1-methyl-1H-indol-3-ylmethyl)-N-methylacrylamide According to the procedure of Example 31, except substituting 5-methoxy-1-methyl-3-(methylaminomethyl)-1H-indole for the 1,4-dimethyl-3-(methylaminomethyl)-1H-indole, the title compound (110 mg, 31%) was obtained as a light tan solid: MS (ES) m/e 351.2 (M+H)$^+$. Anal. Calcd for C$_{20}$H$_{22}$N$_4$O$_2$.0.75 H$_2$O: C, 66.01; H, 6.51; N, 15.39. Found: C, 65.83; H, 6.29; N, 15.60.

Example 34

Preparation of (E)-3-(6-aminopyridin-3-yl)-N-(7-chloro-1H-indol-3-ylmethyl)-N-methylacrylamide According to the procedure of Example 31, except substituting 7-chloro-1-methyl-3-(methylaminomethyl)-1H-indole for the dimethyl-3-(methylaminomethyl)-1H-indole, the title compound (180 mg, 52%) as obtained as a yellow solid: MS (ES) m/e 355.2 (M+H)$^+$.

Anal. Calcd for C$_{19}$H$_{19}$ClN$_4$O.0.25 H$_2$O: C, 63.51; H, 5.47; N, 15.59. Found: C, 63.55; H, 5.32; N, 15.68.

Example 35

Preparation of (E)-3-(6-aminopyridin-3-yl)-N-(7-methoxy-1-methyl-1H-indol-3-ylmethyl)-N-methylacrylamide According to the procedure of Example 31, except substituting 7-methoxy-1-methyl-3-(methylaminomethyl)-1H-indole for the 1,4-dimethyl-3-(methylaminomethyl)-1H-indole, the title compound (140 mg, 40%) was obtained as a tan solid: MS (ES) m/e 351.2 (M+H)$^+$. Anal. Calcd for C$_{20}$H$_{22}$N$_4$O$_2$.0.5 H$_2$O: C, 66.83; H, 6.45; N, 15.58. Found: C, 66.81; H, 6.41; N, 15.19.

Example 36

Preparation of (E)-3-(6-aminopyridin-3-yl)-N-(6-chloro-1H-indol-3-ylmethyl)-N-methylacrylamide According to the procedure of Example 31, except substituting 6-chloro-1-methyl-3-(methylaminomethyl)-1H-indole for the 1,4-dimethyl-3-(methylaminomethyl)-1H-indole, the title compound (176 mg, 50%) was obtained as a yellow solid: MS (ES) m/e 355.2 (M+H)$^+$. Anal. Calcd for C$_{19}$H$_{19}$ClN$_4$O.0.5 H$_2$O: C, 62.72; H, 5.54; N, 15.40. Found: C, 62.79; H, 5.20; N, 15.85.

Example 37

Preparation of (E)-3-(6-aminopyridin-3-yl)-N-(5-chloro-1H-indol-3-ylmethyl)-N-methylacrylamide According to the procedure of Example 31, except substituting 5-chloro-1-methyl-3-(methylaminomethyl)-1H-indole for the 1,4-dimethyl-3-(methylaminomethyl)-1H-indole the title compound was obtained as a tan solid (176 mg, 54%): MS (ES) m/e 355.2 (M+H)$^+$. Anal. Calcd for C$_{19}$H$_{19}$ClN$_4$O.0.25 H$_2$O: C, 63.51; H, 5.47; N, 15.59. Found: C, 63.63; H, 5.84; N, 15.83.

Example 38

Preparation of (E)-3-(6-aminopyridin-3-yl)-N-(4-chloro-1H-indol-3-ylmethyl)-N-methylacrylamide According to the procedure of Example 31, except substituting 4-Chloro-1-methyl-3-(methylaminomethyl)-1H-indole for the 1,4-dimethyl-3-(methylaminomethyl)-indole the title compound was obtained as a tan solid (150 mg, 42%): MS (ES) m/e 355.2 (M+H)$^+$.

Anal. Calcd for C$_{19}$H$_{19}$ClN$_4$O.0.25 H$_2$O: C, 63.51; H, 5.47; N, 15.59. Found: C, 63.33; H, 5.38; N, 15.34.

Example 39

Preparation of (E)-3-(6-aminopyridin-3-yl)-N-(3,3-dimethyl-3H-indene-1-ylmethyl)-N-methylacrylamide According to the procedure of Example 31, except substituting 1,1-dimethyl-3-(methylaminomethyl)-3H-indene for the 1,4-dimethyl-3-(methylaminomethyl)-1H-indole, the title compound (43 mg, 13%) was obtained as a white solid: MS (ES) m/e 334.2 (M+H)$^+$. Anal. Calcd for C$_{21}$H$_{23}$N$_3$O.0.75 H$_2$O: C, 72.70; H, 7.12; N, 12.11. Found: C, 72.38; H, 6.80; N, 11.69.

Example 40

Preparation of (E)-3-(6-aminopyridin-3-yl)-N-(7-hydroxy-1-methyl-1H-indol-3-ylmethyl)-N-methylacrylamide According to the procedure of Example 31, except substituting 7-hydroxy-1-methyl-3-(methylaminomethyl)-1H-indole for the 1,4-dimethyl-3-(methylaminomethyl)-1H-indole, the title compound was obtained as a tan solid (60 mg, 17.9%): MS (ES) m/e 337.2 (M+H)$^+$. Anal. Calcd for C$_{19}$H$_{20}$N$_4$O$_2$.1.0 H$_2$O: C, 64.39; H, 6.26; N, 15.81. Found: C, 63.99; H, 5.78; N, 15.54.

Example 41

Preparation of (E)-N-methyl-3-(7-oxo-5,6,7,8-tetrahydro-1,8-naphthyridin-3-yl)-N-(1,2,7-trimethyl-1H-indol-3-ylmethyl)-acrylamide a) N-Methyl-N-(1,2,7-trimethyl-1H-indol-3-ylmethyl)acrylamide To a cold solution (ice bath) of 3-(methylaminomethyl)-1,2,7-trimethyl-1H-indole (570 mg, 2.8 mmole) in dry CH$_2$Cl$_2$ (24 mL) was added dry Et$_3$N (0.25 mL, 2.9 mmole). The reaction was stirred in the cold under argon for 2 h then was poured into H$_2$O (40 mL). The layers were separated, and the organic layer was washed with brine, dried (MgSO$_4$), filtered, and concentrated. The title compound (0.7 g, 97%) was obtained as a light orange solid: MS (ES) m/e 257.2 (M+H)$^+$.

b) (E)-N-Methyl-3-(7-oxo-5,6,7,8-tetrahydro-1,8-naphthyridin-3-yl)-N-(1,2,7-trimethyl-1H-indol-3-ylmethyl)-acrylamide A mixture of N-methyl-N-(1,2,7-trimethyl-1H-indol-3-ylmethyl)acrylamide (256 mg, 1 mmole) and 6-bromo-3,4-dihydro-1H-1,8-naphthyridin-2-one (227 mg, 1 mmole) in propionitrile (20 mL) was treated with DIEA (0.3 mL), Pd(OAc)$_2$ (29 mg, 0.13 mmole), and tri-o-tolylphosphine (50 mg, 0.16 mmole). The reaction was heated at reflux under argon for 10 h, then was cooled to RT and filtered through supercel. The filtrate was concentrated and the residue was purified by flash chromatography on silica gel to afford the title compound (100 mg, 25%) as an off-white solid: MS (ES) m/e 403.2 (M+H)$^+$. Anal. Calcd for C$_{24}$H$_{26}$N$_4$O$_2$.2.75 H$_2$O: C, 63.77; H, 7.02; N, 12.39. Found: C, 63.81; H, 7.25; N, 11.90.

Example 42

Preparation of (E)-N-(7-chloro-1-methyl-1H-indol-3-ylmethyl)-N-methyl-3-(7-oxo-5,6,7,8-tetrahydro-1,8-naphthyridin-3-yl)-acrylamide A solution of 7-chloro-1-methyl-3-(methylaminomethyl)-1H-indole (104.3 mg, 0.5 mmole) and (E)-3-(7-oxo-5,6,7,8-tetrahydro-1,8-naphthyridin-3-yl)-acrylic acid (109.1 mg, 0.5 mmole) in dry DMF (8 mL) was treated with dry Et$_3$N (0.2 mL), HOBt.H$_2$O (76.5 mg, 0.5 mmole) and EDC (96 mg, 0.5 mmole). The solution was stirred at RT under argon for 20 h, then was concentrated. The oily residue was dissolved in MeOH and the solution was cooled. The precipitated solid was collected, washed with cold MeOH, and dried to give the title compound (95 mg, 47%): MS (ES) m/e 409.2 (M+H)$^+$. Anal. Calcd for C$_{22}$H$_{21}$ClN$_4$O$_2$.0.25 H$_2$O: C, 63.92; H, 5.24; N, 13.55. Found: C, 63.56; H, 5.14; N, 13.73.

Example 43

Preparation of (E)-N-(7-chloro-1H-indol-3-ylmethyl)-N-methyl-3-(7-oxo-5,6,7,8-tetrahydro-1,8-naphthyridin-3-yl)-acrylamide According to the procedure of Example 42, except substituting 7-chloro-3-(methylaminomethyl)-1H-indole for the 7-chloro-1-methyl-3-(methylaminomethyl)-1H-indole, the title compound (25 mg, 13%) was obtained as an off white solid after chromatography on silica gel: MS (ES) m/e 395.0 (M+H)$^+$ Example 44

Preparation of (E)-2,N-dimethyl-N-(2-methyl-1H-indol-3-ylmethyl)-3-(7-oxo-5,6,7,8-tetrahydro-1,8-naphthyridin-3-yl)acrylamide According to the procedure of Example 4, except substituting (E)-2-methyl-3-(7-oxo-5,6,7,8-tetrahydro-1,8-naphthyridin-3-yl)acrylic acid hydrochloride salt (0.50 g, 1.8 mmole) for the (E)-3-(2-oxo-2,3-dihydro-1H-indol-5-yl) acrylic acid hydrochloride salt, the title compound (0.64 g, 89%) was prepared as a light yellow solid: MS (ES) m/e 389 (M+H)$^+$.

Example 45

Preparation of (E)-3,N-dimethyl-N-(2-methyl-1H-indol-3-ylmethyl)-3-(7-oxo-5,6,7,8-tetrahydro-1,8-naphthyridin-3-yl)acrylamide According to the procedure of Example 4, except substituting (E)-3-methyl-3-(7-oxo-5,6,7,8-tetrahydro-1,8-naphthyridin-3-yl)acrylic acid hydrochloride salt (0.50 g, 1.8 mmole) for the (E)-3-(2-oxo-2,3-dihydro-1H-indol-5-yl) acrylic acid hydrochloride salt, the title compound (0.67 g, 92%) was prepared as a light yellow solid: MS (ES) m/e 389 (M+H)$^+$.

Example 46

Preparation of (E)-N-methyl-N-(2-methyl-1H-indol-3-ylmethyl)-3-(4-methyl-3-oxo-2,3,4,5-tetrahydro-1H-pyrido[2,3-e]-1,4-diazepin-7-yl)acrylamide According to the procedure of Example 1, except substituting 7-bromo-4-methyl-1,2,4,5-tetrahydropyrido[2,3-e]-1,4-diazepin-3-one (0.50 g, 1.9 mmole) for the 2-amino-5-bromopyrimidine, the title compound (0.30 g, 62%) was prepared as a light yellow solid: MS (ES) m/e 404 (M+H)$^+$.

Example 47

Preparation of (E)-N-methyl-N-(2-methyl-1H-indol-3-ylmethyl)-3-(8-oxo-6,7,8,9-tetrahydro-5H-pyrido[2,3-b]azepin-3-yl)acrylamide EDC (0.18 g, 0.96 mmole) was added to a solution of (E)-3-(8-oxo-6,7,8,9-tetrahydro-5H-pyrido[2,3-b]azepin-3-yl)acrylic acid hydrochloride salt (0.24 g, 0.87 mmole), 2-methyl-3-(methylaminomethyl)indole (0.15 g, 0.87 mmole), HOBt.H$_2$O (0.13 g., 0.96 mmole) and diisopropylethylamine (0.45 mL, 2.61 mmole) in DMF (15 mL) at RT. The reaction was stirred overnight then was concentrated in vacuo. The residue was diluted with water and extracted with ethyl acetate. The combined organic extracts were washed with brine and dried over Na$_2$SO$_4$. Preparative HPLC on a Waters C-18 ODSA column (gradient: 20-100% H$_2$O/CH$_3$CN) gave the title compound (0.13 g, 38%) as a light yellow solid after drying in vacuo: MS (ES) m/e 389 (M+H)$^+$.

Example 48

Preparation of (E)-N-[1-(2-hydroxyethyl)-1H-indol-3-ylmethyl]-N-methyl-3-(7-oxo-5,6,7,8-tetrahydro-1,8-naphthyridin-3-yl)acrylamide EDC (0.54 g, 2.80 mmole) was added to a solution of (E)-3-(7-oxo-5,6,7,8-tetrahydro-1,8-naphthyridin-3-yl) acrylic acid hydrochloride salt (0.71 g, 2.80 mmole), 1-(2-hydroxyethyl)-3-(methylaminomethyl)-1H-indole (0.52 g, 2.55 mmole), HOBt.H$_2$O (0.38 g., 2.80 mmole) and diisopropylethylamine (1.11 mL, 6.40 mmole) in DMF (25 mL) at RT. The reaction was stirred overnight then was concentrated in vacuo. The residue was diluted with water and extracted with ethyl acetate. The combined organic extracts were washed with brine and dried over Na$_2$SO$_4$. Flash chromatography on silica gel (20% EtOH/EtOAc) gave title compound (0.28 g, 27%) as an off-white solid after drying in vacuo: MS (ES) m/e 405 (M+H)+.

Example 49

Preparation of (E)-N-methyl-N-(1-methyl-1H-indol-3-ylmethyl)-3-(8-oxo-6,7,8,9-tetrahydro-5H-pyrido[2,3-b]azepin-3-yl)acrylamide EDC (0.06 g, 0.30 mmole) was added to a solution of (E)-3-(8-oxo-6,7,8,9-tetrahydro-5H-pyrido[2,3-b]azepin-3-yl)acrylic acid hydrochloride salt (0.07 g, 0.27 mmole), 1-methyl-3-(methylaminomethyl)-1H-indole (0.05 g, 0.27 mmole), HOBt.H$_2$O (0.04 g., 0.30 mmole) and diisopropylethylamine (0.14 mL, 0.81 mmole) in DMF (15 mL) at RT. The reaction was stirred overnight then was concentrated in vacuo. The residue was diluted with water and extracted with ethyl acetate. The combined organic extracts were washed with brine and dried over Na$_2$SO$_4$. Flash chromatography on silica gel (20% EtOH/EtOAc) gave title compound (0.05 g, 48%) as an off-white solid after drying in vacuo: MS (ES) m/e 389 (M+H)+.

Example 50

Preparation of (E)-N-[1-(2-hydroxyethyl)-1H-indol-3-ylmethyl]-N-methyl-3-(7-oxo-5,6,7,8-tetrahydro-1,8-naphthyridin-3-yl)acrylamide EDC (0.35 g, 1.81 mmole) was added to a solution of (E)-3-(7-oxo-5,6,7,8-tetrahydro-1,8-naphthyridin-3-yl) acrylic acid hydrochloride salt (0.42 g, 1.65 mmole), 1-ethyl-3-(methylaminomethyl)-1H-indole (0.31 g, 1.65 mmole), HOBt.H$_2$O (0.24 g., 1.81 mmole) and diisopropylethylamine (0.86 mL, 4.95 mmole) in DMF (15 mL) at RT. The reaction was stirred overnight then was concentrated in vacuo. The residue was diluted with water and extracted with ethyl acetate. The combined organic extracts were washed with brine and dried over Na$_2$SO$_4$. Flash chromatography on silica gel (10% EtOH/EtOAc) gave title compound (0.39 g, 61%) as a light yellow solid after drying in vacuo: MS (ES) m/e 389 (M+H)+.

Example 51

Preparation of (E)-N-(7-chloro-1-methyl-1H-indol-3-ylmethyl)-3-[6-[N-(methoxycarbonylmethyl)amino]pyridin-3-yl]-N-methylacrylamide According to the procedure of Example 19, except substituting 7-chloro-1-methyl-3-(methylaminomethyl)-1H-indole (1.4 g, 6.7 mmole) for the 2-methyl-3-(methylaminomethyl)indole, the title compound (2.38 g, 84%) was prepared as a pale yellow solid: MS (ES) m/e 427.0 (M+H)+.

Example 52

Preparation of (E)-3-[6-[N-(carboxymethyl)amino]pyridin-3-yl]-N-(7-chloro-1-methyl-1H-indol-3-ylmethyl)-N-methylacrylamide According to the procedure of Example 20, except substituting (E)-N-(7-chloro-1-methyl-1H-indol-3-ylmethyl)-3-[6-[N-(methoxycarbonylmethyl)amino]pyridin-3-yl]-N-methylacrylamide (0.75 g, 1.8 mmole) for the (E)-3-[6-[N-(methoxycarbonylmethyl)amino]pyridin-3-yl]-N-methyl-N-(2-methyl-1H-indol-3-ylmethyl)acrylamide, the title compound (0.746 g, 100%) was prepared as a white solid: MS (ES) m/e 413.2 (M+H)+.

Example 53

Preparation of (E)-N-(7-chloro-1-methyl-1H-indol-3-ylmethyl)-N-methyl-3-[6-[N-(methylaminocarbonylmethyl)amino]pyridin-3-yl]acrylamide According to the procedure of Example 21, except substituting (E)-N-(7-chloro-1-methyl-1H-indol-3-ylmethyl)-3-[6-[N-(methoxycarbonylmethyl)amino]pyridin-3-yl]-N-methylacrylamide (0.75 g, 1.8 mmole) for the (E)-3-[6-[N-(methoxycarbonylmethyl)amino]pyridin-3-yl]-N-methyl-N-(2-methyl-1H-indol-3-ylmethyl)acrylamide, the title compound (0.721 g, 94%) was prepared as a white solid: MS (ES) m/e 426.0 (M+H)+.

Example 54

Preparation of (E)-3-(6-aminopyridin-3-yl)-N-(2-chloro-1-methyl-1H-indol-3-ylmethyl)-N-methylacrylamide According to the procedure of Example 31, except substituting 2-chloro-1-methyl-2-(methylaminomethyl)-1H-indole (0.7 g, 3.0 mmole) for the 1,4-dimethyl-3-(methylaminomethyl)-1H-indole, the title compound (0.935 g, 88%) was obtained as an off-white solid: MS (ES) m/e 355.2 (M+H)+.

Example 55

Preparation of (E)-N-(2-chloro-1-methyl-1H-indol-3-ylmethyl)-N-methyl-3-(7-oxo-5,6,7,8-tetrahydro-1,8-naphthyridin-3-yl)acrylamide According to the procedure of Example 24, except substituting 2-chloro-1-methyl-2-(methylaminomethyl)-1H-indole (0.7 g, 3.0 mmole) for the 2,3-dihydro-8-(methylaminomethyl)-1H-3a-azacyclopenta[a]indene, the title compound (1.03 g, 84%) was obtained as a white solid: MS (ES) m/e 409.0 (M+H)+.

Example 56

Preparation of (E)-N-(naphthalen-2-ylmethyl)-N-methyl-3-(7-oxo-5,6,7,8-tetrahydro-1,8-naphthyridin-3-yl)acrylamide According to the procedure of Example 24, except substituting 2-(methylaminomethyl)naphthalene (0.55 g, 3.2 mmole) for the 2,3-dihydro-8-(methylaminomethyl)-1H-3a-azacyclopenta[a]indene, the title compound (0.871 g, 73%) was obtained as a white solid: MS (ES) m/e 372.2 (M+H)+.

Example 57

Preparation of (E)-N-(1-methyl-1H-indol-3-ylmethyl)-N-methyl-3-(6-amino-7-oxo-5,6,7,8-tetrahydro-1,8-naphthyridin-3-yl)acrylamide a) (E)-N-(1-Methyl-1H-indol-3-ylmethyl)-N-methyl-3-[6-(benzhydrylideneamino)-7-oxo-5,6,7,8-tetrahydro-1,8-naphthyridin-3-yl]acrylamide According to the procedure of Example 15, except substituting 3-(benzhydrylideneamino)-6-bromo-3,4-dihydro-1H-

1,8-naphthyridin-2-one (3.5 g, 8.6 mmole) for the 5-bromo-2,2'-dipyridylamine, the title compound (3.72 g, 78%) was obtained as a pale yellow solid: MS (ES) m/e 554.4 (M+H)$^+$.

b) (E)-N-(1-Methyl-1H-indol-3-ylmethyl)-N-methyl-3-(6-amino-7-oxo-5,6,7,8-tetrahydro-1,8-naphthyridin-3-yl)acrylamide To a suspension of (E)-N-(1-methyl-1H-indol-3-ylmethyl)-N-methyl-3-[6-(benzhydrylideneamino)-7-oxo-5,6,7,8-tetrahydro-1,8-naphthyridin-3-yl]acrylamide (0.5 g, 0.9 mmole) in dioxane (15 mL) was added 1 N HCl (10 mL) with stirring at RT. After approximately 5 min the suspension cleared up then gradually reformed. After stirring for 1 h the reaction was neutralized with 1 N NaOH (10 mL) and concentrated to near dryness under vacuum. The resulting suspension was diluted with H$_2$O (20 mL) and filtered, and the solid was rinsed with cold H$_2$O and dried under vacuum. The slightly pinkish solid was triturated with Et$_2$O, filtered, and dried under vacuum to give the title compound (248 mg, 71%) as an off-white solid: MS (ES) m/e 390.4 (M+H)$^+$.

Example 58

Preparation of (E)-N-(benzofuran-2-ylmethyl)-N-methyl-3-(7-oxo-5,6,7,8-tetrahydro-1,8-naphthyridin-3-yl)acrylamide According to the procedure of Example 4, except substituting (E)-3-(7-oxo-5,6,7,8-tetrahydro-1,8-naphthyridin-3-yl)acrylic acid hydrochloride salt (1.60 g, 6.3 mmole) for the (E)-3-(2-oxo-2,3-dihydro-1H-indol-5-yl)acrylic acid hydrochloride salt, and substituting 2-(methylaminomethyl)benzofuran (1.20 g, 6.9 mmole) for the 2-methyl-3-(methylaminomethyl)indole, the title compound (2.0 g, 90%) was prepared as a tan solid: MS (ES) m/e 363 (M+H)$^+$.

Example 59

Preparation of (E)-3-(6-aminopyridin-3-yl)-N-(7-methoxycarbonyl-1-methyl-1H-indol-3-ylmethyl)-N-methylacrylamide According to the procedure of Example 31, except substituting methyl 1-methyl-3-(methylaminomethyl)-1H-indole-7-carboxylate for the 1,4-dimethyl-3-(methylaminomethyl)-1H-indole, the title compound (150 mg, 34%) was obtained, after trituration with diethyl ether, as an off-white solid: MS (ES) m/e 379.2 (M+H)$^+$. Anal. Calcd for C$_{21}$H$_{22}$N$_4$O$_3$.0.25 H$_2$O: C, 65.87; H, 5.92; N, 14.63. Found: C, 66.02; H, 5.71; N, 14.29.

Example 60

Preparation of (E)-3-(aminopyridin-3-yl)-N-methyl-N-(1,2,7-trimethyl-1H-indol-3-ylmethyl)acrylamide According to the procedure of Example 31, except substituting 3-(methylaminomethyl)-1,2,7-trimethyl-1H-indole for the 1,4-dimethyl-3-(methylaminomethyl)-1H-indole, the title compound (120 mg, 29%) was obtained, after trituration with ethyl acetate, as a light yellow solid: MS (ES) m/e 349.0 (M+H)$^+$. Anal. Calcd for C$_{21}$H$_{24}$N$_4$O.H$_2$O: C, 68.82; H, 7.69; N, 15.29. Found: C, 68.42; H, 6.86; N, 15.61.

Example 61

Preparation of (E)-3-(6-aminopyridin-3-yl)-N-(7-chloro-1H-indol-3-ylmethyl)-N-methylacrylamide According to the procedure of Example 31, except substituting 7-chloro-3-(methylaminomethyl)-1H-indole for the 1,4-dimethyl-3-(methylaminomethyl)-1H-indole, the title compound (150 mg, 25%) was obtained, after trituration with ethyl acetate, as a light yellow solid: MS (ES) m/e 341.0 (M+H)$^+$. Anal. Calcd for C$_{18}$H$_{17}$N$_4$O.0.25 H$_2$O: C, 62.60; H, 5.10; N, 16.22. Found: C, 62.29; H, 5.01; N, 16.32.

Example 62

Preparation of (E)-N-(5-chloro-1-methyl-1H-indol-3-ylmethyl-N-methyl-3-(7-oxo-5,6,7,8-tetrahydro-1,8-naphthyridin-3-yl)acrylamide According to the procedure of Example 42, except substituting 5-chloro-1-methyl-3-(methylaminomethyl)-1H-indole for the 7-chloro-1-methyl-3-(methylaminomethyl)-1H-indole, the title compound (100 mg, 49%) was obtained as a light tan solid: MS (ES) m/e 409.0 (M+H)$^+$. Anal. Calcd for C$_{22}$H$_{21}$ClN$_4$O$_2$.0.5 H$_2$O: C, 63.23; H, 5.32; N, 13.40. Found: C, 63.19; H, 5.23; N, 13.45.

Example 63

Preparation of (E)-N-(6-chloro-1-methyl-1H-indol-3-ylmethyl)-N-methyl-3-(7-oxo-5,6,7,8-tetrahydro-1,8-naphthyridin-3-yl)acrylamide According to the procedure of Example 42, except substituting 6-chloro-1-methyl-3-(methylaminomethyl)-1H-indole for the 7-chloro-1-methyl-3-(methylaminomethyl)-1H-indole, the title compound (125 mg, 61%) was obtained as a light tan solid: MS (ES) m/e 409.0 (M+H)$^+$. Anal. Calcd for C$_{22}$H$_{21}$ClN$_4$O$_2$.0.25 H$_2$O: C, 63.92; H, 5.24; N, 13.55. Found: C, 63.96; H, 4.98; N, 13.66.

Example 64

Preparation of (E)-N-(1,7-dimethyl-1H-indol-3-ylmethyl)-N-methyl-3-(7-oxo-5,6,7,8-tetrahydro-1,8-naphthyridin-3-yl)acrylamide According to the procedure of Example 42, except substituting 1,7-dimethyl-3-(methylaminomethyl)-1H-indole for the 7-chloro-1-methyl-3-(methylaminomethyl)-1H-indole, the title compound (100 mg, 51%) was obtained as a white solid: MS (ES) m/e 389.2 (M+H)$^+$. Anal. Calcd for C$_{23}$H$_{24}$N$_4$O$_2$.0.25 H$_2$O: C, 70.29; H, 6.28; N, 14.25. Found: C, 70.06; H, 6.23; N, 14.29

Example 65

Preparation of (E)-N-(1,6-dimethyl-1H-indol-3-ylmethyl)-N-methyl-3-(7-oxo-5,6,7,8-tetrahydro-1,8-naphthyridin-3-yl)acrylamide According to the procedure of Example 42, except substituting 1,6-dimethyl-3-(methylaminomethyl)-1H-indole for the 7-chloro-1-methyl-3-(methylaminomethyl)-1H-indole, the title compound (95 mg, 49%) was obtained as a white solid: MS (ES) m/e 389.2 (M+H)$^+$. Anal. Calcd for C$_{23}$H$_{24}$N$_4$O$_2$.0.75 H$_2$O: C, 68.72; H, 6.39; N, 13.93. Found: C, 68.98; H, 6.07; N, 13.81.

Example 66

Preparation of (E)-N-(1,4-dimethyl-1H-indol-3-ylmethyl)-N-methyl-3-(7-oxo-5,6,7,8-tetrahydro-1,8-naphthyridin-3-yl)acrylamide According to the procedure of Example 42, except substituting 1,4-dimethyl-3-(methylaminomethyl)-1H-indole for the 7-chloro-1-methyl-3-(methylaminomethyl)-1H-indole, the title compound (90 mg, 46%) was obtained as a white solid: MS (ES) m/e 389.0 $(M+H)^+$. Anal. Calcd for $C_{23}H_{24}N_4O_2.0.5\ H_2O$: C, 69.50; H, 6.33; N, 14.10. Found: C, 69.40; H, 6.24; N, 14.20.

Example 67

Preparation of (E)-N-(1,5-dimethyl-1H-indol-3-ylmethyl)-N-methyl-3-(7-oxo-5,6,7,8-tetrahydro-1,8-naphthyridin-3-yl)acrylamide According to the procedure of Example 42, except substituting 1,5-dimethyl-3-(methylaminomethyl)-1H-indole for the 7-chloro-1-methyl-3-(methylaminomethyl)-1H-indole, the title compound (100 mg, 51%) was obtained as a white solid: MS (ES) m/e 389.2 $(M+H)^+$. Anal. Calcd for $C_{23}H_{24}N_4O_2.0.125\ H_2O$: C, 70.70; H, 6.25; N, 14.34. Found: C, 70.75; H, 6.15; N, 14.38.

Example 68

Preparation of (E)-N-(7-methoxy-1-methyl-1H-indol-3-ylmethyl)-N-methyl-3-(7-oxo-5,6,7,8-tetrahydro-1,8-naphthyridin-3-yl)acrylamide According to the procedure of Example 42, except substituting 7-methoxy-1-methyl-3-(methylaminomethyl)-1H-indole for the 7-chloro-1-methyl-3-(methylaminomethyl)-1H-indole, the title compound (85 mg, 42%) was obtained as an off-white solid: MS (ES) m/e 405.2 $(M+H)^+$. Anal. Calcd for $C_{23}H_{24}N_4O_3$: C, 68.30; H, 5.95; N, 13.85. Found: C, 67.95; H, 5.94; N, 13.94.

Example 69

Preparation of (E)-N-(7-hydroxy-1-methyl-1H-indol-3-ylmethyl)-N-methyl-3-(7-oxo-5,6,7,8-tetrahydro-1,8-naphthyridin-3-yl)acrylamide According to the procedure of Example 42, except substituting 7-hydroxy-1-methyl-3-(methylaminomethyl)-1H-indole for the 7-chloro-1-methyl-3-(methylaminomethyl)-1H-indole, the title compound (200 mg, 51%) was obtained as a tan solid: MS (ES) m/e 391.2 $(M+H)^+$. Anal. Calcd for $C_{22}H_{22}N_4O_3.0.75\ H_2O$: C, 65.41; H, 5.85; N, 13.86. Found: C, 65.25; H, 5.95; N, 13.79.

Example 70

Preparation of (E)-N-(4-chloro-1-methyl-1H-indol-3-ylmethyl)-N-methyl-3-(7-oxo-5,6,7,8-tetrahydro-1,8-naphthyridin-3-yl)acrylamide According to the procedure of Example 42, except substituting 4-chloro-1-methyl-3-(methylaminomethyl for the 7-chloro-1-methyl-3-(methylaminomethyl)-1H-indole, the title compound (100 mg, 49%) was obtained as a white solid: MS (ES) m/e 409.0 $(M+H)^+$. Anal. Calcd for $C_{22}H_{21}ClN_4O_2$: 0.75 $H_2O$: C, 62.55; H, 5.36; N, 13.26. Found: C, 62.71; H, 5.24; N, 13.15.

Example 71

Preparation of (E)-N-(4-methoxy-1-methyl-1H-indol-3-ylmethyl)-N-methyl-3-(7-oxo-5,6,7,8-tetrahydro-1,8-naphthyridin-3-yl)acrylamide According to the procedure of Example 42, except substituting 4-methoxy-1-methyl-3-(methylaminomethyl)-1H-indole for the 7-chloro-1-methyl-3-(methylaminomethyl)-1H-indole, the title compound (65 mg, 32%) was obtained as an off-white solid: MS (ES) m/e 405.2 $(M+H)^+$. Anal. Calcd for $C_{23}H_{24}N_4O_3.1.25\ H_2O$: C, 64.69; H, 6.19; N, 13.33. Found: C, 64.49; H, 5.94; N, 13.76

Example 72

Preparation of (E)-N-(5-methoxy-1-methyl-1H-indol-3-ylmethyl)-N-methyl-3-(7-oxo-5,6,7,8-tetrahydro-1,8-naphthyridin-3-yl)acrylamide According to the procedure of Example 42, except substituting 5-methoxy-1-methyl-3-(methylaminomethyl)-1H-indole for the 7-chloro-1-methyl-3-(methylaminomethyl)-1H-indole, the title compound (90 mg, 44%) was obtained as an off-white solid: MS (ES) m/e 405.2 $(M+H)^+$. Anal. Calcd for $C_{23}H_{24}N_4O_3.0.5\ H_2O$: C, 66.81; H, 6.09; N, 13.55. Found: C, 66.67; H, 5.96; N, 13.87.

Example 73

Preparation of (E) 3-(6-aminopyridin-3-yl)-N-(7-carboxy-1-methyl-1H-indol-3-ylmethyl)-N-methylacrylamide A solution of (E)-3-(6-aminopyridin-3-yl)-N-(7-methoxycarbonyl-1-methyl-1H-indol-3-ylmethyl)-N-methylacrylamide (76 mg, 0.2 mmole) in methanol (4 mL), water (2 mL), and tetrahydrofuran (2 mL) was treated with LiOH (39 mg, 1.6 mmole), and the reaction was stirred at ambient temperature for 48 h. The mixture was filtered, and the filtrate was acidified to pH 4.0-4.5 with 1.0 N HCl. The precipitate was collected, washed with water and dried giving the title compound (25 mg, 35%) as a white solid: MS (ES) m/e 365.2 $(M+H)^+$. Anal. Calcd for $C_{20}H_{20}N_4O_3.0.25\ H_2O$: C, 65.11: H, 5.60; N, 15.18. Found: C, 64.83; H, 5.52; N, 15.07.

Example 74

Preparation of (E)-N-(6-methoxy-1-methyl-1H-indol-3-ylmethyl)-N-methyl-3-(7-oxo-5,6,7,8-tetrahydro-1,8-naphthyridin-3-yl)acrylamide According to the procedure of Example 42, except substituting 6-methoxy-1-methyl-3-(methylaminomethyl)-1H-indole for the 7-chloro-1-methyl-3-(methylaminomethyl)-1H-indole, the title compound (65 mg, 32%) was obtained as a yellow solid: MS (ES) m/e 405.2 $(M+H)^+$. Anal. Calcd for $C_{23}H_{24}N_4O_3\ H_2O$: C, 65.38; H, 6.20; N, 13.26. Found: C, 65.36; H, 5.98; N, 13.16.

Example 75

Preparation of (E)-3-(6-aminopyridin-3-yl)-N-(6-methoxycarbonyl-1-methyl-1H-indol-3-ylmethyl)-N-methylacrylamide According to the procedure of Example 31, except substituting methyl 1-methyl-3-(methylaminomethyl)-1H-indole-6-carboxylate for the 1,4-dimethyl-3-(methylaminomethyl)-1H-indole, the title compound (168 mg, 39%) was obtained, after silica gel chromatography, as a white solid: MS (ES) m/e 379.2 $(M+H)^+$. Anal. Calcd for $C_{21}H_{22}N_4O_3.0.125\ H_2O$: C, 66.25; H, 5.93; N, 14.71. Found: C, 66.60; H, 6.13; N, 14.18.

Example 76

Preparation of (E)-N-(3,3-dimethyl-3H-indene-1-ylmethyl)-N-methyl-3-(7-oxo-5,6,7,8-tetrahydro-1,8-naphthyridin-3-yl)acrylamide According to the procedure of Example 42, except substituting 3,3-dimethyl-1-(methylaminomethyl)-3H-indene for the 7-chloro-1-methyl-3-(methylaminomethyl)-1H-indole, the title compound (48 mg, 12%) was obtained, after silica gel chromatography, as a tan solid: MS (ES) m/e 388.2 (M+H)$^+$. Anal. Calcd for $C_{23}H_{24}N_4O_3 \cdot 0.375\ H_2O$: C, 73.31; H, 6.51; N, 10.66. Found: C, 72.91; H, 6.37; N, 11.16.

Example 77

Preparation of (E)-3-(6-aminopyridin-3-yl)-N-(4-fluoro-1-methyl-1H-indol-3-ylmethyl)-N-methylacrylamide According to the procedure of Example 24, except substituting 4-fluoro-1-methyl-3-(methylaminomethyl)-1H-indole (0.2 g, 1.04 mmole) for the 2,3-dihydro-8-(methylaminomethyl)-1H-3a-azacyclopenta[a]indene, and substituting (E)-3-(6-amino-pyridin-3-yl)acrylic acid (0.17 g, 1.04 mmole) for the (E)-3-(7-oxo-5,6,7,8-tetrahydro-1,8-naphthyridin-3-yl)acrylic acid hydrochloride salt, the title compound (0.11 g, 37%) was prepared as an off-white powder: MS (ES) m/e 339 (M+H)$^+$.

Example 78

Preparation of (E)-3-(6-aminopyridin-3-yl)-N-(5-fluoro-1-methyl-1H-indol-3-ylmethyl)-N-methylacrylamide According to the procedure of Example 24, except substituting 5-fluoro-1-methyl-3-(methylaminomethyl)-1H-indole (0.2 g, 1.04 mmole) for the 2,3-dihydro-8-(methylaminomethyl)-1H-3a-azacyclopenta[a]indene, and substituting (E)-3-(6-amino-pyridin-3-yl)acrylic acid (0.17 g, 1.04 mmole) for the (E)-3-(7-oxo-5,6,7,8-tetrahydro-1,8-naphthyridin-3-yl)acrylic acid hydrochloride salt, the title compound (0.14 g, 41%) was prepared as an off-white powder: MS (ES) m/e 339 (M+H)$^+$.

Example 79

Preparation of (E)-3-(6-aminopyridin-3-yl)-N-(7-fluoro-1-methyl-1H-indol-3-ylmethyl)-N-methylacrylamide According to the procedure of Example 24, except substituting 7-fluoro-1-methyl-3-(methylaminomethyl)-1H-indole (0.2 g, 1.04 mmole) for the 2,3-dihydro-8-(methylaminomethyl)-1H-3a-azacyclopenta[a]indene, and substituting (E)-3-(6-amino-pyridin-3-yl)acrylic acid (0.17 g, 1.04 mmole) for the (E)-3-(7-oxo-5,6,7,8-tetrahydro-1,8-naphthyridin-3-yl)acrylic acid hydrochloride salt, the title compound (0.1 g, 27%) was prepared as an off-white powder: MS (ES) m/e 339 (M+H)$^+$.

Example 80

Preparation of (E)-3-(6-aminopyridin-3-yl)-N-(4-fluoro-1H-indol-3-ylmethyl)-N-methylacrylamide According to the procedure of Example 24, except substituting 4-fluoro-3-(methylaminomethyl)-1H-indole (0.31 g, 1.74 mmole) for the 2,3-dihydro-8-(methylaminomethyl)-1H-3a-azacyclopenta[a]indene, and substituting (E)-3-(6-amino-pyridin-3-yl)acrylic acid (0.285 g, 1.74 mmole) for the (E)-3-(7-oxo-5,6,7,8-tetrahydro-1,8-naphthyridin-3-yl) acrylic acid hydrochloride salt, the title compound (0.2 g, 36%) was prepared as a white powder: MS (ES) m/e 325 (M+H)$^+$.

Example 81

Preparation of (E)-3-(6-aminopyridin-3-yl)-N-(7-fluoro-1H-indol-3-ylmethyl)-N-methylacrylamide According to the procedure of Example 24, except substituting 7-fluoro-3-(methylaminomethyl)-1H-indole (0.31 g, 1.74 mmole) for the 2,3-dihydro-8-(methylaminomethyl)-1H-3a-azacyclopenta[a]indene, and substituting (E)-3-(6-amino-pyridin-3-yl)acrylic acid (0.285 g, 1.74 mmole) for the (E)-3-(7-oxo-5,6,7,8-tetrahydro-1,8-naphthyridin-3-yl) acrylic acid hydrochloride salt, the title compound (0.1 g, 18%) was prepared as a white powder: MS (ES) m/e 325 (M+H)$^+$.

Example 82

Preparation of (E)-N-(4-fluoro-1-methyl-1H-indol-3-ylmethyl)-N-methyl-3-(7-oxo-5,6,7,8-tetrahydro-1,8-naphthyridin-3-yl)acrylamide According to the procedure of Example 24, except substituting 4-fluoro-1-methyl-3-(methylaminomethyl)-1H-indole (0.13 g, 0.68 mmole) for the 2,3-dihydro-8-(methylaminomethyl)-1H-3a-azacyclopenta[a]indene), the title compound (0.15 g, 56%) was prepared as an off-white powder: MS (ES) m/e 393 (M+H)$^+$.

Example 83

Preparation of (E)-N-(quinolin-3-ylmethyl)-N-methyl-3-(7-oxo-5,6,7,8-tetrahydro-1,8-naphthyridin-3-yl)acrylamide According to the procedure of Example 24, except substituting 3-(methylaminomethyl)quinoline (0.12 g, 0.67 mmole) for the 2,3-dihydro-8-(methylaminomethyl)-1H-3a-azacyclopenta[a]indene), the title compound (0.1 g, 40%) was prepared as an off-white powder: MS (ES) m/e 373 (M+H)$^+$.

Example 84

Preparation of (E)-N-(naphthalen-1-ylmethyl)-N-methyl-3-(7-oxo-5,6,7,8-tetrahydro-1,8-naphthyridin-3-yl)acrylamide According to the procedure of Example 24, except substituting N-methyl-1-naphthalenemethylamine hydrochloride (0.162 g, 0.95 mmole) for the 2,3-dihydro-8-(methylaminomethyl)-1H-3a-azacyclopenta[a]indene), the title compound (0.15 g, 43%) was prepared as a white powder: MS (ES) m/e 372 (M+H)$^+$.

Example 85

Preparation of (E)-N-methyl-N-(2-methyl-1H-indol-3-ylmethyl)-3-[3-(2-methoxyethyl)-2-oxo-1,2,3,4-tetrahydropyrido[2,3-d]pyrimidin-6-yl]acrylamide A solution of 6-bromo-3-(2-methoxyethyl)-3,4-dihydro-1H-pyrido[2,3-d]pyrimidin-2-one (0.86 g, 3.00 mmole), N-(2-methyl-1H-indol-3-ylmethyl)-N-methylacrylamide (see Example 1 (a), 0.68 g, 3.00 mmole), Pd(OAc)$_2$ (0.07 g, 0.30 mmole), tri-ortho-tolylphosphine (0.18 g, 0.60 mmole) and diisopropylethylamine (1.31 mL, 7.50 mmole) in propionitrile (50 mL) was deoxygenated, then was heated at reflux under N$_2$ overnight. The dark mixture was filtered through a pad of Celite®, and the filter pad was rinsed with acetonitrile (250 mL). The filtrate was concentrated in vacuo, and the residue was purified by flash chromatography on silica gel (10% EtOAc/EtOH). The title compound (0.46 g, 36%) was obtained as a light yellow solid after drying in vacuo: MS (ES) m/e 434 (M+H)$^+$.

Example 86

Preparation of (E)-N-(1-methyl-1H-indol-3-ylmethyl)-N-methyl-3-(6-methoxycarbonyl-7-oxo-5,6,7,8-tetrahydro-1,8-naphthyridin-3-yl)acrylamide According to the procedure of Example 15 (b), except substituting methyl (±)-6-bromo-2-oxo-1,2,3,4-tetrahydro-1H-1,8-naphthyridine-3-carboxylate (2.5 g, 8.8 mmole), from Preparation 4 (d), for the 5-bromo-2,2'-dipyridylamine, the title compound (1.82 g, 48%) was prepared as an off-white solid: MS (ES) m/e 433.4 (M+H)$^+$.

Example 87

Preparation of (E)-3-(6-aminopyridin-3-yl)-N-(1,3-dimethyl-1H-pyrrolo[2,3-b]pyridin-3-ylmethyl)-N-methylacrylamide The title compound is prepared following methods analogous to those described in the previous preparations and examples.

Example 88

Preparation of (E)-N-(1,3-dimethyl-1H-pyrrolo[2,3-b]pyridin-3-ylmethyl)-N-methyl-3-(7-oxo-5,6,7,8-tetrahydro-1,8-naphthyridin-3-yl)acrylamide The title compound is prepared following methods analogous to those described in the previous preparations and examples.

Example 89

Preparation of (E)-3-(6-aminopyridin-3-yl)-N-methyl-N-(1-methyl-1H-pyrrolo[2,3-c]pyridin-3-ylmethyl)acrylamide The title compound is prepared following methods analogous to those described in the previous preparations and examples.

Example 90

Preparation of (E)-3-(6-aminopyridin-3-yl)-N-methyl-N-(1-methyl-1H-pyrrolo[3,2-c]pyridin-3-ylmethyl)acrylamide The title compound is prepared following methods analogous to those described in the previous preparations and examples.

Example 91

Preparation of (E)-3-(6-aminopyridin-3-yl)-N-methyl-N-(1-methyl-1H-pyrrolo[3,2-b]pyridin-3-ylmethyl)acrylamide The title compound is prepared following methods analogous to those described in the previous preparations and examples.

Example 92

Preparation of (E)-N-methyl-N-(1-methyl-1H-pyrrolo[2,3-c]pyridin-3-ylmethyl)-3-(7-oxo-5,6,7,8-tetrahydro-1,8-naphthyridin-3-yl)acrylamide The title compound is prepared following methods analogous to those described in the previous preparations and examples.

Example 93

Preparation of (E)-N-methyl-N-(1-methyl-1H-pyrrolo[3,2-c]pyridin-3-ylmethyl)-3-(7-oxo-5,6,7,8-tetrahydro-1,8-naphthyridin-3-yl)acrylamide The title compound is prepared following methods analogous to those described in the previous preparations and examples.

Example 94

Preparation of (E)-N-methyl-N-(1-methyl-1H-pyrrolo[3,2-b]pyridin-3-ylmethyl)-3-(7-oxo-5,6,7,8-tetrahydro-1,8-naphthyridin-3-yl)acrylamide The title compound is prepared following methods analogous to those described in the previous preparations and examples.

Example 95

Preparation of (E)-3-(6-aminopyridin-3-yl)-N-(benzofuran-3-ylmethyl)-N-methylacrylamide The title compound is prepared following methods analogous to those described in the previous preparations and examples.

Example 96

Preparation of (E)-3-(6-aminopyridin-3-yl)-N-methyl-N-(3-methylbenzofuran-2-ylmethyl)acrylamide The title compound is prepared following methods analogous to those described in the previous preparations and examples.

Example 97

Preparation of (E)-3-(6-aminopyridin-3-yl)-N-methyl-N-(2-methylbenzofuran-3-ylmethyl)acrylamide The title compound is prepared following methods analogous to those described in the previous preparations and examples.

Example 98

Preparation of (E)-N-(benzofuran-3-ylmethyl)-N-methyl-3-(7-oxo-5,6,7,8-tetrahydro-1,8-naphthyridin-3-yl)acrylamide The title compound is prepared following methods analogous to those described in the previous preparations and examples.

Example 99

Preparation of (E)-N-methyl-N-(3-methylbenzofuran-2-ylmethyl)-3-(7-oxo-5,6,7,8-tetrahydro-1,8-naphthyridin-3-yl)acrylamide The title compound is prepared following methods analogous to those described in the previous preparations and examples.

Example 100

Preparation of (E)-N-methyl-N-(2-methylbenzofuran-3-ylmethyl)-3-(7-oxo-5,6,7,8-tetrahydro-1,8-naphthyridin-3-yl)acrylamide The title compound is prepared following methods analogous to those described in the previous preparations and examples.

Example 101

Preparation of (E)-(6-aminopyridin-3-yl)-N-methyl-N-[1-(1-methyl-1H-indol-2-yl)ethyl]acrylamide The title compound is prepared following methods analogous to those described in the previous preparations and examples.

Example 102

Preparation of (E)-(6-aminopyridin-3-yl)-N-methyl-N-[1-(1-methyl-1H-indol-3-yl)ethyl]acrylamide The title compound is prepared following methods analogous to those described in the previous preparations and examples.

Example 103

Preparation of (E)-N-methyl-N-[1-(1-methyl-1H-indol-2-yl)ethyl]-3-(7-oxo-5,6,7,8-tetrahydro-1,8-naphthyridin-3-yl)acrylamide The title compound is prepared following methods analogous to those described in the previous preparations and examples.

Example 104

Preparation of (E)-N-methyl-N-[1-(1-methyl-1H-indol-3-yl)ethyl]-3-(7-oxo-5,6,7,8-tetrahydro-1,8-naphthyridin-3-yl)acrylamide The title compound is prepared following methods analogous to those described in the previous preparations and examples.

Example 105

Parenteral Dosage Unit Composition

A preparation which contains 20 mg of the compound of Example 1 as a sterile dry powder is prepared as follows: 20 mg of the compound is dissolved in 15 mL of distilled water. The solution is filtered under sterile conditions into a 25 mL multi-dose ampoule and lyophilized. The powder is reconstituted by addition of 20 mL of 5% dextrose in water (D5W) for intravenous or intramuscular injection. The dosage is thereby determined by the injection volume. Subsequent dilution may be made by addition of a metered volume of this dosage unit to another volume of D5W for injection, or a metered dose may be added to another mechanism for dispensing the drug, as in a bottle or bag for IV drip infusion or other injection-infusion system.

Example 106

Oral Dosage Unit Composition

A capsule for oral administration is prepared by mixing and milling 50 mg of the compound of Example 1 with 75 mg of lactose and 5 mg of magnesium stearate. The resulting powder is screened and filled into a hard gelatin capsule.

Example 107

Oral Dosage Unit Composition

A tablet for oral administration is prepared by mixing and granulating 20 mg of sucrose, 150 mg of calcium sulfate dihydrate and 50 mg of the compound of Example 1 with a 10% gelatin solution. The wet granules are screened, dried, mixed with 10 mg starch, 5 mg talc and 3 mg stearic acid; and compressed into a tablet.

The above description fully discloses how to make and use the present invention. However, the present invention is not limited to the particular embodiments described hereinabove, but includes all modifications thereof within the scope of the following claims. The various references to journals, patents and other publications which are cited herein comprises the state of the art and are incorporated herein by reference as though fully set forth.

---

What is claimed is:

1. A compound according to formula (II):

wherein:

$A^*B^*$ is

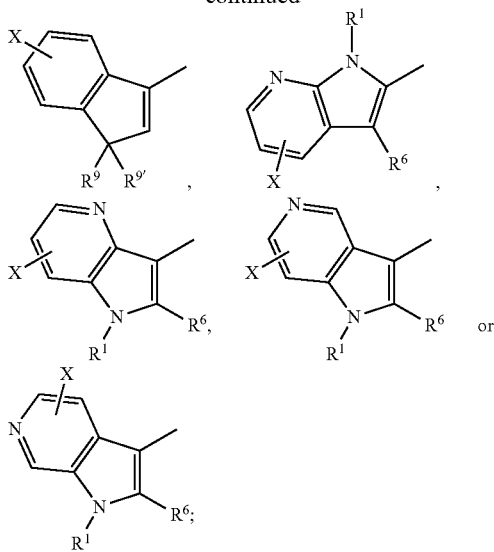

R¹ is H or $C_{1-4}$alkyl;
R² is H, $C_{1-4}$alkyl or $C_{3-6}$cycloalkyl;
R³ is

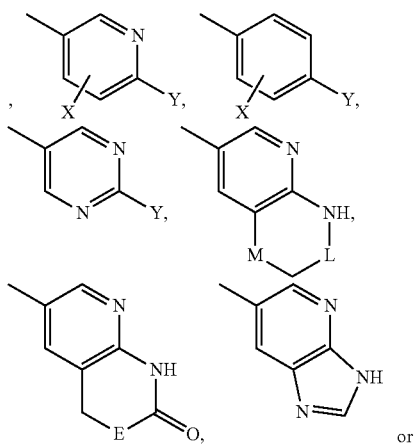

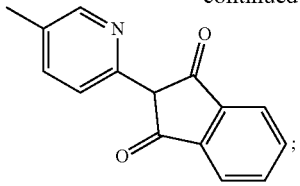

R⁴ is H or $C_{1-4}$alkyl;

indicates that one of the two designated bonds is a double bond and the other is a single bond;
R⁵ is CH₂ when the bond to which it is attached is a double bond; or R⁵ is H or $C_{1-4}$alkyl when the bond to which it is attached is a single bond;
R⁶ is H or $C_{1-4}$alkyl;
R⁸ is H or $C_{1-4}$alkyl;
R⁹ and R⁹' independently are H or $C_{1-4}$alkyl;
Y is H, $C_{1-4}$alkyl, N(R')₂, NHC(O)R', NHCH₂C(O)R' or NHC(O)CH=CHR';
each X independently is H, $C_{1-4}$alkyl, CH₂OH, OR', SR', CN, N(R')₂, CH₂N(R')₂, NO₂, CF₃, CO₂R', CON(R')₂, COR', NR'C(O)R', F, Cl, Br, I or —S(O)$_r$CF₃;
W is S or O;
M is CH₂ or O;
L is CH₂ or C(O);
E is O or NR'; and
each R' independently is H, $C_{1-6}$alkyl or —$C_{0-6}$alkyl-Ar; and r is 0, 1 or 2;
or a pharmaceutically acceptable salt thereof.

2. A pharmaceutical composition comprising a compound according to claim 1 and a pharmaceutically acceptable carrier.

3. A method of treating bacterial infections which comprises administering to a subject in need thereof a therapeutically effective amount of a composition according to claim 2.

* * * * *

SEQUENCE LISTING

<160> NUMBER OF SEQ ID NOS: 6

<210> SEQ ID NO 1
<211> LENGTH: 39
<212> TYPE: DNA
<213> ORGANISM: Artificial Sequence
<220> FEATURE:
<223> OTHER INFORMATION: Description of Artificial Sequence: Primer -continued

```
<400> SEQUENCE: 1
cgcctcgaga tgttaaatct tgaaaacaaa acatatgtc                                    39

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 2
cgcggatcca atcaagtcag gttgaaatat cca                                          33

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
catgggctta aatcttgaaa acaaaaca                                                28

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tatgttttgt tttcaagatt taagcc                                                  26

<210> SEQ ID NO 5
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 5
gcggtaccca tgcgcttggt tttcttagaa atattg                                       36

<210> SEQ ID NO 6
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 6
gcggccgctt attcttcgcc taattcgccc attgc                                        35
```